(12) United States Patent
Liotta et al.

(10) Patent No.: US 8,080,659 B2
(45) Date of Patent: *Dec. 20, 2011

(54) CXCR4 ANTAGONISTS INCLUDING DIAZINE AND TRIAZINE STRUCTURES FOR THE TREATMENT OF MEDICAL DISORDERS

(75) Inventors: Dennis C. Liotta, Atlanta, GA (US); James P. Snyder, Atlanta, GA (US); Weiqiang Zhan, Decatur, GA (US)

(73) Assignee: Emory University, Atlanta, GA (US)

( * ) Notice: Subject to any disclaimer, the term of this patent is extended or adjusted under 35 U.S.C. 154(b) by 946 days.

This patent is subject to a terminal disclaimer.

(21) Appl. No.: 11/776,476

(22) Filed: Jul. 11, 2007

(65) Prior Publication Data

US 2009/0099194 A1  Apr. 16, 2009

Related U.S. Application Data

(60) Provisional application No. 60/819,997, filed on Jul. 11, 2006, provisional application No. 60/830,006, filed on Jul. 11, 2006.

(51) Int. Cl.
*C07D 403/12* (2006.01)
*C07D 403/14* (2006.01)
*A61K 31/506* (2006.01)
*A61P 35/00* (2006.01)

(52) U.S. Cl. ........ 544/330; 544/331; 544/332; 544/320; 544/321; 514/269; 514/275; 514/252.14

(58) Field of Classification Search .................. 544/330, 544/331, 332, 320, 321; 514/269, 275, 252.14
See application file for complete search history.

(56) References Cited

U.S. PATENT DOCUMENTS

| | | | |
|---|---|---|---|
| 5,874,438 A | 2/1999 | Schohe-Loop et al. | |
| 5,993,817 A | 11/1999 | Yoneda et al. | |
| 6,344,545 B1 | 2/2002 | Allaway et al. | |
| 6,358,915 B1 | 3/2002 | Patierno et al. | |
| 6,420,354 B1 * | 7/2002 | Marquess et al. | 514/183 |
| 6,429,308 B1 | 8/2002 | Iijima et al. | |
| 6,433,149 B1 | 8/2002 | Blaschuk et al. | |
| 6,475,488 B1 | 11/2002 | Pasqualini et al. | |
| 6,534,626 B1 | 3/2003 | Oravecz et al. | |
| 6,750,348 B1 | 6/2004 | Bridger et al. | |
| 2004/0132642 A1 | 7/2004 | Hwang | |
| 2004/0254221 A1 | 12/2004 | Yamazaki et al. | |
| 2006/0264451 A1 | 11/2006 | Shim et al. | |
| 2007/0054930 A1 | 3/2007 | Shim et al. | |
| 2008/0227799 A1 | 9/2008 | Liotta et al. | |

FOREIGN PATENT DOCUMENTS

| | | |
|---|---|---|
| WO | WO 97/00956 A1 | 1/1997 |
| WO | WO 99/47158 A2 | 9/1999 |
| WO | WO 00/56729 A1 | 9/2000 |
| WO | WO 01/38352 A2 | 5/2001 |
| WO | WO 01/56591 A1 | 8/2001 |
| WO | 2001/070727 A1 | 9/2001 |
| WO | WO 01/70727 A1 * | 9/2001 |
| WO | WO 01/85196 A2 | 11/2001 |
| WO | WO 02/094261 A1 | 11/2002 |
| WO | WO 03/029218 A1 | 4/2003 |
| WO | WO 2004/020462 A1 | 3/2004 |
| WO | WO 2004/024178 A1 | 3/2004 |
| WO | WO 2004/093817 A2 | 4/2004 |
| WO | WO 2004/059285 A2 | 7/2004 |
| WO | WO 2004/087068 A2 | 10/2004 |
| WO | WO 2004/091518 A2 | 10/2004 |
| WO | WO 2004/106493 A2 | 12/2004 |
| WO | WO 2006/074426 A2 | 7/2006 |
| WO | WO 2006/074428 A2 | 7/2006 |

OTHER PUBLICATIONS

Rostene et al., Nature Reviews Neuroscience, 8, 895-904, 200.*
Raman et al., Cancer Letters, 256, 137-165, 2007.*
Freshney et al.,Culture of Animal Cells, A Manual of Basic Technique, Alan R. Liss, Inc., 1983, New York, p4.*
Dermer et al., Bio/Technology, 1994, 12:320.*
Golub et al., Science, 286, 531-537, 1999.*
Cecil Textbook of Medicine, edited by Bennet, J.C., and Plum F., 20th edition,vol. 1, 1004-1010, 1996.*
Wolft Manfred E. "Burger's Medicinal Chemistry, 5ed, Part 1", John Wiley & Sons, 1995, pp. 975-977.*
Banker, G.S. et al, "Modern Pharmaceutics, 3ed.", Marcel Dekker, New York. 1996, pp. 451 and 596.*
U.S. Appl. No. 11/776,465, Liotta et al.
Abdel-Magid, A.F., et al., "Reductive Amination of Aldehydes and Ketones with Sodium Triacetoxyborohydride. Studies on Direct and Indirect Reductive Amination Procedures(1)," *J. Org. Chem.* 61(11):3849-3862 (May 31, 1996).
Abi-Younes, S., et al., "The stromal cell-derived factor-1 chemokine is a potent platelet agonist highly expressed in atherosclerotic plaques," *Circ. Res.*, 86(2), 131-138 (Feb. 4, 2000)).
Alkhatib, G., et al., "CC CKR5: a RANTES, MIP-1alpha, MIP-1beta receptor as a fusion cofactor for macrophage-tropic HIV-1," *Science*, 272(5270):1955-1958 (Jun. 28, 1996).
Blades, M.C., et al., "Stromal cell-derived factor 1 (CXCL12) induces human cell migration into human lymph nodes transplanted into SCID mice," *J. Immunol.* 168(9):4308-4317 (May 1, 2002).
Bleul, C.C., et al., "The lymphocyte chemoattractant SDF-1 is a ligand for LESTR/fusin and blocks HIV-1 entry," *Nature*, 382(6594):829-833 (Aug. 29, 1996).

(Continued)

*Primary Examiner* — Venkataraman Balasubramanian
(74) *Attorney, Agent, or Firm* — Emory University Patent Group

(57) ABSTRACT

The invention provides compounds, pharmaceutical compositions and methods of use of certain compounds that are antagonists of the chemokine CXCR4 receptor for the treatment of proliferative conditions mediated by CXCR4 receptors or for the treatment of viral infections. The compounds provided interfere with the binding of SDF1 to the receptor. These compounds are particularly useful for treating or reducing the severity of hyperproliferative diseases by inhibiting metastasis, or for reducing entry of HIV in to a cell while not reducing the capacity of the stem cells to proliferate. The compounds may be useful for long term treatment regimes.

7 Claims, 17 Drawing Sheets

(8 of 17 Drawing Sheet(s) Filed in Color)

OTHER PUBLICATIONS

Braun, C.E., et al., "Guanidine structure and hypoglycemia: some carbocyclic diguanidines," *J. Org. Chem.*, 3(2):146-152 (1938).

Bressler, N.M., and Bressler, S.B., "Preventative ophthalmology. Age-related macular degeneration," *Ophthalmology*, 102(8):1206-1211 (Aug. 1995).

Butcher, E.C., et al. "Lymphocyte trafficking and regional immunity," *Adv. Immunol.*, 72:209-253 (1999).

Campbell, J.J., and Butcher, E.C., "Chemokines in tissue-specific and microenvironment-specific lymphocyte homing," *Curr. Opin. Immunol.*,12(3):336-341 (Jun. 2000).

Chen, W.J., et al. "Recombinant human CXC-chemokine receptor-4 in melanophores are linked to Gi protein: seven transmembrane coreceptors for human immunodeficiency virus entry into cells," *Mol. Pharmacol.*, 53(2):177-181 (Feb. 1998).

Connor, R.I., et al., "Change in coreceptor use correlates with disease progression in HIV-1—infected individuals," *J. Exp. Med.*, 185(4):621-628 (Feb. 17, 1997).

Crane, I.J., et al., "CXCR4 receptor expression on human retinal pigment epithelial cells from the blood-retina barrier leads to chemokine secretion and migration in response to stromal cell-derived factor 1 alpha," *J. Immunol.*, 165(8):4372-4378 (Oct. 15, 2000).

Davis, C.B., et al. "Signal transduction due to HIV-1 envelope interactions with chemokine receptors CXCR4 or CCR5," *J. Exp. Med.*, 186(10):1793-1798 (Nov. 17, 1997).

Deng, H.K., et al., "Expression cloning of new receptors used by simian and human immunodeficiency viruses," *Nature*, 388(6639):296-300 (Jul. 17, 1997).

Donzella, G.A., et al., "AMD3100, a small molecule inhibitor of HIV-1 entry via the CXCR4 co-receptor," *Nat. Med.*, 4(1):72-77 (Jan. 1998).

Doranz, B.J., et al., "A dual-tropic primary HIV-1 isolate that uses fusin and the beta-chemokine receptors CKR-5, CKR-3, and CKR-2b as fusion cofactors," *Cell*, 85(7):1149-1158 (Jun. 28, 1996).

Dwinell, M.B., et al., "Chemokine receptor expression by human intestinal epithelial cells," *Gastroenterology*, 117(2):359-367 (Aug. 1999).

Eitner, F., et al., "Chemokine receptor (CXCR4) mRNA-expressing leukocytes are increased in human renal allograft rejection," *Transplantation*, 66(11):1551-1557 (Dec. 15, 1998).

Feng, Y, et al., "HIV-1 entry cofactor: functional cDNA cloning of a seven-transmembrane, G protein-coupled receptor," *Science*, 272(5263):872-877 (May 10, 1996).

Förster, R., et al., "CCR7 coordinates the primary immune response by establishing functional microenvironments in secondary lymphoid organs," *Cell*, 99(1):23-33 (Oct. 1, 1999).

Fujii, N., et al., "The therapeutic potential of CXCR4 antagonists in the treatment of HIV," *Expert Opin. Investig. Drugs*, 12(2):185-195 (Feb. 2003).

Gonzalo, J.A., et al., "Critical involvement of the chemotactic axis CXCR4/stromal cell-derived factor-1 alpha in the inflammatory component of allergic airway disease," *J. Immunol.*, 165(1),499-508 (Jul. 1, 2000).

Grove, G., "Epidermal cell kinetics in psoriasis," *Int. J. Dermatol.*, 18(2):111-122 (Mar. 1979).

Gupta, S.K., et al., "Chemokine receptors in human endothelial cells. Functional expression of CXCR4 and its transcriptional regulation by inflammatory cytokines," *J. Biol. Chem.*, 273(7):4282-4287 (Feb. 13, 1998).

Harris, E. D., Jr., "Rheumatoid arthritis. Pathophysiology and implications for therapy," *N. Eng. J. Med.*, 322(18):1277-1289 (May 3, 1990).

Hatse, S., et al., "Chemokine receptor inhibition by AMD3100 is strictly confined to CXCR4," *FEBS Lett* 527(1-3):255-262 (Sep. 11, 2002).

Hendrix, C.W., et al., "Safety, pharmacokinetics, and antiviral activity of AMD3100, a selective CXCR4 receptor inhibitor, in HIV-1 infection," *J. Acquir. Immune Defic. Syndr.*, 37(2):1253-1262 (Oct. 1, 2004).

Homey, B., et al., "Cutting edge: the orphan chemokine receptor G protein-coupled receptor-2 (GPR-2, CCR10) binds the skin-associated chemokine CCL27 (CTACK/ALP/ILC)," *J. Immunol.*, 164(7):3465-3470 (Apr. 1, 2000).

Kang, Y., et al., "A multigenic program mediating breast cancer metastasis to bone," *Cancer Cell*, 3(6):537-549 (Jun. 2003).

Kijowski, J., et al., "The SDF-1-CXCR4 axis stimulates VEGF secretion and activates integrins but does not affect proliferation and survival in lymphohematopoietic cells," *Stem Cells* 19(5):453-466 (2001).

Linton, B.R., et al., "Thermodynamic aspects of dicarboxylate recognition by simple artificial receptors," *J. Org. Chem.*, 66(22):7313-7319 (Nov. 2, 2001).

Majka, M., et al., "Biological significance of chemokine receptor expression by normal human megakaryoblasts," *Folia. Histochem. Cytobiol.* 39(3):235-244 (2001).

Mićović, V.M., and Mihailović, M.LJ., "The Reduction of Acid Amides with Lithium Aluminum Hydride," *J. Org. Chem.*, 18(9):1190-1200 (1953).

Mitra, P., et al., "CXCR4 mRNA expression in colon, esophageal and gastric cancers and hepatitis C infected liver," *Int. J. Oncol.*, 14(5):917-925 (May 1999).

Morales, J., et al., "CTACK, a skin-associated chemokine that preferentially attracts skin-homing memory T cells," *Proc. Natl. Acad. Sci. U.S.A.*, 96(25):14470-14475 (Dec. 7, 1999).

Müller, A., et al., "Involvement of chemokine receptors in breast cancer metastasis," *Nature*, 410(6824):50-56 (Mar. 1, 2001).

Murdoch, C., et al., "Functional expression of chemokine receptor CXCR4 on human epithelial cells," *Immunology*, 98(1):36-41 (Sep. 1998).

Murdock, K.C., et al., "Antitumor agents. 2. Bisguanylhydrazones of anthracene-9,10-dicarboxaldehydes," *J. Med. Chem.* 25(5):505-518 (May 1982).

Nagase, H., et al., "Expression of CXCR4 in eosinophils: functional analyses and cytokine-mediated regulation," *J. Immunol.*, 164(11):5935-5943 (Jun. 1, 2000).

Nanki, T., and Lipsky, P.E., et al., "Cutting edge: stromal cell-derived factor-1 is a costimulator for CD4+ T cell activation," *J. Immunol.*, 164(10):5010-5014 (May 15, 2000).

Onuffer, J.J., and Horuk, R., "Chemokines, chemokine receptors and small-molecule antagonists: recent developments," *Trends Pharmacol. Sci.*, 23(10):459-467 (Oct. 2002).

Peled, A., et al., "Dependence of human stem cell engraftment and repopulation of NOD/SCID mice on CXCR4," *Science*, 283(5403):845-848 (Feb. 5, 1999).

Post, D. E., and Van Meir, E. G., "Generation of bidirectional hypoxia/HIF-responsive expression vectors to target gene expression to hypoxic cells," *Gene Ther.*, 8(23):1801-1807 (Dec. 2001).

Reyes, M.J., et al., "Pyridinium N-(2'-azinyl)aminides: regioselective synthesis of N-(2-pyridyl) substituted polyamines," *Tetrahedron*, 58(42):8573-8579 (Oct. 14, 2002).

Ross, R., "The pathogenesis of atherosclerosis: a perspective for the 1990s," *Nature*, 362(6423):801-809 (Apr. 29, 1993).

Sanchez, X., et al., "Activation of HIV-1 coreceptor (CXCR4) mediates myelosuppression," *J. Biol. Chem.*, 272(34):27529-27531 (Oct. 31, 1997).

Schols, D., et al., "Bicyclams, a class of potent anti-HIV agents, are targeted at the HIV coreceptor fusin/CXCR-4," *Antiviral Res.*, 35(3):147-156 (Aug. 1997).

Scozzafava, A., et al. "Non-peptidic chemokine receptors antagonists as emerging anti-HIV agents," *J. Enzyme Inhib. Med. Chem.*, 17(2):69-76 (Apr. 2002).

Sotsios, Y., et al., "The CXC chemokine stromal cell-derived factor activates a Gi-coupled phosphoinositide 3-kinase in T lymphocytes," *J. Immunol.*, 163(11): 5954-5963 (Dec. 1, 1999).

Staller, P., et al., "Chemokine receptor CXCR4 downregulated by von Hippel-Lindau tumour suppressor pVHL," *Nature*, 425(6955):307-311 (Sep. 18, 2003).

Tamamura, H., et al., "A low-molecular-weight inhibitor against the chemokine receptor CXCR4: a strong anti-HIV peptide T140," *Biochem. Biophys. Res. Commun.*, 253(3): 877-882 (Dec. 30, 1998).

Tamamura, H., et al., "Development of specific CXCR4 inhibitors possessing high selectivity indexes as well as complete stability in serum based on an anti-HIV peptide T140," *Bioorg. Med. Chem. Lett.*, 11(14):1897-1902 (Jul. 23, 2001).

Tamamura, H., et al., "Pharmacophore identification of a specific CXCR4 inhibitor, T140, leads to development of effective anti-HIV agents with very high selectivity indexes," *Bioorg. Med. Chem. Lett.*, 10(23):2633-2637 (Dec. 4, 2000).

Trent, J.O., et al., "Lipid bilayer simulations of CXCR4 with inverse agonists and weak partial agonists," *J. Biol. Chem.*, 278(47):47136-47144 (Nov. 21, 2003) (Epublication Sep. 4, 2003).

Vlahakis, S.R., et al., "G protein-coupled chemokine receptors induce both survival and apoptotic signaling pathways," *J. Immunol.* 169(10):5546-5554 (Nov. 15, 2002).

Volin, M.V., et al., "Chemokine receptor CXCR4 expression in endothelium," *Biochem Biophys Res Commnun.*, 242(1):46-53 (Jan. 6, 1998).

Xia, M.Q., and Hyman, B.T., "Chemokines/chemokine receptors in the central nervous system and Alzheimer's disease," *J. NeuroVirol.*, 5(1):32-41 (Feb. 1999).

Yssel, H., et al., "The role of IgE in asthma," *Clin. Exp. Allergy*; 28(28 Suppl. 5):104-109; discussion 117-118 (Nov. 1998).

Zaitseva, M., et al., "Expression and function of CCR5 and CXCR4 on human Langerhans cells and macrophages: implications for HIV primary infection," *Nat. Med.*, 3(12):1369-1375 (Dec. 1997).

Zlotnik, A., and Yoshie, Q., "Chemokines: a new classification system and their role in immunity," *Immunity*, 12(2):121-127 (Feb. 2000).

Zou, R.-Y., et al., "1,4-Bis(pyridine-2-aminomethyl)benzene," *Acta Crystallographica Section E*, E59(9):(online)o1312-o1313 (Sep. 2003) (Provided as publisher's abstract).

Kawamura, et al., ., et al., Preparation of Novel Substitutes Fused Imidazole Derivatives, No. 144:292780, abstact, RN87877 5-72-2.

King, et al. Bioisosteres, Confirmational Restriction, and Pro-Drugs-Case History, (994) pp. 206-209, Bioisosterimsm.

Boyton, A.L., 2006, "CXCR4 is over-expressed on [greater than] 75% of cancers and absent on most non-neoplastic cells." Journal of Clinical Oncology, 2006 ASCO Annual Meeting Proceedings (Post-Meeting Edition), Abstract, vol. 24, No. 18S (Jun. 20 Supplement).

Dillmann, et al., 2009, "Plerixafor inhibits chemotaxis toward SDF-1 and CXCR4-mediated stroma contact in a dose-dependent manner resulting in increased susceptibility of BCR-ABL+ cell to Imatinib and Nilotinib.", Leuk Lymphoma, 50(10):1676-86.

Imai, T., 2006 "Human carboxylesterase isozymes: catalytic properties and rational drug design" Drug Metab Pharmacokinet, 21(3):173-85.

Juarez, J. et al 2003, "Effects of inhibitors of the chemokine receptor CXCR4 on acute lymphoblastic leukemia cells in vitro", Leukemia, 17(7):1294-3000.

Kast, R., 2010, "Profound blockage of CXCR4 signaling at multiple points using the synergy between plerixafor, mirtazapine, and clotrimazole as a new glioblastoma treatment adjunct", Turk Neurosurg, 20(4):425-9.

Lee, et al., 2010, "PAUF functions in the metastasis of human pancreatic cancer cells and upregulates CXCR4 expression", Oncogene, 29(1):56-67.

Li, et al. 2008, "Inhibition of CXCR4 activity with AMD3100 decreases invasion of human colorectal cancer cells in vitro," World J Gastroenterol, 14(15):2308-13.

Redjal, et al. 2006, "CXCR4 inhibition synergizes with cytotoxic chemotherapy in gliomas", Clin Cancer Res,12 (22):6765-71.

Rubin, et al., 2003, "A small-molecule antagonist of CXCR4 inhibits intracranial growth of primary brain tumors", Proc Natl Acad Sci U S A, 100(23):13513-8.

Scotton, et al., 2002, "Multiple actions of the chemokine CXCL12 on epithelial tumor cells in human ovarian cancer", Cancer Res, 62(20):5930-8.

Smith, et al., 2004, "CXCR4 regulates growth of both primary and metastatic breast cancer", Cancer Res, 64 (23):8604-12.

Uchida, et al., 2007, "Involvement of an autocrine stromal cell derived factor-1/CXCR4 system on the distant metastasis of human oral squamous cell carcinoma", Mol Cancer Res, 5(7):685-94.

Yasumoto, et al., 2006, "Role of the CXCL12/CXCR4 axis in peritoneal carcinomatosis of gastric cancer", Cancer Res,66(4):2181-7.

Zhu, et al, 2010, "Dipyrimidine Amines: A Novel Class of Chemokine Receptor Type 4 Antagonist with High Specificity", J of Medicinal Chemistry, 53, pp. 8556-8568.

* cited by examiner

CXCR4 ANTAGONISTS INCLUDING DIAZINE AND TRIAZINE STRUCTURES FOR THE TREATMENT OF MEDICAL DISORDERS

CROSS-REFERENCE TO RELATED APPLICATIONS

This application claims priority to U.S. Provisional Application No. 60/819,997, filed Jul. 11, 2006, and U.S. Provisional Application No. 60/830,006, filed Jul. 11, 2006.

FIELD OF THE INVENTION

The invention provides compounds, pharmaceutical compositions and methods of use of certain compounds that are antagonists of the chemokine CXCR4 receptor. The compounds are useful to mediate any medical condition that is modulated by CXCR4 receptor signaling, and in particular for treating or reducing the severity of hyperproliferative diseases by inhibiting metastasis, or in the treatment or prevention of human immunodeficiency virus infections (HIV).

BACKGROUND OF THE INVENTION

Cancer is currently the second leading cause of death in developed nations. In 2004, the American Cancer Society estimated that approximately 1.37 million new cases were diagnosed in the U.S. alone, and approximately 550,000 deaths occurred due to cancer (American Cancer Society, Cancer Facts & Figures 2004, see URL: http://www.cancer.org/docroot/STT/stt_0.asp).

Metastasis, the spread and growth of tumor cells to distant organs, is the most devastating attribute of cancer. Most morbidity and mortality associated with certain types of cancer, such as breast cancer, is associated with disease caused by metastatic cells rather than by the primary tumor. Therapy for metastasis currently relies on a combination of early diagnosis and aggressive treatment of the primary tumor.

The establishment and growth of metastases at distant sites is thought to depend on interactions between tumor cells and the host environment. Metastasis is the result of several sequential steps and represents a highly organized, non-random and organ-selective process. Although a number of mediators have been implicated in the metastasis of breast cancer, the precise mechanisms determining the directional migration and invasion of tumor cells into specific organs remain to be established. An incomplete understanding of the molecular and cellular mechanisms underlying metastasis has hindered the development of effective therapies that would eliminate or ameliorate this condition.

Several strategies have been developed to reduce metastatic invasion of malignant cells by regulating adhesion of endothelial cells with antibodies or adhesion molecules (see for example, PCT Publication No. WO 97/00956, U.S. Pat. Nos. 5,993,817; 6,433,149; 6,475,488; and 6,358,915). However no commercial strategy has provided an effective treatment to prevent metastasis.

According to UNAIDS/WHO 2006 AIDS Epidemic Update, an estimated 39.5 million people are living with HIV (http://www.who.int/hiv/mediacentre/news62/en/index.html). There were 4.3 million new infections in 2006 with 2.8 million (65%) of these occurring in sub-Saharan Africa and important increases in Eastern Europe and Central Asia, where there are some indications that infection rates have risen by more than 50% since 2004. In 2006, 2.9 million people died of AIDS-related illnesses. The Centers for Disease Control and Prevention (CDC) estimate that, as of the end of 2003, an estimated 1,039,000 to 1,185,000 persons in the United States were living with HIV/AIDS (http://www.cdc.gov/hiv/resources/factsheets/At-A-Glance.htm). Although new infections have decreased in recent years, an estimated 4.9 million new HIV infections occurred worldwide during 2004 and approximately 40,000 new HIV infections occur each year in the United States.

HIV entry within the target cells involves a series of molecular events. The three main steps of virus entry within the cell are: (i) attachment of the virus to the host cells; (ii) interaction of the virus with the co-receptors; (iii) fusion of the virus and host cell membranes. Considering the complexity of the molecular events involved in viral infection, all three of these steps have been considered for the drug design of HIV entry inhibitors. The T-lymphocyte cell surface protein CD4 is the primary receptor involved in the interaction with the viral glycoprotein gp120, but a cellular co-receptor is also needed for the successful entry of the virus within the cell. At least two types of such co-receptors have been identified so far, both of which are chemokine receptors. These chemokine receptors are therefore gateways for HIV entry, determinants of viral tropism and sensitivity.

Chemokines are a superfamily of small cytokines that induce, through their interaction with G-protein-coupled receptors, cytoskeletal rearrangements and directional migration of several cell types. These secreted proteins act in a coordinated fashion with cell-surface proteins to direct the homing of various subsets of cells to specific anatomical sites (Morales, et al. (1999) *Proc Natl Acad Sci USA* 96: 14470-14475; Homey, B., et al. (2000) *J Immunol* 164: 3465-3470; Peled, et al. (1999) *Science* 283: 845-848; Forster, et al. (1999) *Cell* 99: 23-33).

Chemokines are considered to be principal mediators in the initiation and maintenance of inflammation. They have also been found to play an important role in the regulation of endothelial cell function, including proliferation, migration and differentiation during angiogenesis and re-endothelialization after injury (Gupta et al. (1998) *J Biol Chem,* 7:4282-4287). Two specific chemokines have also been implicated in the etiology of infection by human immunodeficiency virus (HIV).

The chemokine receptor, CXCR4, is known in viral research as a major coreceptor for the entry of T cell linetropic HIV (Feng, et al. (1996) *Science* 272: 872-877; Davis, et al. (1997) *J Exp Med* 186: 1793-1798; Zaitseva, et al. (1997) *Nat Med* 3: 1369-1375; Sanchez, et al. (1997) *J Biol Chem* 272: 27529-27531). Stromal cell derived factor 1 (SDF-1) is a chemokine that interacts specifically with CXCR4. When SDF-1 binds to CXCR4, CXCR4 activates $G\alpha_i$-protein-mediated signaling (pertussis toxin-sensitive), including downstream kinase pathways such as Ras/MAP Kinases and phosphatidylinositol 3-kinase (PI3K)/Akt in lymphocyte, megakaryocytes, and hematopoietic stem cells (Bleul, et al. (1996) *Nature* 382: 829-833; Deng, et al. (1997) *Nature* 388: 296-300; Kijowski, et al. (2001) *Stem Cells* 19: 453-466; Majka, et al. (2001) *Folia. Histochem. Cytobiol.* 39: 235-244; Sotsios, et al. (1999) *J. Immunol.* 163: 5954-5963; Vlahakis, et al. (2002) *J. Immunol.* 169: 5546-5554). In mice transplanted with human lymph nodes, SDF-1 induces CXCR4-positive cell migration into the transplanted lymph node (Blades, et al. (2002) *J. Immunol.* 168: 4308-4317). These results imply that the interaction between SDF-1 and CXCR4 directs cells to the organ sites with high levels of SDF-1.

Recently, studies have shown that CXCR4 interactions may regulate the migration of metastatic cells. Hypoxia, a reduction in partial oxygen pressure, is a microenvironmental change that occurs in most solid tumors and is a major inducer of tumor angiogenesis and therapeutic resistance. Hypoxia increases CXCR4 levels (Staller, et al. (2003) *Nature* 425: 307-311). Microarray analysis on a sub-population of cells from a bone metastatic model with elevated metastatic activity showed that one of the genes increased in the metastatic phenotype was CXCR4. Furthermore, overexpression CXCR4 in isolated cells significantly increased the metastatic activity (Kang, et al. (2003) *Cancer Cell* 3: 537-549). In samples collected from various breast cancer patients, Muller et al. (Muller, et al. (2001) *Nature* 410: 50-56) found that CXCR4 expression level is higher in primary tumors relative to normal mammary gland or epithelial cells. These results suggest that the expression of CXCR4 on cancer cell surfaces may direct the cancer cells to sites that express high levels of SDF-1. Consistent with this hypothesis, SDF-1 is highly expressed in the most common destinations of breast cancer metastasis including lymph nodes, lung, liver, and bone marrow. Moreover, CXCR4 antibody treatment has been shown to inhibit metastasis to regional lymph nodes when compared to control isotypes that all metastasized to lymph nodes and lungs (Muller, et al. (2001) *Nature* 410: 50-56).

In addition to regulating migration of cancer cells, CXCR4-SDF-1 interactions may regulate vascularization necessary for metastasis. Blocking either CXCR4/SDF-1 interaction or the major G-protein of CXCR4/SDF-1 signaling pathway ($G\alpha_i$) inhibits VEGF-dependent neovascularization. These results indicate that SDF-1/CXCR4 controls VEGF signaling systems that are regulators of endothelial cell morphogenesis and angiogenesis. Numerous studies have shown that VEGF and MMPs actively contribute to cancer progression and metastasis.

Several groups have identified chemokines including CXCR4 as a target for treatment of metastatic cancers. For example, PCT Publication Nos. WO 01/38352 to Schering Corporation, WO 04/059285 to Protein Design Labs, Inc., and WO 04/024178 to Burger generally describe methods of treating diseases and specifically inhibiting metastasis by blocking chemokine receptor signaling.

Compounds targeting CXCR4 have been developed primarily for treatment of HIV because CXCR4 is a major coreceptor for T-tropic HIV infection. For example, U.S. Pat. No. 6,429,308 to Hisamitsu Pharmaceutical Co., Inc. discloses an antisense oligonucleotide that inhibits the expression of the CXCR4 protein for use as an anti-HIV agent. PCT Publication No. WO 01/56591 to Thomas Jefferson University describes peptide fragments of viral macrophage inflammatory protein II which are described as selectively preventing CXCR4 signal transduction and coreceptor function in mediating entry of HIV-1.

Peptide antagonists of CXCR4 receptors have been disclosed. Tamamura et al reported the identification of a specific peptide-based CXCR4 inhibitor, T140. T140 is a 14-residue peptide that possesses anti-HIV activity and antagonism of T cell line-tropic HIV-1 entry among all antagonists of CXCR4 (Tamamura, et al. (1998) *Biochem. Biophys. Res. Commun.* 253: 877-882). The compound was altered to increase its efficacy and bioavailability by, for example, amidating the C-terminal of T-140 and reducing the total positive charges by substituting basic residues with nonbasic polar amino acids to generate TN14003, which is less cytotoxic and more stable in serum compared to T140. The concentration of TN14003 required for 50% protection of HIV-induced cytopathogenicity in MT-4 cells is 0.6 nM in contrast to 410 µM leading to 50% toxicity. PCT Publication No. WO 04/087068 to Emory University describes CXCR4 peptide antagonists, particularly TN14003, and methods of their use to treat metastasis.

U.S. Pat. No. 6,344,545 to Progenics Pharmaceuticals, Inc. describes methods for preventing HIV-1 infection of CD4+ cells with peptide fragments. U.S. Pat. No. 6,534,626 to the U.S. Department of Health & Human Services describes certain peptide chemokine variants for treating HIV infections.

Other peptide-based antagonists have also been disclosed. For example, European Patent Nos. 1 286 684 and 1 061 944 to the University of British Columbia cover methods of treatment of diseases, including metastasis, using modified peptide CXCR4 antagonists derived from the native SDF-1 ligand. PCT Publication No. WO 04/020462 to Takeda Chemical Industries, Ltd. provides peptide CXCR4 antagonists for treatment and prevention of breast cancer and chronic rheumatoid arthritis. U.S. Patent Application No. 2004/0132642 to the U.S. Dept. of Health & Human Services describes certain methods of inhibiting metastasis or growth of a tumor cell with a polypeptide CXCR4 inhibitor.

Although advances have been made, inadequate absorption, distribution, metabolism, excretion or toxicity properties of peptide inhibitors have limited their clinical uses. Small non-peptide drugs remain as a major goal of medicinal chemistry programs in this area.

At the present time, the metal-chelating cyclams and bicyclams represent one of the few reported non-peptide molecules to effectively block CXCR4 (Onuffer and Horuk (2002) *Trends Pharmacol Sci* 23: 459-467.36). One of these non-peptide molecules is AMD3100, which entered clinical trials as an anti-HIV drug that blocks CXCR4-mediated viral entry (Donzella, et al. (1998) *Nat Med* 4: 72-77; Hatse, et al. (2002) *FEBS Lett* 527: 255-262; Fujii, et al. (2003) *Expert Opin Investig Drugs* 12: 185-195; Schols, et al. (1997) *Antiviral Res* 35: 147-156).

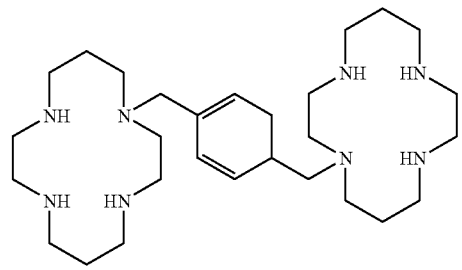

AMD3100

It has not been reported whether AMD3100 can efficiently block breast cancer metastasis, modulated via CXCR4. More importantly, a clinical study showed cardiac-related side effect of AMD3100 (Scozzafava, et al. (2002) *J Enzyme Inhib Med Chem* 17: 69-7641). In fact, AMD3100, was recently withdrawn from the clinical trials due in part to a cardiac-related side effect (Hendrix, et al. (2004) *Journal of Acquired Immune Deficiency Syndromes* 37(2)). The latter was not a result of the compound's ability to block CXCR4 function, but due to its presumed structural capacity for encapsulating metals.

Other nitrogen containing bicyclic molecules have been developed as CXCR4 antagonists. European Patent Publication No. 1 431 290 and PCT Publication No. WO 02/094261 to Kureha Chemical Industry Co., Ltd cover CXCR4 inhibitors that are potentially useful in treating various diseases including cancer metastatic disease and HIV infection.

U.S. Patent Publication No. 2004/0254221 to Yamazaki, et al. also provides compounds and use thereof to treat various diseases including cancer metastasis and HIV infection that are CXCR4 antagonists. The compounds are of the general formula:

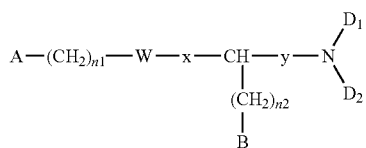

in which A is $A_1$-$G_1$-N($R_1$)—; $A_1$ is hydrogen or an optionally substituted, mono- or polycyclic, heteroaromatic or aromatic ring; $G_1$ is a single bond or —C($R_2$)($R_3$)—; $R_1$, $R_2$, and $R_3$ can be optionally substituted hydrocarbon groups; W is an optionally substituted hydrocarbon or heterocyclic ring; x is —C(=O)NH—; y is —C(=O)—; and $D_1$ is hydrogen atom, alkyl with a polycyclic aromatic ring, or amine.

PCT Publication No. WO 00/56729 and U.S. Pat. No. 6,750,348 to AnorMED and describe certain heterocyclic small molecule CXCR4 binding compounds, teaching that these are useful for the treatment of HIV infection, tumerogenesis, psoriasis or allergy. The compounds are of the general formula:

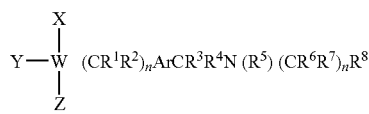

in which W can be a nitrogen or carbon atom; Y is absent or is hydrogen; $R^1$ to $R^7$ can be hydrogen or straight, branched or cyclic $C_{1-6}$ alkyl; $R^8$ is a substituted heterocyclic or aromatic group; Ar is an aromatic or heteroaromatic ring; and X is specified ring structure.

PCT Publication No. WO 2004/091518 to AnorMED also describes certain substituted nitrogen containing compounds that bind to CXCR4 receptors. The compounds are described as having the effect of increasing progenitor cells and/or stem cells, enhancing production of white blood cells, and exhibiting antiviral properties. PCT Publication No. WO 2004/093817 to AnorMED also discloses substituted heterocyclic CXCR4 antagonists which are described as useful to alleviate inflammatory conditions and elevate progenitor cells, as well as white blood cell counts. Similarly, PCT Publication No. WO 2004/106493 to AnorMED describes heterocyclic compounds that bind to CXCR4 and CCR5 receptors consisting of a core nitrogen atom surrounded by three pendant groups, wherein two of the three pendant groups are preferably benzimidazolyl methyl and tetrahydroquinolyl, and the third pendant group contains nitrogen and optionally contains additional rings. The compounds demonstrate protective effects against infections of target cells by a human immunodeficiency virus (HIV).

PCT Publication Nos. WO 2006/074426 and WO 2006/074428, both filed Jan. 9, 2006, describe certain compounds for the treatment of medical disorders mediated by CXCR4, including HIV infection and proliferative conditions. These compounds include two nitrogen linked cyclic substituents off a central aromatic or cyclic alkyl or heteroalkyl.

In light of the fact that the CXCR4 receptor is implicated in metastatic signaling as well as a number of other pathogenic conditions, it is important to identify new effective receptor antagonists.

It is therefore an object of the invention to provide new compounds, methods and compositions that inhibit CXCR4 receptor signaling.

It is another object of the invention to provide new compounds, methods and compositions that bind to the CXCR4 receptor and interfere with binding to its native ligand.

It is a more specific object of the invention to provide new compound, methods and compositions for treatment of proliferative disorders, and in particular, for the inhibition of cancer metastases.

It is another specific object of the invention to provide new compounds, methods and compositions for the treatment of viral infection, notably HIV.

SUMMARY OF THE INVENTION

Compounds, methods and pharmaceutical compositions for the treatment or prevention of diseases associated with pathogenic or undesired CXCR4 receptor activity and/or signaling are provided. Certain compounds provided herein interfere with the binding of the native SDF-1 ligand to the CXCR4 receptor and inhibit activation of the receptor and subsequent downstream signaling pathways. Based on this pathway, the invention provides compounds, methods and pharmaceutical compositions for the treatment of pathogenic conditions, including hyperproliferative diseases and viral diseases. In a particular aspect, the invention provides compounds, methods and pharmaceutical compositions for the reduction of cell migration and differentiation associated with cancer metastasis, modulated via CXCR4.

In another particular aspect, the invention provides compounds, methods and pharmaceutical compositions for treatment of HIV infection and for the reduction of cell invasion by the virus. These compounds may interfere with the binding of the CXCR4 receptor on the virus. The compounds, methods and compositions include an effective treatment amount of a compound of Formulas (I)-(V) as described herein, or a pharmaceutically acceptable salt, ester or prodrug thereof.

In a first principal embodiment, a method, compound and pharmaceutical composition for the treatment or prevention of a disorder associated with CXCR4 receptor activation, and particularly a proliferative disorder, including cancer metastasis, modulated via CXCR4 is provided that includes a compound of Formulas (I)-(V), or a pharmaceutically acceptable salt, ester or prodrug thereof.

The compounds of the invention are particularly useful for inhibiting CXCR4 receptor interactions with native ligands. In one embodiment, a method is provided to inhibit CXCR4-mediated disorders by contacting a cell with a compound of Formula (I)-(V), or a pharmaceutically acceptable salt, ester or prodrug thereof.

In one embodiment, a method of preventing metastases of a malignant cell is provided that includes administering a compound of Formula (I)-(V) to a host. The malignant cell can be a tumor cell. In certain embodiments, the compound can be provided to a host before treatment of a tumor with a second active compound. In a separate embodiment, the compound is provided to a patient that has been treated for cancer to reduce the likelihood of recurrence, or reduce mortality associated with a particular tumor. The compound of Formula (I)-(V) can also be provided in conjunction with another active compound.

In a separate embodiment, a method of treating disorders mediated by CXCR4, including metastasis, by administering a compound of Formulas (I)-(V) to a host in need of treatment is provided. In certain embodiments, the proliferative disorder is cancer, and in particular subembodiments, the disorder is a metastatic cancer. The compounds of the invention can be administered to a host in need thereof to reduce the incidence of metastasis. In particular embodiments, the disease is breast, brain, pancreatic, ovarian, particularly an ovarian epithelial, prostate, kidney, or non-small cell lung cancer. In a subembodiment, the compound is administered in combination or alternation with another active compound.

In another embodiment, the invention provides a method of reducing neovascularization, particularly VEGF-dependent neocascularization, by contacting a cell with a compound described herein. The cell can be in a host animal, including a human.

In another embodiment, pharmaceutical compositions including at least one compound of Formulas (I)-(V) are provided. In certain embodiments, at least a second active compound is included in the composition. The second active compound can be a chemotherapeutic, particularly an agent active against a primary tumor.

In one embodiment, a compound of Formula (I)-(V) is used to stimulate the production, proliferation and isolation of stem cells and progenitor cells bearing a CXCR4 reeceptors. Such cells include but are not limited to bone marrow progenitor and/or stem cells or progenitor cells for cardiac tissue.

In a separate embodiment, a method for treating diseases of vasculature, inflammatory and degenerative diseases is provided including administering a compound of Formula (I)-(V) to a host.

In a separate embodiment, a process for screening potential drug candidates is provided. The process includes providing a labeled peptide-based CXCR4 antagonist that has a detectable signal when bound to a CXCR4 receptor; contacting a CXCR4 receptor with at least one test molecule at a known concentration to form a test sample; contacting the test sample with the peptide-based antagonist; separately, contacting the peptide-based antagonist to a sample not including any test molecule to form a control sample; and comparing the signal from the test sample to the signal from the control sample. In a specific sub-embodiment, the peptide-based antagonist is derived from TN14003 (described in PCT Publication No. WO 04/087068 to Emory University). In a further subembodiment, the antagonist is labeled with a biotin molecule and the signal is elicited when the biotin-labeled antagonist is contacted with a streptavadin-conjugated signal molecule.

In one embodiment, a method, compound and pharmaceutical composition for the treatment or prevention of HIV infection, or for reduction of symptoms associated with AIDS, in a host in need thereof is provided including a compound of Formula (I)-(V), or a pharmaceutically acceptable salt, ester or prodrug thereof.

In one embodiment, a method of treating or preventing HIV infection, or of reducing symptoms associated with AIDS is provided including administering a compound of Formula (I)-(V) to a host. The compounds of the invention can be administered to a host in need thereof to reduce the incidence of recurrence of infection. In certain embodiments, the compound can be provided to a host in combination with treatment of the infection with a second active compound. In a separate embodiment, the compound is provided to a patient that has been treated for viral infection to keep viral load low, or reduce mortality associated with a particular infection, for example by reducing progression of AIDS related symptoms. The compound of Formula (I)-(V) can also be provided in conjunction with another active compound.

In another embodiment, the invention provides a method of treating a host infected with other infections associated with CXCR4 receptor activation, for example, liver diseases associated with flavivirus or pestivirus infection, and in particular, HCV or HBV, by administering an effective amount of a compound described herein. The cell can be in a host animal, including a human.

In another embodiment, pharmaceutical compositions including at least one compound of Formulas (I)-(V) are provided. In certain embodiments, at least a second active compound is administered to the host to achieve combination therapy. The second active compound can be another antiviral agent.

BRIEF DESCRIPTION OF THE DRAWINGS

The file of this patent contains at least one drawing executed in color. Copies of this patent with color drawings will be provided by the Patent Office upon request and payment of the necessary fee.

DETAILED DESCRIPTION OF THE INVENTION

Figure 1:
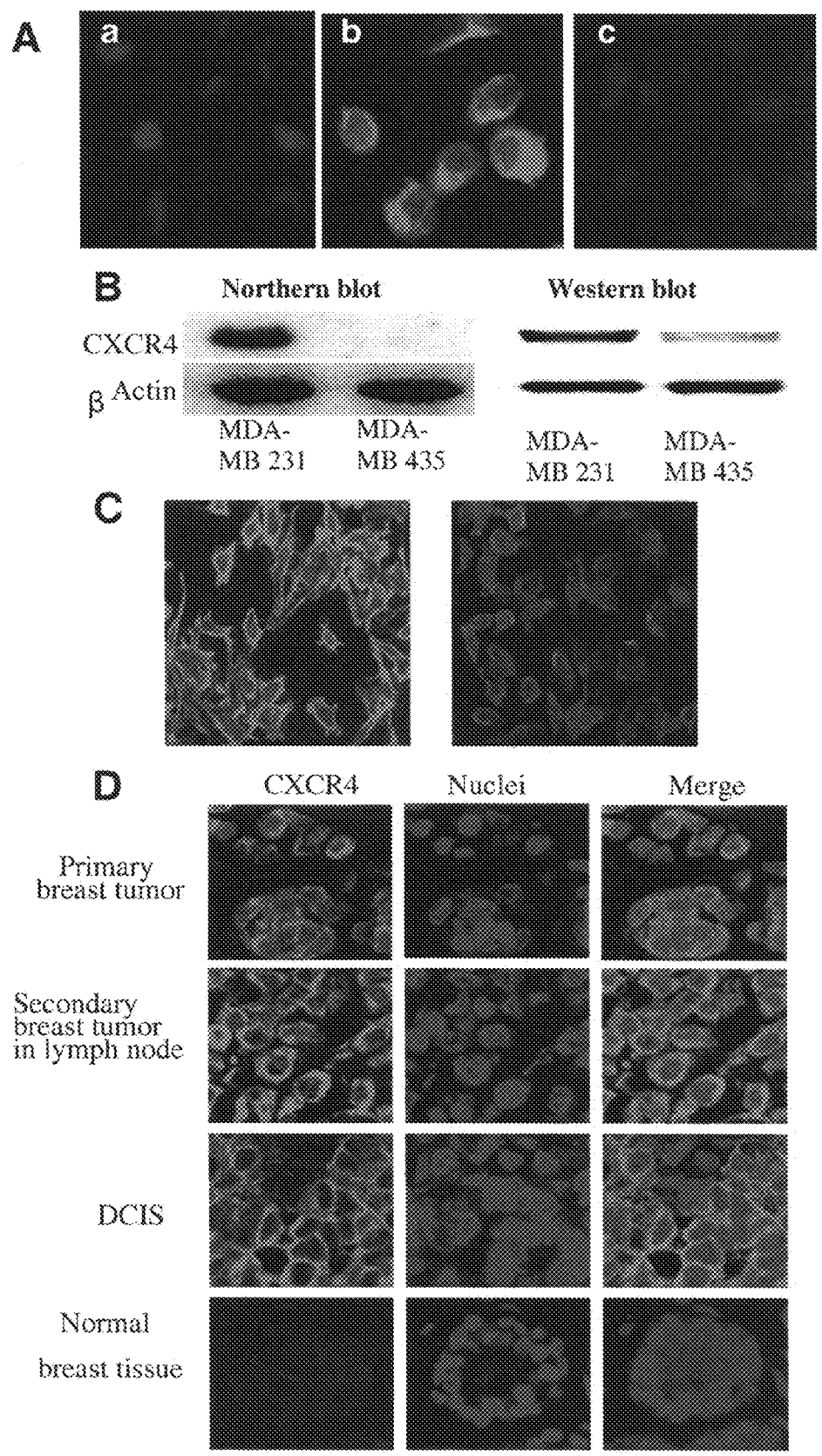
FIG. 1 shows images of stained cells and blots indicating the specificity of TN14003. A: The binding of TN14003 to CXCR4 was blocked by preincubation of 400 ng/ml SDF-1. Cells were immunostained by using biotin-labeled control peptide (a) or biotin-labeled TN14003 (b & c) and streptavidin-conjugated rhodamine (red). Cells were preincubated with SDF-1 for 10 min and then fixed in ice-cold acetone (c). B: Northern blot analysis and western blot analysis results show the different expression levels of CXCR4 from breast cancer cell lines, MDA-MB-231 and MDA-MB-435. β-actin was used as a loading control for both. C: Confocal micrographs of CXCR4 protein on cell's surface from MDA-MB-231 and MDA-MB-435 cell lines by using biotinylated TN14003 and streptavidin-conjugated R-PE (red color). Nuclei were counter-stained by cytox blue. D: Representative immunofluorescence staining of CXCR4 with the biotinylated TN14003 on paraffin embedded tissue sections of breast cancer patients and normal breast tissue.

Compounds, methods and compositions are provided that modulate the effect of the CXCR4 receptor. These compounds can be used to treat tumor metastsis or any other disease, particularly hyperproliferative diseases, involving CXCR4. These compounds can also be used to treat or prevent HIV infection, reduce viral load or alleviate progression towards the symptoms of AIDS in a host in need thereof.

Compounds described herein have the capacity to interact with and potentially inhibit CXCR4 receptor activation. Exemplary compounds have increased bioavailability and efficacy in inhibiting CXCR4 receptors and SDF-1-dependent signaling over known CXCR4 antagonists. Although not to be bound by theory, these compounds may inhibit metastasis through their capacity to inhibit SDF-1-CXCR4 interactions, which can decrease cell targeting, and may also reduce VEGF-dependent endothelial cell morphogenesis and angiogenesis. This endothelial cell growth is a key event in metastases of tumors.

Active Compound, and Physiologically Acceptable Salts and Prodrugs Thereof

In a first principal embodiment, a compound of Formula I, or a pharmaceutically acceptable salt, ester or prodrug thereof, is provided for the treatment or prevention of a disorder associated with CXCR4 receptor activation, and particularly a proliferative disorder, or a viral infection, including cancer metastasis and HIV infection, modulated via CXCR4:

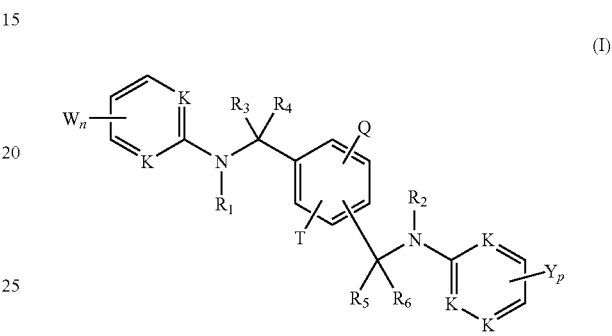

(I)

wherein:

each K is independently N, CH or CX where each X is independently selected from straight chain, branched or cyclic alkyl, heteroalkyl, haloalkyl, aralkyl, aryl, heteroaryl, F, Cl, Br, I, $NH_2$, NHR, $NR_2$, SR, $S_2R$, S—NHR, $S_2$—NHR, S—NRR', $S_2$—NRR', NHacyl, N(acyl)$_2$, $CO_2H$, $CO_2R$, CONRR', or CN;

each Q, T, W and Y are each independently H, R, acyl, F, Cl, Br, I, OH, OR, $NH_2$, NHR, $NR_2$, SR, SR, $S_2R$, S—NHR, $S_2$—NHR, S—NRR', $S_2$—NRR', NHacyl, N(acyl)$_2$, $CO_2H$, $CO_2R$, CONRR' or CN, where R and R' are independently selected from straight chain, branched or cyclic alkyl, alkenyl, alkynyl, heteroalkyl, haloalkyl or aralkyl, aryl and heteroaryl;

n is 0, 1, 2 or 3;

p is 0, 1 or 2;

$R^1$, $R^2$, $R^3$, $R^4$, $R^5$ and $R^6$ are independently selected from H, straight chain, branched or cyclic alkyl, alkenyl, alkynyl, aralkyl, aryl heteroaryl, acyl (RC—) and imidoyl (RC(NH)— or RC(NR')—) groups.

In another embodiment, a compound of Formula I, or a pharmaceutically acceptable salt, ester or prodrug thereof, is provided for the treatment or prevention of a proliferative disorder, for example metastatic cancer.

In another embodiment, a compound of Formula I, or a pharmaceutically acceptable salt, ester or prodrug thereof, is provided for the treatment or prevention of a HIV infection, or of reducing symptoms associated with AIDS.

In one subembodiment of Formula I, each K is independently CH or N. In one embodiment, one K is N. In another embodiment, at least two K are N. In yet another embodiment, at least three K are N, in another embodiment, four K are N and in yet another embodiment, five K are N.

In one embodiment, the compound is of the formula I-a, I-b or I-c:

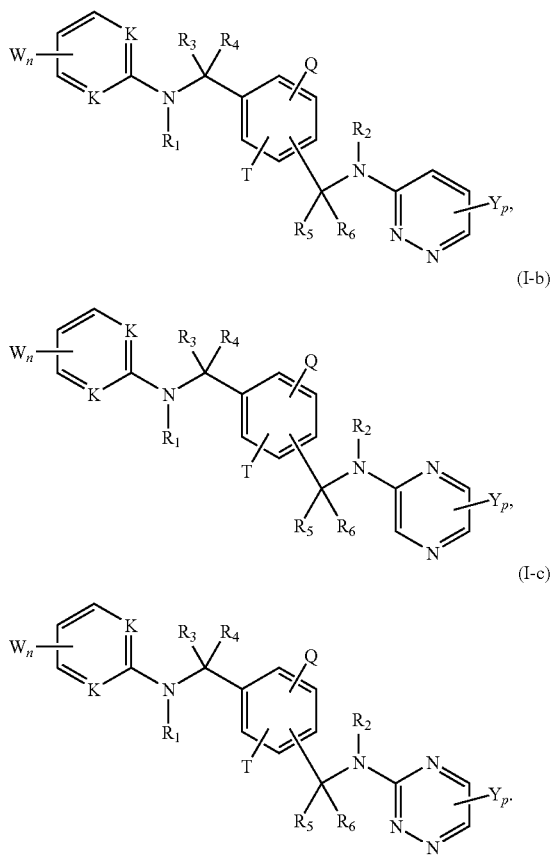

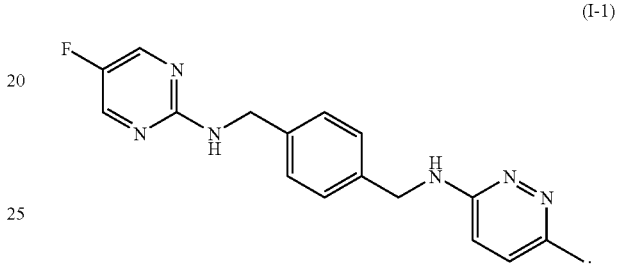

In a subembodiment of formula I, Y is H. In another subembodiment of formula I, Y is straight chained, branched or cyclic alkyl, heteroalkyl or haloalkyl. In one subembodiment of formula I, Y is straight chained or branched alkyl. In another subembodiment of formula I, Y is F, Cl, Br, or I. In yet another subembodiment of formula I, Y is $NH_2$, NHR or $NR_2$. In one subembodiment of formula I, Y is acyl. In another subembodiment of formula I, Y' is F, Cl, Br, or I. In yet another subembodiments of formula I, Y is $NH_2$, NHR or $NR_2$. In a specific embodiment of formula I, Y is OR. In certain embodiments, at least one Y is $NR_2$ and another Y is OR or H. In certain embodiments, R is heteroalkyl and in specific embodiments, the heteroatom is O or N. In certain subembodiments, Y is CONRR'.

In one embodiment, W is a halogen, including F, Cl, Br and I, or R. In certain embodiments, W is a halogen and Y is a straight chained, branched or cyclic alkyl, heteroalkyl or haloalkyl. In one subembodiment of formula I, at least one of W and Y is a halogen, including F, Cl, Br, I, or R. In another embodiment, both W and Y are a halogen. In a specific embodiment, at least one of W and Y is F and in yet another embodiment, both W and Y are F.

In another embodiment, W is a halogen, including F, Cl, Br and I, or R and Y is NHR, $NR_2$, NHacyl, $N(acyl)_2$, and in certain subembodiments, R is selected from straight chain, branched or cyclic alkyl, heteroalkyl, haloalkyl or aralkyl groups. In yet another embodiment, W is a halogen, including F, Cl, Br and I, or R and Y is SR, SR, $S_2R$, S—NHR, $S_2$—NHR, S—NRR' or $S_2$—NRR', and in certain subembodiments, R and R' are selected from straight chain, branched or cyclic alkyl, heteroalkyl, haloalkyl or aralkyl groups. In other embodiments, W is a halogen, including F, Cl, Br and I, or R and Y is H, acyl, F, Cl, Br, I, OH, OR, $NH_2$, $CO_2H$, $CO_2R$ or CN. In certain subembodiments, Y can be R.

In certain subembodiments, at least one of W or Y is R and R can be F or haloalkyl, for example $CF_3$.

In a specific embodiment of formula I, $R^1$ and $R^2$ are each H or alkyl and in certain embodiments, are each H.

In a specific embodiment of formula I, $R^3$, $R^4$, $R^5$ and $R^6$ are each H or alkyl and in certain embodiments, at least two, at least three or all four are H.

In a specific embodiment, a compound, method and composition including a compound of structure I-1, or a pharmaceutically acceptable salt, ester or prodrug thereof, is provided:

(I-1)

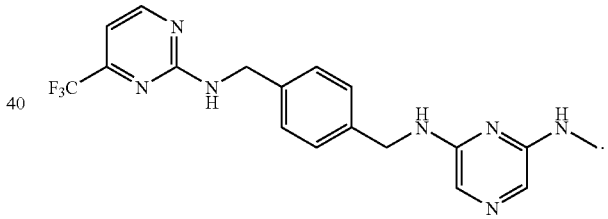

In a specific embodiment, a compound, method and composition including a compound of structure I-2, or a pharmaceutically acceptable salt, ester or prodrug thereof, is provided:

(I-2)

In a specific embodiment, a compound, method and composition including a compound of structure I-3, or a pharmaceutically acceptable salt, ester or prodrug thereof, is provided:

(I-3)

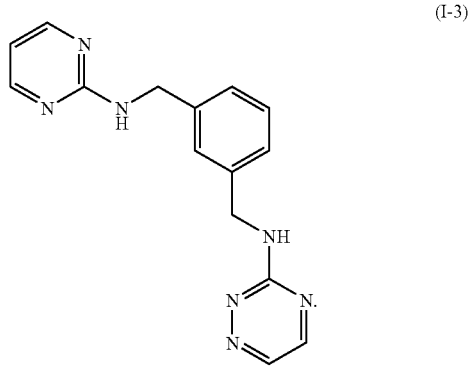

In a second principal embodiment, a compound of Formula II, or a pharmaceutically acceptable salt, ester or prodrug thereof, is provided for the treatment or prevention of a disorder associated with CXCR4 receptor activation, and particularly a proliferative disorder, or a viral infection, including cancer metastasis and HIV infection, modulated via CXCR4:

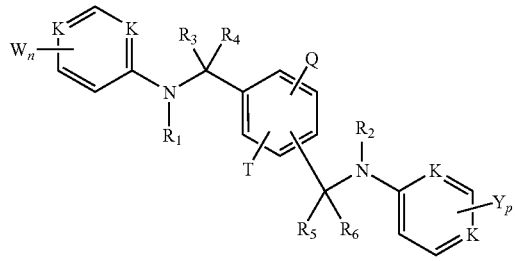

wherein:

each K is independently N, CH or CX where each X is independently selected from straight chain, branched or cyclic alkyl, heteroalkyl, haloalkyl, aralkyl, aryl, heteroaryl, F, Cl, Br, I, $NH_2$, NHR, $NR_2$, SR, $S_2R$, S—NHR, $S_2$—NHR, S—NRR', $S_2$—NRR', NHacyl, $N(acyl)_2$, $CO_2H$, $CO_2R$, CONRR', or CN;

each Q, T, W and Y are each independently H, R, acyl, F, Cl, Br, I, OH, OR, $NH_2$, NHR, $NR_2$, SR, SR, $S_2R$, S—NHR, $S_2$—NHR, S—NRR', $S_2$—NRR', NHacyl, $N(acyl)_2$, $CO_2H$, $CO_2R$, CONRR' or CN, where R and R' are independently selected from straight chain, branched or cyclic alkyl, alkenyl, alkynyl, heteroalkyl, haloalkyl, aralkyl, aryl and heteroaryl;

n is 0, 1, 2 or 3;

p is 0, 1, 2 or 3;

$R^1$, $R^2$, $R^3$, $R^4$, $R^5$ and $R^6$ are independently selected from H, straight chain, branched or cyclic alkyl, alkenyl, alkynyl, aralkyl, aryl heteroaryl, acyl (RC—) and imidoyl (RC(NH)— or RC(NR')—) groups;

wherein formula II does not include

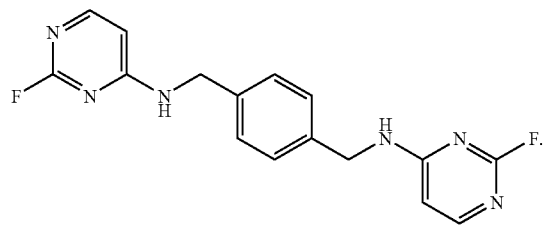

In another embodiment, a compound of Formula II, or a pharmaceutically acceptable salt, ester or prodrug thereof, is provided for the treatment or prevention of a proliferative disorder, for example metastatic cancer.

In another embodiment, a compound of Formula II, or a pharmaceutically acceptable salt, ester or prodrug thereof, is provided for the treatment or prevention of a HIV infection, or of reducing symptoms associated with AIDS.

In one subembodiment of formula II, each K is independently CH or N. In one embodiment, one K is N. In another embodiment, at least two K are N. In yet another embodiment, at least three K are N and in another embodiment, four K are N.

In a subembodiment of formula II, Y is H. In another subembodiment of formula II, Y is straight chained, branched or cyclic alkyl, heteroalkyl or haloalkyl. In one subembodiment of formula II, Y is straight chained or branched alkyl. In another subembodiment of formula II, Y is F, Cl, Br, or I. In yet another subembodiments of formula II, Y is $NH_2$, NHR or $NR_2$. In a specific embodiment of formula II, Y is $NR_2$. In one embodiment, Y is CONRR'.

In one embodiment, W is a halogen, including F, Cl, Br and I, or R. In certain embodiments, W is a halogen and Y is a straight chained, branched or cyclic alkyl, heteroalkyl or haloalkyl. In one subembodiment of formula II, at least one of W and Y is a halogen, including F, Cl, Br, I, or R. In another embodiment, both W and Y are a halogen. In a specific embodiment, at least one of W and Y is F and in yet another embodiment, both W and Y are F.

In another embodiment, W is a halogen, including F, Cl, Br and I, or R and Y is NHR, $NR_2$, NHacyl, $N(acyl)_2$, and in certain subembodiments, R is selected from straight chain, branched or cyclic alkyl, heteroalkyl, haloalkyl or aralkyl groups. In yet another embodiment, W is a halogen, including F, Cl, Br and I, or R and Y is SR, SR, $S_2R$, S—NHR, $S_2$—NHR, S—NRR' or $S_2$—NRR', and in certain subembodiments, R and R' are selected from straight chain, branched or cyclic alkyl, heteroalkyl, haloalkyl or aralkyl groups. In other embodiments, W is a halogen, including F, Cl, Br and I, or R and Y is H, acyl, F, Cl, Br, I, OH, OR, $NH_2$, $CO_2H$, $CO_2R$ or CN. In certain subembodiments, Y can be R.

In certain subembodiments, at least one of W or Y is R and R can be F or haloalkyl, for example $CF_3$.

In a specific embodiment of formula II, $R^1$ and $R^2$ are each H or alkyl and in certain embodiments, are each H.

In a specific embodiment of formula II, $R^3$, $R^4$, $R^5$ and $R^6$ are each H or alkyl and in certain embodiments, at least two, at least three or all four are H.

In a specific embodiment, a compound, method and composition including a compound of formula II-1, or a pharmaceutically acceptable salt, ester or prodrug thereof, is provided:

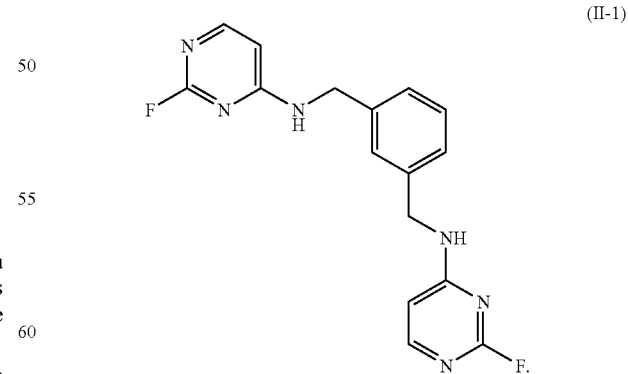

In a specific embodiment, a compound, method and composition including a compound of formula II-2, or a pharmaceutically acceptable salt, ester or prodrug thereof, is provided:

(II-2)

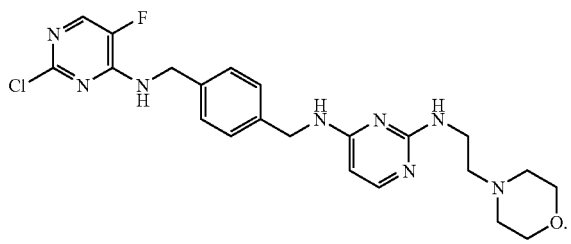

In a third principal embodiment, a compound of Formula III, or a pharmaceutically acceptable salt, ester or prodrug thereof, is provided for the treatment or prevention of a disorder associated with CXCR4 receptor activation, and particularly a proliferative disorder, or a viral infection, including cancer metastasis and HIV infection, modulated via CXCR4:

(III)

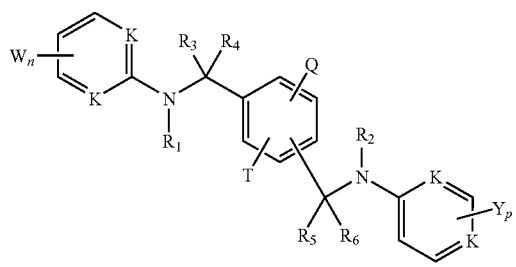

wherein:
each K is independently N, CH or CX where each X is independently selected from straight chain, branched or cyclic alkyl, heteroalkyl, haloalkyl, aralkyl, aryl, heteroaryl, F, Cl, Br, I, $NH_2$, NHR, $NR_2$, SR, $S_2R$, S—NHR, $S_2$—NHR, S—NRR', $S_2$—NRR', NHacyl, $N(acyl)_2$, $CO_2H$, $CO_2R$, CONRR', or CN;

each Q, T, W and Y are each independently H, R, acyl, F, Cl, Br, I, OH, OR, $NH_2$, NHR, $NR_2$, SR, SR, $S_2R$, S—NHR, $S_2$—NHR, S—NRR', $S_2$—NRR', NHacyl, $N(acyl)_2$, $CO_2H$, $CO_2R$, CONRR' or CN, where R and R' are independently selected from straight chain, branched or cyclic alkyl, alkenyl, alkynyl, heteroalkyl, haloalkyl, aralkyl, aryl and heteroaryl;

n is 0, 1, 2 or 3;

p is 0, 1, 2 or 3;

$R^1$, $R^2$, $R^3$, $R^4$, $R^5$ and $R^6$ are each independently selected from H, straight chain, branched or cyclic alkyl, alkenyl, alkynyl, aralkyl, aryl heteroaryl, acyl (RC—) and imidoyl (RC(NH)— or RC(NR')—) groups.

In another embodiment, a compound of Formula III, or a pharmaceutically acceptable salt, ester or prodrug thereof, is provided for the treatment or prevention of a proliferative disorder, for example metastatic cancer.

In another embodiment, a compound of Formula III, or a pharmaceutically acceptable salt, ester or prodrug thereof, is provided for the treatment or prevention of a HIV infection, or of reducing symptoms associated with AIDS.

In one subembodiment of formula III, each K is independently CH or N. In one embodiment, one K is N. In another embodiment, at least two K are N. In yet another embodiment, at least three K are N and in another embodiment, four K are N.

In a subembodiment of formula III, at least one Y is H. In another subembodiment of formula III, at least one Y is straight chained, branched or cyclic alkyl, heteroalkyl or haloalkyl. In one subembodiment of formula III, Y is straight chained or branched alkyl. In another subembodiment of formula III, at least one Y is F, Cl, Br, or I. In yet another subembodiment of formula III, at least one Y is $NH_2$, NHR or $NR_2$. In a specific embodiment of formula III, at least one Y is $NR_2$.

In one embodiment, at least one W is a halogen, including F, Cl, Br and I, or R. In certain embodiments, at least one W is a halogen, and at least one Y is a straight-chain, branched or cyclic alkyl, heteroalkyl or haloalkyl. In one subembodiment of formula III, at least one of W and Y is a halogen, including F, Cl, Br, I, or R. In another embodiment, at least one W and at least one Y are a halogen. In a specific embodiment, at least one of W and Y is F and in yet another embodiment, at least one W and at least one Y are F.

In another embodiment, at least one W is a halogen, including F, Cl, Br and I, or R and at least one Y is NHR, $NR_2$, NHacyl, $N(acyl)_2$, and in certain subembodiments, R is selected from straight chain, branched or cyclic alkyl, heteroalkyl, haloalkyl or aralkyl groups. In yet another embodiment, at least one W is a halogen, including F, Cl, Br and I, or R and at least one Y is SR, SR, $S_2R$, S—NHR, $S_2$—NHR, S—NRR' or $S_2$—NRR', and in certain subembodiments, R and R' are selected from straight chain, branched or cyclic alkyl, heteroalkyl, haloalkyl or aralkyl groups. In other embodiments, at least one of W and W' is a halogen, including F, Cl, Br and I, or R and at least one Y is H, acyl, F, Cl, Br, I, OH, OR, $NH_2$, $CO_2H$, $CO_2R$ or CN. In certain subembodiments, at least one Y is R.

In certain subembodiments, at least one of W and Y is R and R can be F or haloalkyl, for example $CF_3$.

In a specific embodiment of formula III, $R^1$ and $R^2$ are each H or alkyl and in certain embodiments, are each H.

In a specific embodiment of formula III, $R^3$, $R^4$, $R^5$ and $R^6$ are each H or alkyl and in certain embodiments, at least two, at least three or all four are H.

In a specific embodiment, a compound, method and composition including a compound of structure III-1, or a pharmaceutically acceptable salt, ester or prodrug thereof, is provided:

(III-1)

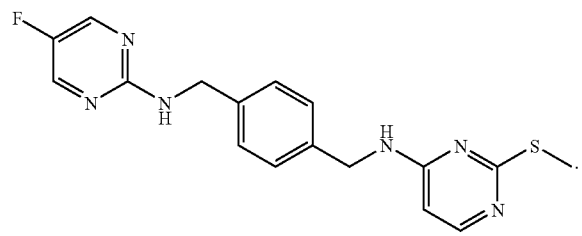

In a specific embodiment, a compound, method and composition including a compound of structure III-2, or a pharmaceutically acceptable salt, ester or prodrug thereof, is provided:

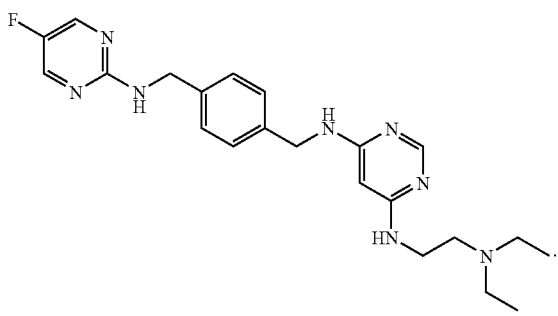

(III-2)

In a specific embodiment, a compound, method and composition including a compound of structure III-3, or a pharmaceutically acceptable salt, ester or prodrug thereof, is provided:

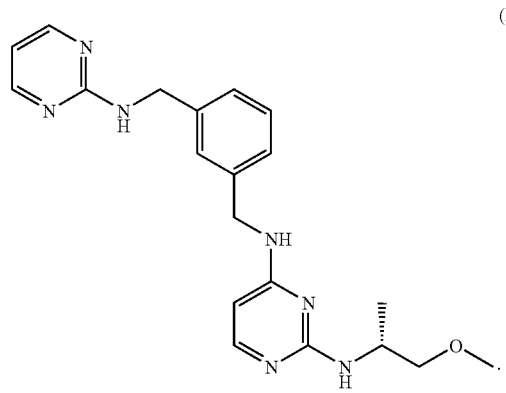

(III-3)

In a fourth principal embodiment, a compound of Formula IV, or a pharmaceutically acceptable salt, ester or prodrug thereof, is provided for the treatment or prevention of a disorder associated with CXCR4 receptor activation, and particularly a proliferative disorder, or a viral infection, including cancer metastasis and HIV infection, modulated via CXCR4:

(IV)

wherein:
each K is independently N, CH or CX where each X is independently selected from straight chain, branched or cyclic alkyl, heteroalkyl, haloalkyl, aralkyl, aryl, heteroaryl, F, Cl, Br, I, $NH_2$, NHR, $NR_2$, SR, $S_2R$, S—NHR, $S_2$—NHR, S—NRR', $S_2$—NRR', NHacyl, $N(acyl)_2$, $CO_2H$, $CO_2R$, CONRR', or CN;
each Q, T, W and Y are each independently H, R, acyl, F, Cl, Br, I, OH, OR, $NH_2$, NHR, $NR_2$, SR, SR, $S_2R$, S—NHR, $S_2$—NHR, S—NRR', $S_2$—NRR', NHacyl, $N(acyl)_2$, $CO_2H$, $CO_2R$, CONRR' or CN, where R and R' are independently selected from straight chain, branched or cyclic alkyl, alkenyl, alkynyl, heteroalkyl, haloalkyl, aralkyl, aryl and heteroaryl;

n is 0, 1 or 2;

p is 0, 1 or 2;

$R^1$, $R^2$, $R^3$, $R^4$, $R^5$ and $R^6$ are each independently selected from H, straight chain, branched or cyclic alkyl, alkenyl, alkynyl, aralkyl, aryl heteroaryl, acyl (RC—) and imidoyl (RC(NH)— or RC(NR')—) groups;

wherein the compounds of formula IV do not include

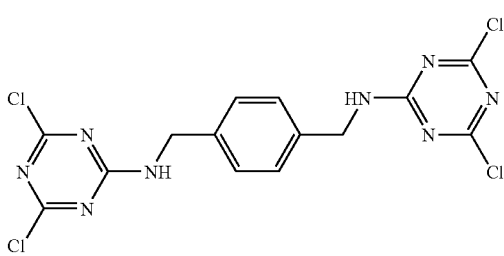

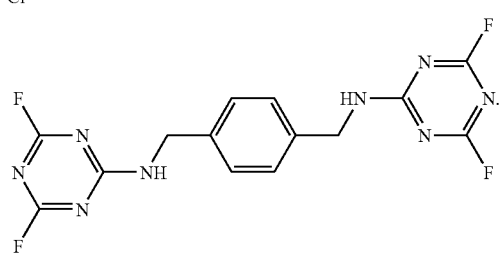

In another embodiment, a compound of Formula IV, or a pharmaceutically acceptable salt, ester or prodrug thereof, is provided for the treatment or prevention of a proliferative disorder, for example metastatic cancer.

In another embodiment, a compound of Formula IV, or a pharmaceutically acceptable salt, ester or prodrug thereof, is provided for the treatment or prevention of a HIV infection, or of reducing symptoms associated with AIDS.

In one subembodiment of formula IV, each K is independently CH or N. In one embodiment, one K is N. In another embodiment, at least two K are N. In yet another embodiment, at least three K are N, in another embodiment, four K are N and in yet another embodiment, five K are N. In one embodiment, the compound is of the formula IV-a:

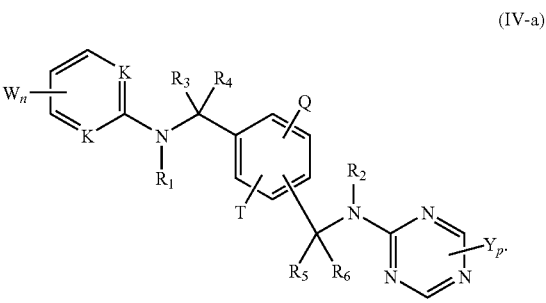

(IV-a)

In a subembodiment of formula IV, at least one Y is H. In another subembodiment of formula IV, at least one Y is straight chained, branched or cyclic alkyl, heteroalkyl or haloalkyl. In one subembodiment of formula IV, at least one Y is straight chained or branched alkyl. In another subembodiment of formula IV, at least one Y is F, Cl, Br, or I. In yet another subembodiments of formula IV, Y is $NH_2$, NHR or $NR_2$. In a specific embodiment of formula IV, Y is $NR_2$. In certain embodiments, one Y is $NR_2$ and another Y is OR or H. In certain embodiments, R is heteroalkyl and in specific embodiments, the heteroatom is O or N.

In one embodiment, at least one W is a halogen, including F, Cl, Br and I, or R. In certain embodiments, at least one W is a halogen and at least one Y is a straight chained, branched or cyclic alkyl, heteroalkyl or haloalkyl. In one subembodiment of formula IV, at least one of W and Y is a halogen, including F, Cl, Br, I, or R. In another embodiment, at least one W and at least one Y are a halogen. In a specific embodiment, at least one of W and Y is F and in yet another embodiment, at least one W and at least one Y are F.

In another embodiment, at least one W is a halogen, including F, Cl, Br and I, or R and Y is NHR, $NR_2$, NHacyl, $N(acyl)_2$, and in certain subembodiments, R is selected from straight chain, branched or cyclic alkyl, heteroalkyl, haloalkyl or aralkyl groups. In yet another embodiment, W at least one is a halogen, including F, Cl, Br and I, or R and Y is SR, SR, $S_2R$, S—NHR, $S_2$—NHR, S—NRR' or $S_2$—NRR', and in certain subembodiments, R and R' are selected from straight chain, branched or cyclic alkyl, heteroalkyl, haloalkyl or aralkyl groups. In other embodiments, at least one W is a halogen, including F, Cl, Br and I, or R and Y is H, acyl, F, Cl, Br, I, OH, OR, $NH_2$, $CO_2H$, $CO_2R$ or CN. In certain subembodiments, at least one Y is R.

In certain subembodiments, at least one W or Y is R and R can be F or haloalkyl, for example $CF_3$.

In a specific embodiment of formula IV, $R^1$ and $R^2$ are each H or alkyl and in certain embodiments, are each H.

In a specific embodiment of formula IV, $R^3$, $R^4$, $R^5$ and $R^6$ are each H or alkyl and in certain embodiments, at least two, at least three or all four are H.

In a specific embodiment, a compound, method and composition including a compound of structure IV-1, or a pharmaceutically acceptable salt, ester or prodrug thereof, is provided:

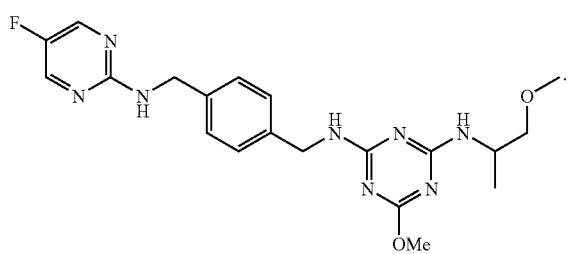

In a specific embodiment, a compound, method and composition including a compound of structure IV-2, or a pharmaceutically acceptable salt, ester or prodrug thereof, is provided:

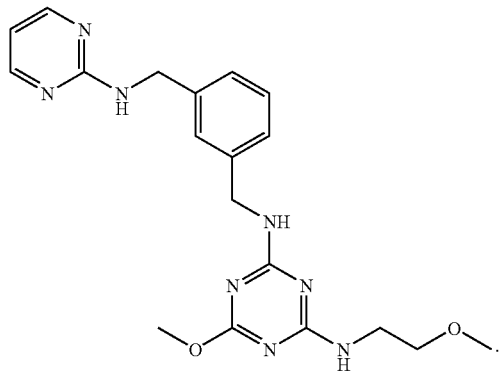

In a fifth principal embodiment, a compound of Formula V, or a pharmaceutically acceptable salt, ester or prodrug thereof, is provided for the treatment or prevention of a disorder associated with CXCR4 receptor activation, and particularly a proliferative disorder, or a viral infection, including cancer metastasis and HIV infection, modulated via CXCR4:

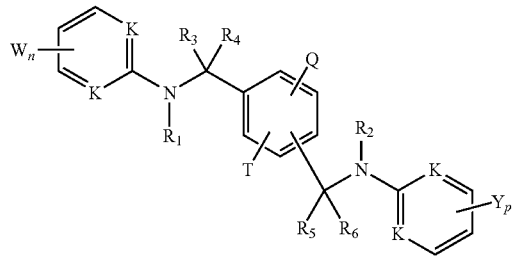

(V)

wherein:

each K is independently N, CH or CX where each X is independently selected from straight chain, branched or cyclic alkyl, heteroalkyl, haloalkyl, aralkyl, aryl, heteroaryl, F, Cl, Br, I, $NH_2$, NHR, $NR_2$, SR, $S_2R$, S—NHR, $S_2$—NHR, S—NRR', $S_2$—NRR', NHacyl, $N(acyl)_2$, $CO_2H$, $CO_2R$, CONRR', or CN;

each Q, T, W and Y are each independently H, R, acyl, F, Cl, Br, I, OH, OR, $NH_2$, NHR, $NR_2$, SR, SR, $S_2R$, S—NHR, $S_2$—NHR, S—NRR', $S_2$—NRR', NHacyl, $N(acyl)_2$, $CO_2H$, $CO_2R$, CONRR' or CN, where R and R' are independently selected from straight chain, branched or cyclic alkyl, alkenyl, alkynyl, heteroalkyl, haloalkyl, aralkyl, aryl and heteroaryl;

n is 0, 1, 2 or 3;

p is 0, 1, 2 or 3;

$R^1$, $R^2$, $R^3$, $R^4$, $R^5$ and $R^6$ are each independently selected from H, straight chain, branched or cyclic alkyl, alkenyl, alkynyl, aralkyl, aryl, heteroaryl, heterocycle, acyl (RC—) and imidoyl (RC(NH)— or RC(NR')—) groups;

and wherein the compounds of Formula V do not include:
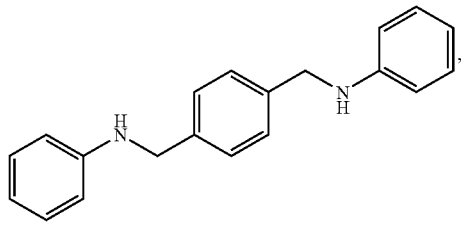
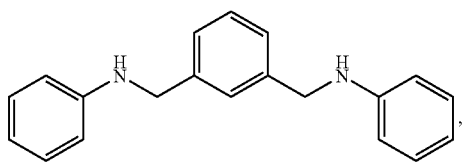
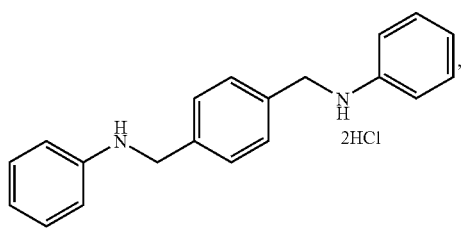
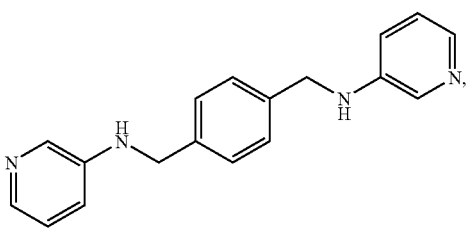
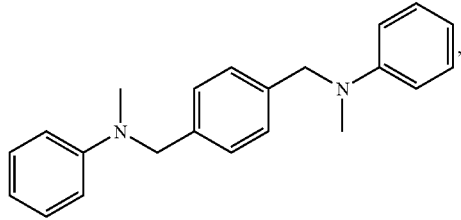
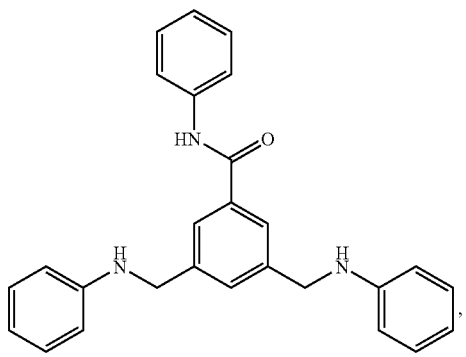
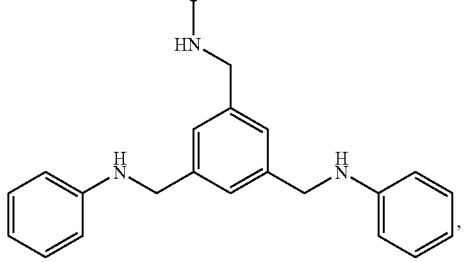
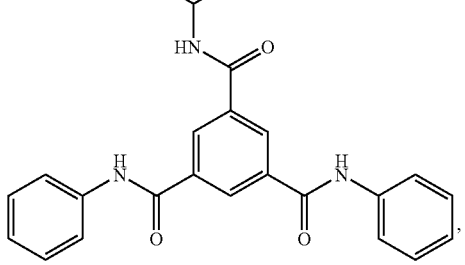
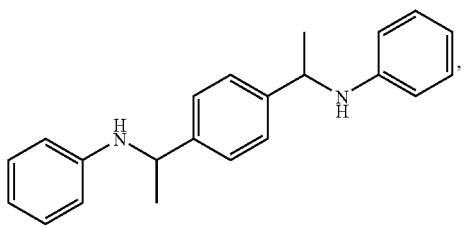
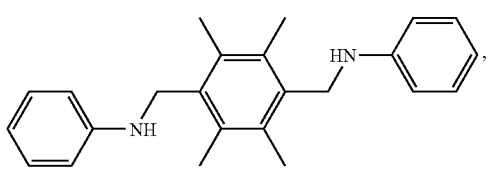
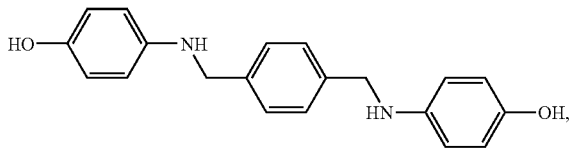
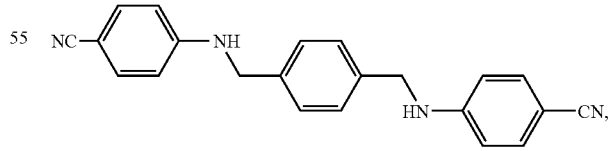
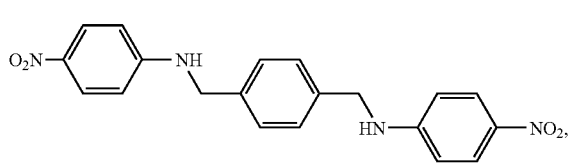

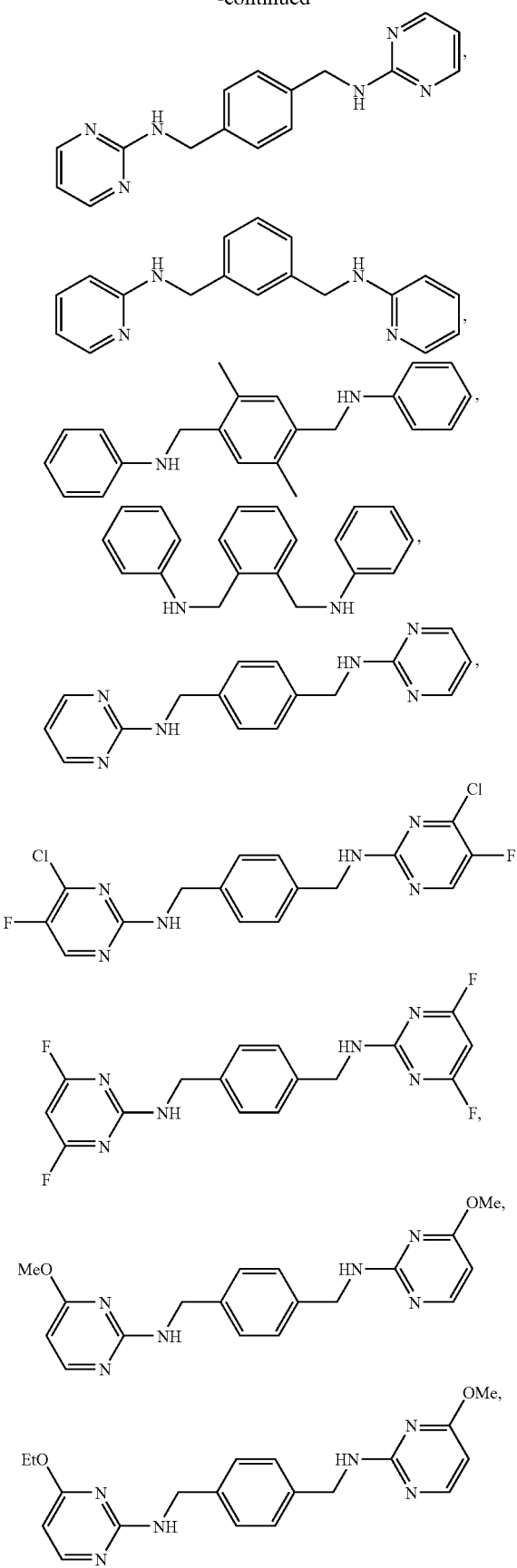
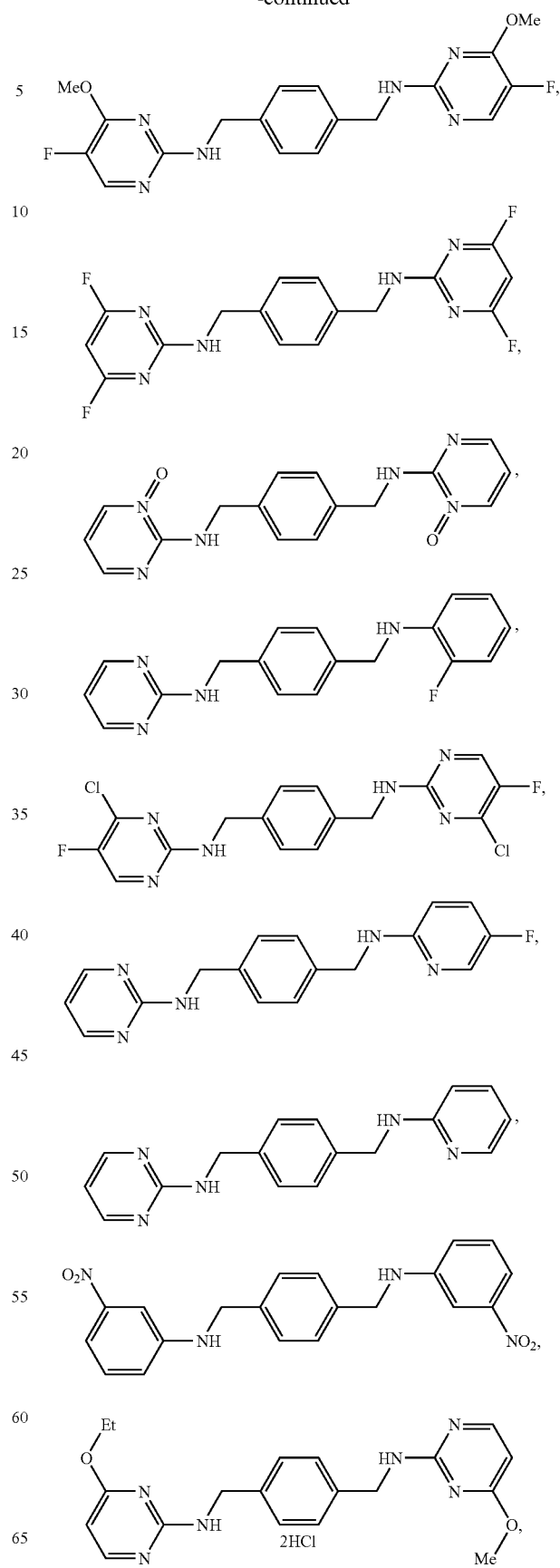

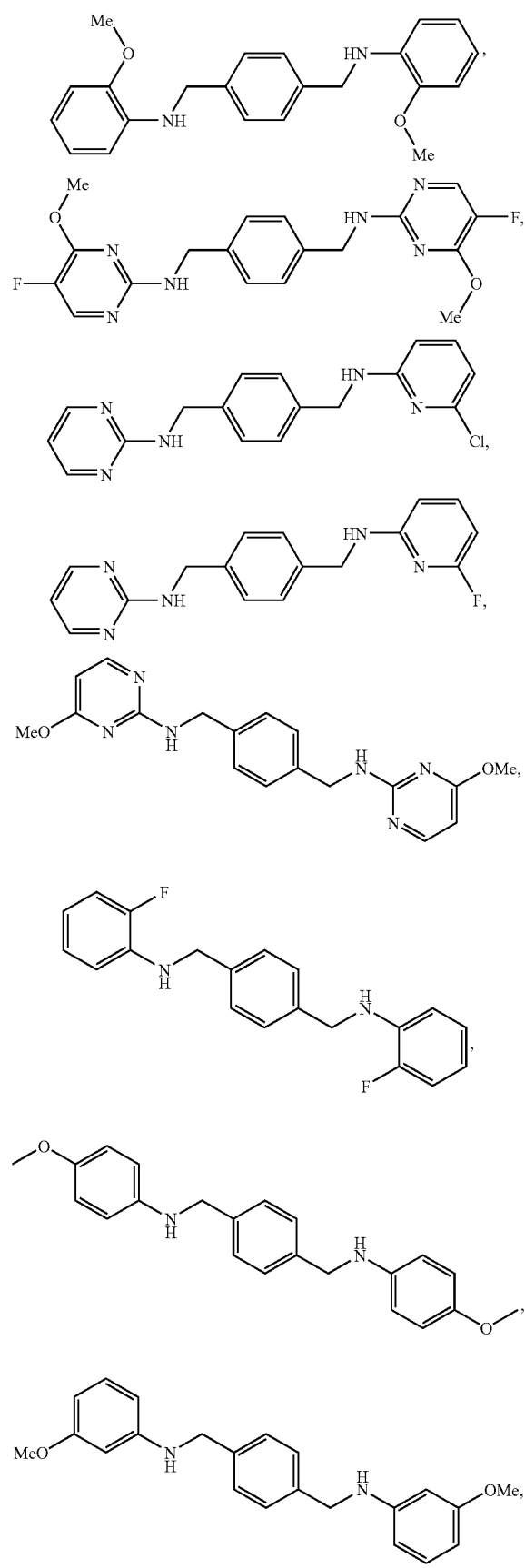
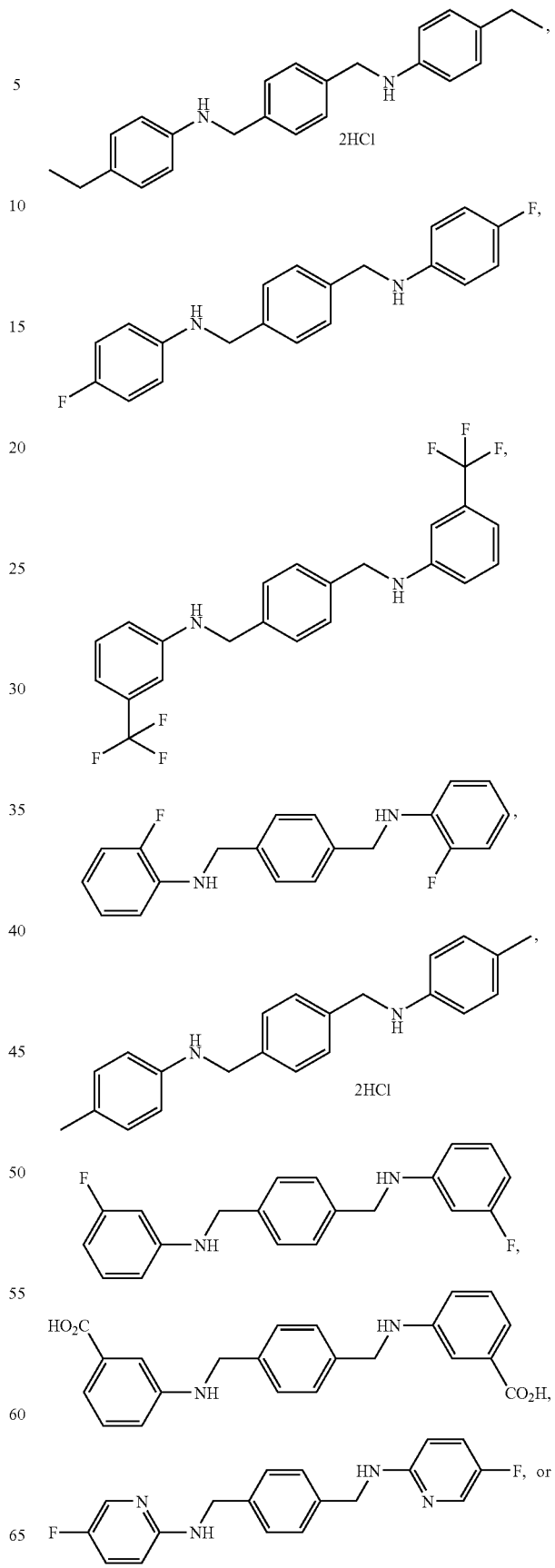

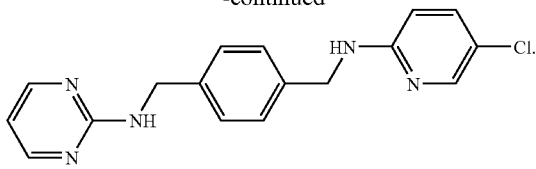

In another embodiment, a compound of Formula V, or a pharmaceutically acceptable salt, ester or prodrug thereof, is provided for the treatment or prevention of a proliferative disorder, for example metastatic cancer.

In another embodiment, a compound of Formula V, or a pharmaceutically acceptable salt, ester or prodrug thereof, is provided for the treatment or prevention of a HIV infection, or of reducing symptoms associated with AIDS.

In one subembodiment of formula V, each K is independently CH or N. In one embodiment, one K is N. In another embodiment, at least two K are N. In yet another embodiment, at least three K are N. In a particular embodiment, four K are N. In another embodiment, at least one K is CX. In a particular embodiment, four K are N.

In a subembodiment of formula V, Y is H. In another subembodiment of formula V, Y is straight chained, branched or cyclic alkyl, heteroalkyl or haloalkyl. In one subembodiment of formula V, Y is straight chained or branched alkyl. In one embodiment, Y is haloalkyl, for example $CF_3$. In another subembodiment of formula V, Y is F, Cl, Br, or I. In yet another subembodiments of formula V, Y is $NH_2$, NHR or $NR_2$. In a specific embodiment of formula V, Y is $NR_2$. In one embodiment, Y is CONRR'. In a specific embodiment, Y is C(O)-heterocycle, wherein the heterocycle may be unsubstituted or substituted by hydroxy, alkyl or alkoxyalkyl. In a particular embodiment, Y is

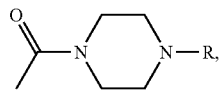

for example

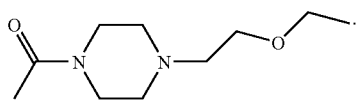

In another embodiment, Y is

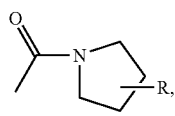

for example

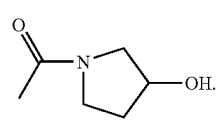

In one embodiment, n is 0. In another embodment, p is 0. In one embodiment, n is 1. In another embodment, p is 1. In one embodiment, n is 2. In another embodment, p is 2. In a particular embodiment, one Y is C(O)-heterocycle, wherein the heterocycle may be unsubstituted or substituted by hydroxy, alkyl or alkoxyalkyl, and another Y is haloalkyl. In a subembodiment, one Y is

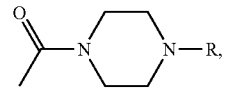

for example

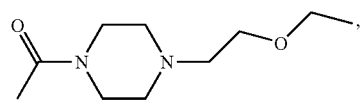

and another Y is haloalkyl, for example $CF_3$. In another subembodiment, one Y is

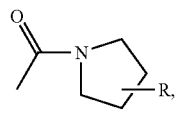

for example

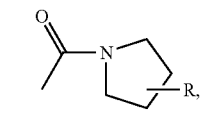

and another Y is haloalkyl, for example $CF_3$.

In one embodiment, W is H. In another embodiment, W is a halogen, including F, Cl, Br and I, or R. In certain embodiments, W is a halogen and Y is a straight chained, branched or cyclic alkyl, heteroalkyl or haloalkyl. In a particular embodiment, at least one W is halo, for example F or Cl, and at least one Y is a haloalkyl, for example $CF_3$.

In another embodiment, W is a halogen, including F, Cl, Br and I, or R and Y is NHR, $NR_2$, NHacyl, $N(acyl)_2$, and in certain subembodiments, R is selected from straight chain, branched or cyclic alkyl, heteroalkyl, haloalkyl or aralkyl groups. In yet another embodiment, W is a halogen, including F, Cl, Br and I, or R and Y is SR, SR, $S_2R$, S—NHR, $S_2$—NHR, S—NRR' or $S_2$—NRR', and in certain subembodiments, R and R' are selected from straight chain, branched or cyclic alkyl, heteroalkyl, haloalkyl or aralkyl groups. In other embodiments, W is a halogen, including F, Cl, Br and I, or R and Y is H, acyl, F, Cl, Br, I, OH, OR, $NH_2$, $CO_2H$, $CO_2R$ or CN. In certain subembodiments, Y can be R.

In certain subembodiments, at least one of W or Y is R and R can be F or haloalkyl, for example $CF_3$.

In a particular embodiment, W is H and at least one Y is not H. In another particular embodiment, Y is H and at least one W is not H.

In a specific embodiment of formula V, $R^1$ and $R^2$ are each independently H or alkyl. In another embodiment, $R^1$ and $R^2$ are each H.

In a specific embodiment of formula V, $R^3$, $R^4$, $R^5$ and $R^6$ are each independently H or alkyl. In another embodiment, at least two, at least three or all four of $R^3$, $R^4$, $R^5$ and $R^6$ are H.

In one subembodiment, a compound, method and composition of Formula V-1, or a pharmaceutically acceptable salt, ester or prodrug thereof, is provided:

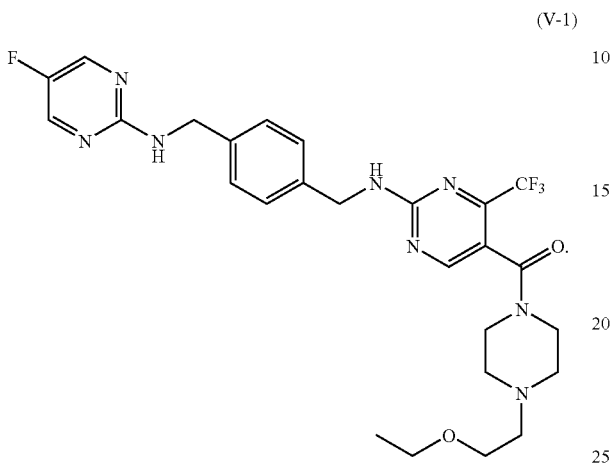

(V-1)

In one subembodiment, a compound, method and composition of Formula I-2, or a pharmaceutically acceptable salt, ester or prodrug thereof, is provided:

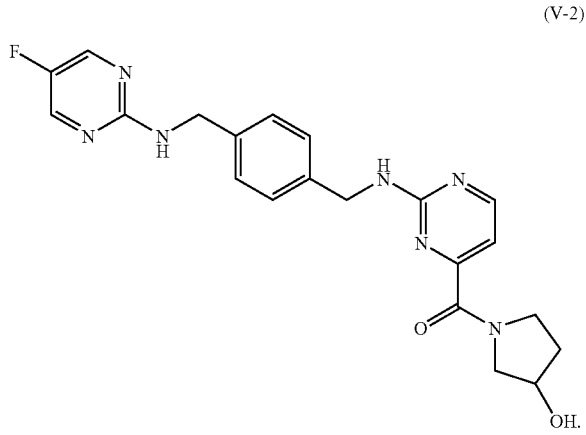

(V-2)

In one subembodiment, a compound, method and composition of Formula I-3, or a pharmaceutically acceptable salt, ester or prodrug thereof, is provided:

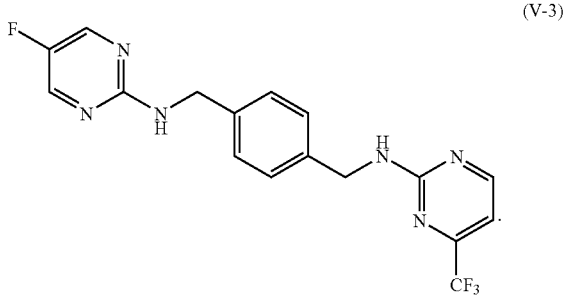

(V-3)

In one subembodiment, a compound, method and composition of Formula I-4, or a pharmaceutically acceptable salt, ester or prodrug thereof, is provided:

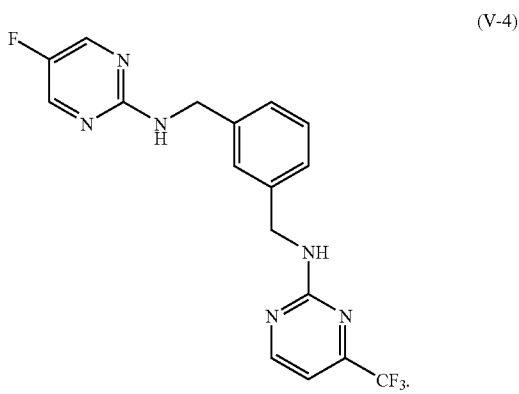

(V-4)

In one subembodiment of any of the foregoing formulae, $R^1$, $R^2$, $R^3$, $R^4$, $R^5$ and $R^6$ are each H, each K is N.

In one embodiment, the compound is a compound of Formula (I)-(V) or a compound wherein compounds wherein a 6-membered aromatic ring is substituted by two $CR_2$—NR-aryl or $CR_2$—NR-heteroaryl groups, and wherein the 6-membered aromatic ring, aryl or heteroaryl groups may be optionally substituted with Q, T, W and Y are each independently H, R, acyl, F, Cl, Br, I, OH, OR, $NH_2$, NHR, $NR_2$, SR, SR, $S_2R$, S—NHR, $S_2$—NHR, S—NRR', $S_2$—NRR', NHacyl, $N(acyl)_2$, $CO_2H$, $CO_2R$, CONRR' or CN, where R and R' are independently selected from straight chain, branched or cyclic alkyl, heteroalkyl, heterocycle, haloalkyl or aralkyl groups, aryl and heteroaryl.

In another particular embodiment, a method of preventing metastasis of a malignant cell is provided that includes contacting the cells with a compound of Formula (I)-(V) as described above, or a pharmaceutically acceptable salt, ester or prodrug thereof.

DEFINITIONS

The term "alkyl", as used herein, unless otherwise specified, refers to a saturated straight, branched, or cyclic, primary, secondary, or tertiary hydrocarbon of typically $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term optionally includes substituted alkyl groups. Moieties with which the alkyl group can be substituted are selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

Whenever any range is specified in the application, this range includes independently each and every element of the range. In one, non-limiting example, when the terms "$C_1$-$C_5$ alkyl", "$C_2$-$C_5$ alkenyl", "$C_1$-$C_5$ alkoxy", "$C_2$-$C_5$ alkenoxy", "$C_2$-$C_5$ alkynyl", and "$C_2$-$C_5$ alkynoxy" are used, these are considered to include, independently, each member of the group, such that, for example, $C_1$-$C_5$ alkyl includes straight, branched and where appropriate cyclic $C_1$, $C_2$, $C_3$, $C_4$ and $C_5$ alkyl functionalities; $C_2$-$C_5$ alkenyl includes straight, branched, and where appropriate cyclic $C_2$, $C_3$, $C_4$ and $C_5$ alkenyl functionalities; $C_1$-$C_5$ alkoxy includes straight, branched, and where appropriate cyclic $C_1$, $C_2$, $C_3$, $C_4$ and $C_5$ alkoxy functionalities; $C_2$-$C_5$ alkenoxy includes straight, branched, and where appropriate cyclic $C_2$, $C_3$, $C_4$ and $C_5$ alkenoxy functionalities; $C_2$-$C_5$ alkynyl includes straight, branched and where appropriate cyclic $C_1$, $C_2$, $C_3$, $C_4$ and $C_5$ alkynyl functionalities; and $C_2$-$C_5$ alkynoxy includes straight, branched, and where appropriate cyclic $C_2$, $C_3$, $C_4$ and $C_5$ alkynoxy functionalities.

The term "lower alkyl", as used herein, and unless otherwise specified, refers to a $C_1$ to $C_4$ saturated straight, branched, or if appropriate, a cyclic (for example, cyclopropyl) alkyl group, optionally including substituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term "alkenyl" means a monovalent, unbranched or branched hydrocarbon chain having one or more double bonds therein. The double bond of an alkenyl group can be unconjugated or conjugated to another unsaturated group. Suitable alkenyl groups include, but are not limited to ($C_2$-$C_8$)alkenyl groups, such as vinyl, allyl, butenyl, pentenyl, hexenyl, butadienyl, pentadienyl, hexadienyl, 2-ethylhexenyl, 2-propyl-2-butenyl, 4-(2-methyl-3-ethenyl)-pentenyl. An alkenyl group can be unsubstituted or substituted with one or more suitable substituents.

The term "alkynyl" means a monovalent, unbranched or branched hydrocarbon chain having one or more triple bonds therein. The double bond of an alkynyl group can be unconjugated or conjugated to another unsaturated group. Suitable alkenyl groups include, but are not limited to ($C_2$-$C_8$)alkynyl groups, such as ethynyl, propynyl, butyryl, pentynyl, hexynyl, 2-ethylhexynyl, 2-propyl-2-butyryl, 4-(2-methyl-3-ethynyl)-pentynyl. An alkynyl group can be unsubstituted or substituted with one or more suitable substituents.

The term "alkylamino" or "arylamino" refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term "aryl", as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term "alkaryl" or "alkylaryl" refers to an alkyl group with an aryl substituent. The term aralkyl or arylalkyl refers to an aryl group with an alkyl substituent.

The term "halo", as used herein, includes chloro, bromo, iodo, and fluoro.

The term "haloalkyl" refers an alkyl group which is substituted by at least one halo group, for example $CF_3$.

The term "acyl" refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The term "heteroalkyl" refers to an alkyl group substituted by a heteroatom functionality, for example aminoalkyl, alkoxyalkyl, thioalkyl. A heteroalkyl can also refer to an alkyl group which includes a heteroatom in the alkyl chain.

The term "heteroatom" refers to any atom that is not carbon or hydrogen, for example nitrogen, oxygen, sulfur, phosphorus, boron, chlorine, bromine, or iodine.

The term "pharmaceutically acceptable salt, ester or prodrug" is used throughout the specification to describe any pharmaceutically acceptable form (such as an ester, phosphate ester, salt of an ester or a related group) of a compound which, upon administration to a patient, provides the compound described in the specification. Pharmaceutically acceptable salts include those derived from pharmaceutically acceptable inorganic or organic bases and acids such as hydrochloric acid, hydrobromic acid, sulfuric acid, nitric acid, phosphoric acid, methanesulfonic acid, ethanesulfonic acid, p-toluensulfonic acid, salicylic acid, malic acid, maleic acid, succinic acid, tartaric acid, citric acid and the like. Suitable salts include those derived from alkali metals such as potassium and sodium, alkaline earth metals such as calcium and magnesium, among numerous other acids well known in the art.

Pharmaceutically acceptable "prodrugs" refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound.

The term "heterocyclic" or "heterocycle" refers to a non-aromatic cyclic group that may be partially (contains at least one double bond) or fully saturated and wherein there is at least one heteroatom, such as oxygen, sulfur, nitrogen, or phosphorus in the ring, and wherein said "heterocyclic" or "heterocycle" group can be optionally substituted with one or more substituent selected from the group consisting of halogen, haloalkyl, alkyl, alkoxy, hydroxy, carboxyl derivatives, amido, hydroxyl, acyl, amino, alkylamino, dialkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference.

The term "heteroaryl" or "heteroaromatic", as used herein, refers to an aromatic that includes at least one sulfur, oxygen, nitrogen or phosphorus in the aromatic ring. Nonlimiting examples of heterocylics and heteroaromatics are pyrrolidinyl, tetrahydrofuryl, piperazinyl, piperidinyl, morpholino, thiomorpholino, tetrahydropyranyl, imidazolyl, pyrrolinyl, pyrazolinyl, indolinyl, dioxolanyl, or 1,4-dioxanyl, aziridinyl, furyl, furanyl, pyridyl, pyrimidinyl, benzoxazolyl, 1,2,4-oxadiazolyl, 1,3,4-oxadiazolyl, 1,3,4-thiadiazole, indazolyl, 1,3,5-triazinyl, thienyl, tetrazolyl, benzofuranyl, quinolyl, isoquinolyl, benzothienyl, isobenzofuryl, indolyl, isoindolyl, benzimidazolyl, purine, carbazolyl, oxazolyl, thiazolyl, benzothiazolyl, isothiazolyl, 1,2,4-thiadiazolyl, isooxazolyl, pyrrolyl, quinazolinyl, cinnolinyl, phthalazinyl, xanthinyl, hypoxanthinyl, pyrazole, 1,2,3-triazole, 1,2,4-triazole, 1,2,3-oxadiazole, thiazine, pyridazine, benzothiophenyl, isopyrrole, thiophene, pyrazine, or pteridinyl wherein said heteroaryl or heterocyclic group can be optionally substituted with one or more substituent selected from the group consisting of halogen, haloalkyl, alkyl, alkoxy, hydroxy, carboxyl derivatives, amido, hydroxyl, acyl, amino, alkylamino, dialkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference.

Functional oxygen and nitrogen groups on the heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acycl groups such as acetyl and propionyl, methanesulfonyl, and p-toluenelsulfonyl.

Processes for the Preparation of Active Compounds

General Methods. $^1$H NMR or $^{13}$C NMR spectra were recorded either on 400 MHz or 100 MHz NOVA Spectrometer or 600 MHz or 150 MHz NOVA Spectrometer. The spectra obtained were referenced to the residual solvent peak. They were recorded in deuterated chloroform, dimethyl sulfoxide-d6, deuterium oxide or acetone-d6. Melting points were taken on a Thomas Hoover capillary melting point apparatus and are uncorrected. Low-resolution EI mass spectra were recorded on a JEOL spectrometer. Element analyses were performed by Atlantic Mircolab (Norcross, Ga.). Flash column chromatography was performed using Scientific Absorbent Incorporated Silica Gel 60. Analytical thin layer chromatography (TLC) was performed on precoated glass backed plates from Scientific Adsorbents Incorporated (Silica Gel 60 $F_{254}$). Plates were visualized using ultraviolet or iodine vapors or phosphomolybdic acid (PMA).

Method A: Reductive amination between aldehydes/ketones and amines (Abdel-Magid, et al. (1996) *J. Org. Chem.* 61:3849-3862). 1.0 eq. dialdehydes or ketones and 2.0 eq. amines were mixed in 1,2-dichloroethane and then treated with 3.0 eq. sodium triacetoxyborohydride (1.0-2.0 mol eq. acetic acid may also be added in reactions of ketones). The mixture was stirred at room temperature under an argon or nitrogen atmosphere for hours until the disappearance of the reactants in TLC plates. The reaction mixture was quenched by adding 1 N NaOH, and the product was extracted by ethyl ether, washed by Brine and dried by anhydrous $MgSO_4$. The solvent was evaporated to give the crude free base which could be purified by chromatography. The free base dissolved in ethanolic hydrochloride or tartaric acid to give the salts which usually can recrystallize from $MeOH/Et_2O$.

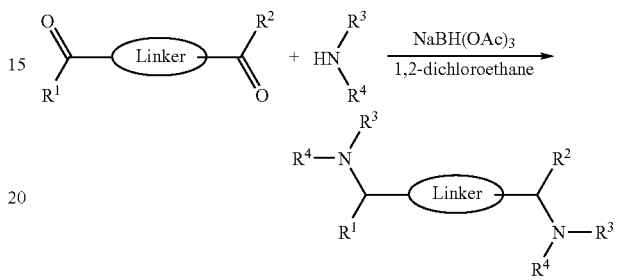

Method B: Reduction of amides (Micovic and Mihailovic (1953) *J. Org. Chem.* 18:1190). The amides could be prepared from the corresponding carboxylic acid or carboxylic chlorides. A mixture of carboxylic acid and thionyl chloride was refluxed for hours in an anhydrous system with a condenser equipped with a NaOH trap at the top. The excess thionyl chloride was removed under reduced pressure to get the carboxylic chloride. The carboxylic chloride was dissolved in dichloromethane following the addition of 2.0 eq. amine and 3 eq. pyridine. The mixture was stirred at room temperature until the disappearance of the reactants in the TLC plates. The solvent was removed under reduced pressure to get the crude amides which can be purified by chromatography.

The mixture of 1 eq. amide and 1.9 eq. $LiAlH_4$ in THF was refluxed until the disappearance of the amide from TLC plates. Then the solution was quenched with the addition of water and 15% NaOH aqueous as described in lit.5 and extracted with ethyl ether, dried over $MgSO_4$. Removal of the solvent gave the free amine product which can be purified by the chromatography. The free base dissolved in ethanolic hydrochloride or tartaric acid to give the salts which usually can recrystallize from $MeOH/Et_2O$.

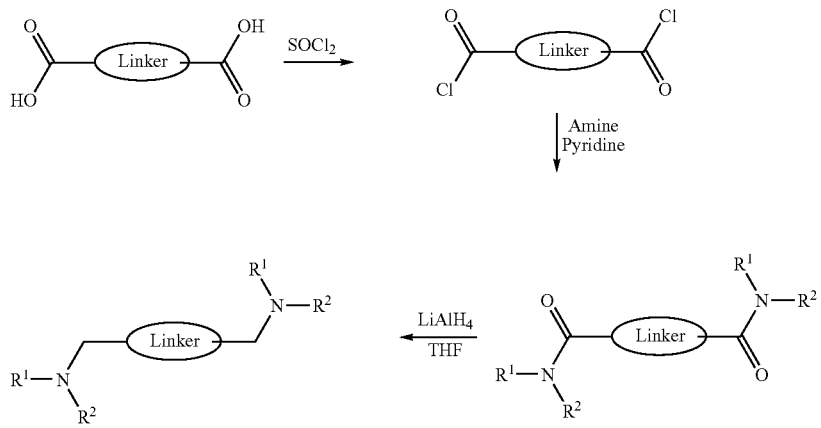

Method C: Nucleophilic addition between amines and chloropyrimidines. 1.0 eq. of diamine dihydrohalide, 5.0 eq. of trialkylamine base and 1.0 eq. of the appropriate chloropyrimidine in dimethylformamide were stirred together at elevated temperatures (80-130° C.) for hours. The reaction is diluted with aqueous saturated NaHCO$_3$. The aqueous phase is twice extracted with EtOAc. The combined organic phases are washed with Brine and dried by anhydrous MgSO$_4$. The solvent was evaporated and the resulting residue was purified by silica gel chromatography.

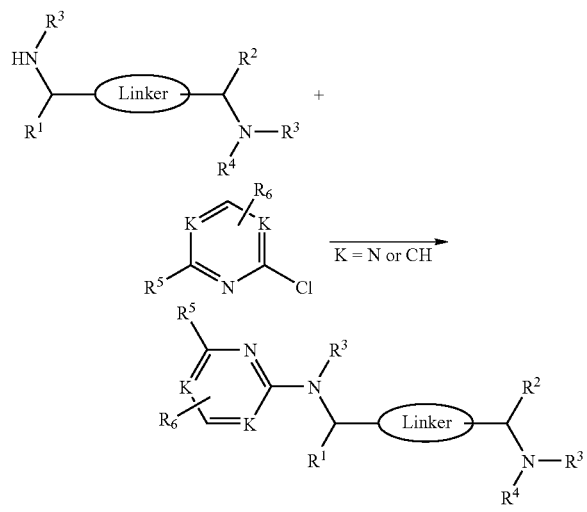

Method D: Removal of tert-butylcarbamate protecting groups to provide free amines. To a solution of 1.0 eq. of tert-butylcarbamate protected amine in methanol was added dropwise 10.0 eq. thionyl chloride. The reaction mixture was stirred at ambient temperature for 45 min before the solvent was evaporated provided the product as a crude product as a hydrochloride salt that is used without further purification.

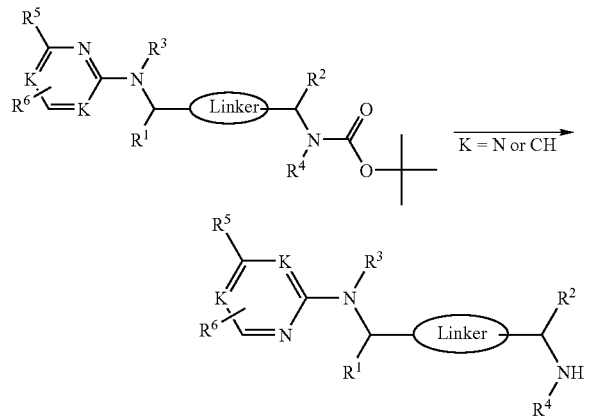

Method E: Nucleophilic addition between amines and chloropyrimidines. 1.0 eq. of amine hydrochloride, 5.0 eq. of trialkylamine base and 1.0 eq. of a 4-chloro-2-thiomethylpyrimidine in dimethylformamide were stirred together at elevated temperatures (80-130° C.) for hours. The reaction is diluted with aqueous saturated NH$_4$Cl. The aqueous phase is twice extracted with EtOAc. The combined organic phases are washed with Brine and aqueous saturated NaHCO$_3$ and dried by anhydrous MgSO$_4$. The solvent was evaporated and the resulting residue was purified by silica gel chromatography.

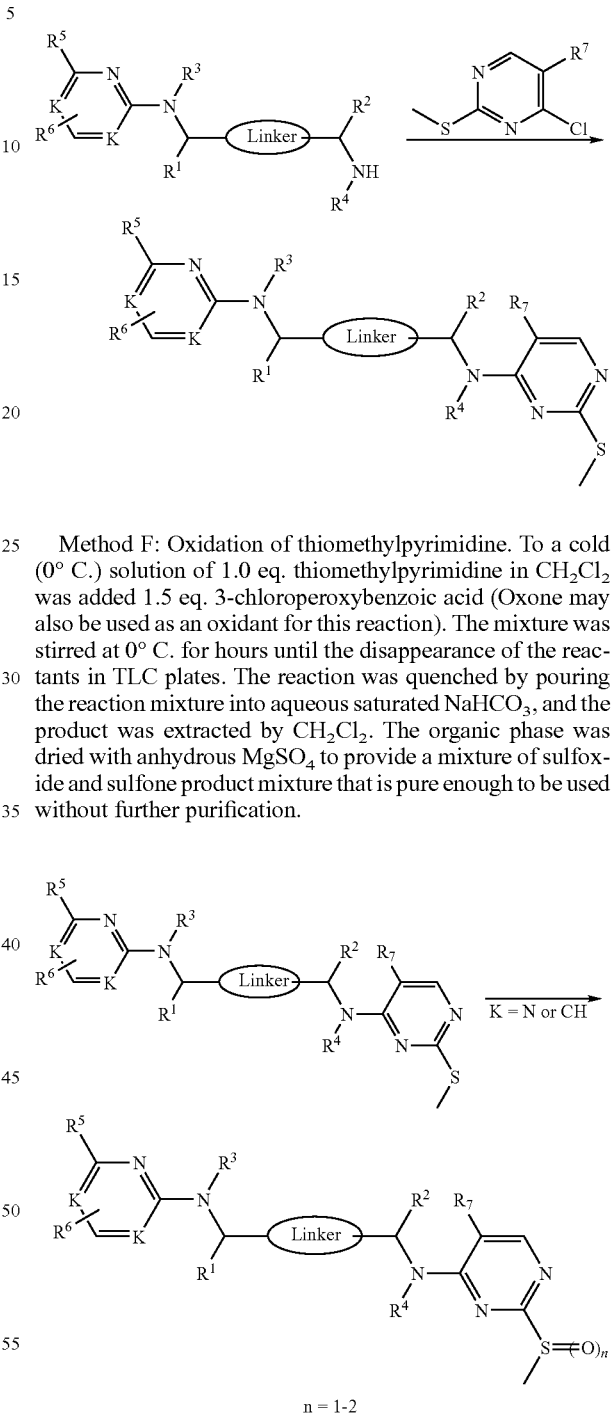

Method F: Oxidation of thiomethylpyrimidine. To a cold (0° C.) solution of 1.0 eq. thiomethylpyrimidine in CH$_2$Cl$_2$ was added 1.5 eq. 3-chloroperoxybenzoic acid (Oxone may also be used as an oxidant for this reaction). The mixture was stirred at 0° C. for hours until the disappearance of the reactants in TLC plates. The reaction was quenched by pouring the reaction mixture into aqueous saturated NaHCO$_3$, and the product was extracted by CH$_2$Cl$_2$. The organic phase was dried with anhydrous MgSO$_4$ to provide a mixture of sulfoxide and sulfone product mixture that is pure enough to be used without further purification.

Method G: Displacement of sulfoxide/sulfone functionalities. A mixture of 1.0 eq. sulfoxide/sulfone mixture, 10.0 eq. of amine and 2.0 eq. of trialkylamine in dioxane were stirred together at reflux for hours. The reaction is diluted with aqueous saturated NaHCO$_3$. The aqueous phase is twice extracted with EtOAc. The organic phases are dried by anhydrous MgSO$_4$. The solvent was evaporated and the resulting residue was purified by silica gel chromatography.

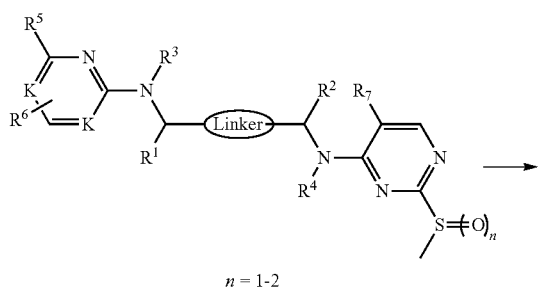

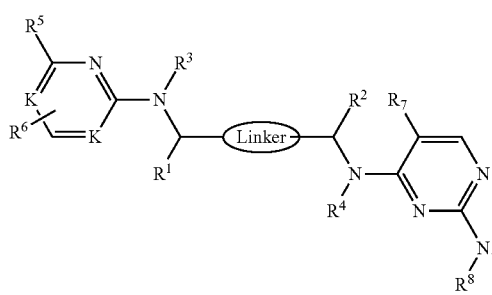

Method H: Acylation of amines for generation of pyrimidine carboxamides. A mixture of 1.0 eq. the appropriate pyrimidine acid chloride and 1.0 eq. of an amine in tetrahydrofuran were stirred together at ambient temperature (80-130° C.) for several hours. The reaction is diluted with water. The aqueous phase is extracted with EtOAc. The organic phase is twice washed with water, twice washed with Brine, and dried by anhydrous sodium sulfate. The solvent was evaporated and the resulting residue was used without further purification.

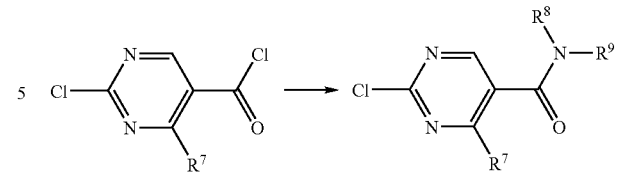

Method I: Displacement of 5-acyl-2-chloropyrimidines. A mixture of 1.0 eq. (aminomethyl)benzyl pyrimidine, 1.0 eq. of the appropriate 2-chloropyrimidine and 5.0 eq. of trialkylamine in dimethylformamide were stirred together at elevated temperatures (80-130° C.) for several hours. The reaction is diluted with water. The aqueous phase is twice extracted with EtOAc. The combined organic phases are twice washed with water, twice washed with Brine, and dried by anhydrous sodium sulfate. The solvent was evaporated and the resulting residue was purified by silica gel chromatography.

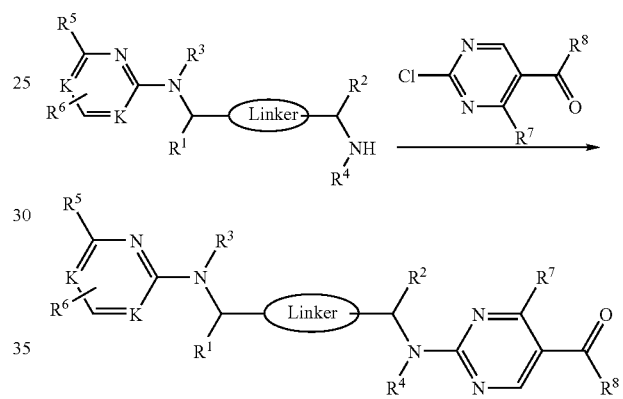

TABLE 1

CHARACTERIZATION DATA FOR THE PREPARED COMPOUNDS

| Entry | Structure | $^1$HNMR/$^{13}$CNMR | Mass Spectral Data |
|---|---|---|---|
|  |  | CDCl$_3$: $^1$H (400 MHz,): 8.29 (d, J = 4.8 Hz, 2H), 7.30-7.37 (m, 5H), 7.06 (dd, J$_1$ = 7.6 Hz, J$_2$ = 1.6 Hz, 1H), 6.95 (td, J$_1$ = 7.6 Hz, J$_2$ = 1.6 Hz, 1H), 6.70 (d, J = 7.6 Hz, 1H), 6.56 (t, J = 4.8 Hz, 1H), 6.13 (br, 1H), 5.58 (br, 1H), 4.65 (d, J = 6.0 Hz, 2H), 4.31 (d, J = 4.8 Hz, 2H), 4.21 (br, 1H), 1.50 (s, 9H); $^{13}$C (100 MHz): 162.26, 158.14, 154.37, 142.17, 138.25, 138.20, 127.90, 126.67, 125.43, 124.31, 118.21, 112.71, 110.79, 80.61, 48.11, 45.21, 28.45. | HRMS: (M + H)$^+$ Found 406.2253 Calcd. (406.2243) |
|  |  | CDCl$_3$: 1H (400 MHz): 8.30 (d, J = 4.8 Hz, 2H), 7.33 (s, 4H), 7.06 (t, J = 8.0 Hz, 1H), 6.86 (s, 1H), 6.57 (t, J = 4.8 Hz, 2H), 6.40 (s, 1H), 6.30 (dd, J$_1$ = 8.0 Hz, J$_2$ = 1.6 Hz, 1H), 5.51 (br, 1H), 4.64 (d, J = 6.0 Hz, 2H), 4.31 (d, J = 4.8 Hz, 2H), 4.04 (br, 1H), 1.51 (s, 9H); $^{13}$C (100 MHz):162.46, 58.28, 152.89, 149.06, 139.59, 138.52, 138.26, 129.86, 127.93, 111.04, 107.93, 107.74, 103.09, 80.45, 48.10, 45.30, 28.54. | HRMS: (M + H)$^+$ Found 406.2239 Calcd. (406.2243) |

TABLE 1-continued

CHARACTERIZATION DATA FOR THE PREPARED COMPOUNDS

| Entry | Structure | $^1$HNMR/$^{13}$CNMR | Mass Spectral Data |
|---|---|---|---|
| | (pyrimidine-NH-CH$_2$-C$_6$H$_4$-CH$_2$-NH-C$_6$H$_4$-NH-Boc) | CDCl$_3$: 1H (400 MHz): 8.31 (d, J = 4.8 Hz, 2H), 7.33 (s, 4H), 7.14 (d, J = 7.2 Hz, 2H), 6.56-6.59 (m, 3H), 6.24 (br, 1H), 5.49 (br, 1H), 4.64 (d, J = 6.0 Hz, 2H), 4.29 (s, 2H), 1.65 (br, 1H), 1.50 (s, 9H); $^{13}$C (100 MHz): 162.43, 158.26, 153.59, 144.66, 138.64, 138.23, 128.98, 127.90, 121.32, 113.43, 110.99, 80.10, 48.51, 45.27, 28.57, | HRMS: (M + H)$^+$ Found 406.2235 Calcd. (406.2243) |
| | (pyrimidine-NH-CH$_2$-C$_6$H$_4$-CH$_2$-NH-C$_6$H$_4$-NH$_2$) 3 HCl | DMSO-d$_6$/D$_2$O: 1H (400 MHz): 8.43 (br, 2H), 7.23-7.29 (m, 4H), 6.98 (d, J = 8.8 Hz, 2H), 6.83 (t, J = 4.8 Hz, 1H), 6.64 (d, J = 8.8 Hz, 2H), 4.53 (s, 2H), 4.24 (br, 2H). | HRMS: (M + H)$^+$ Found 306.1716 Calcd. (306.1719) |
| | (pyrimidine-NH-CH$_2$-C$_6$H$_4$-CH$_2$-NH-C$_6$H$_4$(o-NH$_2$)) | CDCl$_3$: 1H (400 MHz): 8.25 (d, J = 5.6 Hz, 2H), 7.33-7.38 (m, 4H), 6.81 (dd, J$_1$ = 7.2 Hz, J$_2$ = 2.0 Hz, 1H), 6.59-6.76 (m, 3H), 6.54 (t, J = 4.8 Hz, 1H), 5.83 (t, J = 5.6 Hz, 1H), 4.64 (d, J = 5.6 Hz, 2H), 4.31 (s, 2H), 3.48 (br, 3H); $^{13}$C (100 MHz): 162.49, 158.32, 138.63, 138.33, 137.86, 134.34, 128.24, 127.91, 120.94, 119.03, 116.73, 112.14, 111.10, 48.51, 45.33. | HRMS: (M + H)$^+$ Found 306.1712 Calcd. (306.1719) |
| | (pyrimidine-NH-CH$_2$-C$_6$H$_4$-CH$_2$-NH-C$_6$H$_4$(m-pyrrolidinyl)) | CDCl$_3$: 1H (400 MHz): 8.19 (br, 2H), 7.33-7.38 (m, 4H), 7.06 (t, J = 8.0 Hz, 1H), 6.50 (t, J = 4.8 Hz, 1H), 6.28 (t, J = 5.6 Hz, 1H), 6.03 (dd, J$_1$ = 6.0 Hz, J$_2$ = 2.0Hz, 2H), 5.88 (t, J = 2.0 Hz, 1H), 4.64 (d, J = 5.6 Hz, 2H), 4.34 (s, 2H), 4.01 (br, 1H), 3.24-3.30 (m, 4H), 1.95-2.01 (m, 4H); $^{13}$C (100 MHz): 162.41, 158.14, 149.36, 149.15, 139.10, 138.04, 129.97, 127.90, 110.77, 102.24, 101.17, 96.34, 48.23, 47.65, 45.29, 25.54. | HRMS: (M + H)$^+$ Found 360.2181 Calcd. (360.2188) |
| | (pyrimidine-NH-CH$_2$-C$_6$H$_4$-CH$_2$-NH-C$_6$H$_4$(p-pyrrolidinyl)) | CDCl$_3$: 1H (400 MHz): 8.30 (d, J = 4.8 Hz, 2H), 7.31-7.37 (m, 4H), 6.65 (br, 2H), 6.57 (t, J = 4.8 Hz, 1H), 6.55 (br, 2H), 5.41 (br, 1H), 4.63 (d, J = 5.6 Hz, 2H), 4.27 (br, 2H), 3.63 (br, 1H), 3.20 (br, 4H), 1.95-1.99 (m, 4H); $^{13}$C (100 MHz): 162.48, 158.26, 142.07, 139.21, 138.00, 128.04, 127.87, 115.19, 113.31, 110.97, 49.63, 48.51, 25.44. | HRMS: (M + H)$^+$ Found 360.2183 Calcd. (360.2188) |
| | (pyrimidine-NH-CH$_2$-C$_6$H$_4$-CH$_2$-NH-C$_6$H$_4$(o-pyrrolidinyl)) | CDCl$_3$: 1H (400 MHz): 8.27 (d, J = 4.8 Hz, 2H), 7.33-7.39 (m, 4H), 7.05 (dd, J$_1$ = 7.6 Hz, J$_2$ = 1.6 Hz, 1H), 6.95 (td, J$_1$ = 7.6 Hz, J$_2$ = 1.6 Hz, 1H), 6.70 (td, J$_1$ = 7.6 Hz, J$_2$ = 1.6 Hz, 1H), 6.59 (dd, J$_1$ = 7.6 Hz, J$_2$ = 1.6 Hz, 1H), 6.55 (t, J = 4.8 Hz, 1H), 5.68 (br, 1H), 4.91 (br, 1H), 4.65 (d, J = 6.0 Hz, 2H), 4.36 (d, J = 5.2 Hz, 2H), 3.04-3.07 (m, 4H), 1.88-1.95 (m, 4H); $^{13}$C (100 MHz): 162.48, 158.22, 143.51, 139.23, 137.97, 137.42, 127.93, 127.69, 124.22, 118.56, 117.10, 110.86, 110.47, 51.42, 48.22, 45.34, 24.23. | HRMS: (M + H)$^+$ Found 360.2181 Calcd. (360.2188) |
| | (5-F-pyrimidine-NH-CH$_2$-C$_6$H$_4$-CH$_2$-NH-5-F-pyrimidine) | DMSO-d$_6$: $^1$H (400 MHz): 8.33 (s, 4H), 7.78 (t, J = 6.0 Hz, 2H), 7.21 (s, 4H), 4.41 (d, J = 6.0 Hz, 4H); $^{13}$C (100 MHz): 159.47, 151.60 (d, J = 242.8 Hz), 145.49, 138.44, 126.86, 44.24. | HRMS: (M + H)$^+$ Found 329.1319 Calcd. (329.1326) |

TABLE 1-continued

CHARACTERIZATION DATA FOR THE PREPARED COMPOUNDS

| Entry | Structure | ¹HNMR/¹³CNMR | Mass Spectral Data |
|---|---|---|---|
| | | DMSO-d$_6$: 1H (400 MHz): 8.29 (s, 2H), 8.21 (d, J = 4.6 Hz, 2H), 7.74 (t, J = 6.2 Hz, 1H), 7.63 (t, J = 6.2 Hz, 1H), 7.17 (s, 4H), 6.51 (t, J = 4.6 Hz, 1H), 4.41 (d, J = 6.2 Hz, 2H), 4.38 (d, J = 6.2 Hz, 2H). | MS (EI+) 311 (M + H)$^+$ |
| | | DMSO-d$_6$: 1H (400 MHz): 8.57 (d, J = 4.6 Hz, 1H), 8.39 (br s, 1H), 8.31 (s, 2H), 7.75 (t, J = 6.2 Hz, 1H), 7.21 (s, 4H), 6.96 (d, J = 4.6 Hz, 1H), 4.47 (br m, 2H), 4.40 (d, J = 6.2 Hz, 2H). | MS (EI+) 379 (M + H)$^+$ |
| | | DMSO-d$_6$: 1H (400 MHz): 8.57 (d, J = 4.7 Hz, 2H), 8.36 (br m, 2H), 7.24 (2, 4H), 6.96 (d, J = 4.7 Hz, 2H), 4.46 (br m, 4H). | MS (EI+) 429 (M + H)$^+$ |
| | | DMSO-d$_6$: 1H (400 MHz): 1H (400 MHz): 7.63 (t, J = 6.2 Hz, 2H), 7.22 (s, 4H), 5.30 (s, 2H), 4.36 (d, J = 6.2 Hz, 4H), 3.70 (s, 12H). | MS (EI+) 413 (M + H)$^+$ |
| | | DMSO-d$_6$: 1H (400 MHz): 8.70 (t, J = 6.2 Hz, 1H), 8.55 (d, J = 5.0 Hz, 1H), 8.36 (br m, 1H), 8.05 (d, J = 3.5 Hz, 1H), 7.22 (s, 4H), 6.93 (d, J = 5.0 Hz, 1H), 4.48 (d, J = 6.2 Hz, 2H), 4.43 (br m, 2H). | MS (EI+) 413 (M + H)$^+$ |
| | | DMSO-d$_6$: 1H (400 MHz): 8.67 (br m, 1H), 8.59 (d, J = 5.0 Hz, 1H), 8.49 (s, 1H), 8.41 (br m, 1H), 7.26 (s, 4H), 6.98 (d, J = 5.0 Hz, 1H), 4.51 (br m, 2H), 4.47 (br m, 2H), 3.55 (br m, 2H), 3.23 (br m, 2H), 2.69 (br m, 1H), 2.41 (br m, 4H), 0.96 (d, J = 6.8 Hz, 6H). | MS (EI+) 583 (M + H)$^+$ |

TABLE 1-continued

CHARACTERIZATION DATA FOR THE PREPARED COMPOUNDS

| Entry | Structure | $^1$HNMR/$^{13}$CNMR | Mass Spectral Data |
|---|---|---|---|
| | 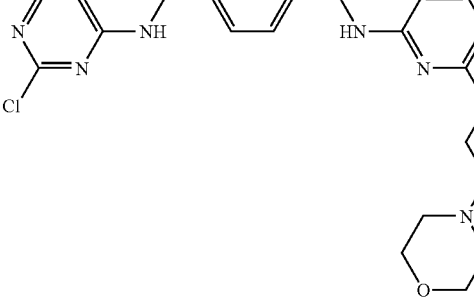 | DMSO-d$_6$: 1H (400 MHz): 8.78 (m, 1H), 8.10 (d, J = 2.8 Hz, 1H), 7.68 (d, J = 6.4 Hz, 1H), 7.27 (s, 4H), 5.99 (br m, 1H), 4.51 (d, J = 6.4 Hz, 4H), 3.56 (m, 4H), 3.45-3.25 (m, 8H). | MS (EI+) 473 (M + H)$^+$ |
| | 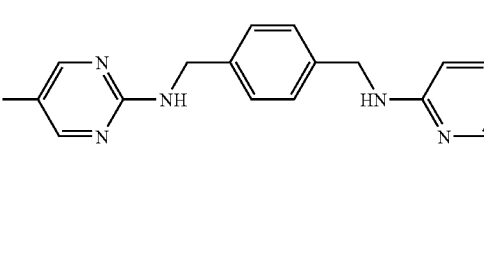 | DMSO-d$_6$: 1H (400 MHz): 8.33 (s, 2H), 7.80 (dd, J = 6.0, 6.0 Hz, 1H), 7.66 (d, J = 6.4 Hz, 1H), 7.25-7.21 (m, 5H), 5.92 (br m, 1H), 4.47 (br m, 2H), 4.41 (d, J = 6.0 Hz, 2H), 3.62-3.51 (m, 6H), 3.44-3.26 (m, 6H). | MS (EI+) 439 (M + H)$^+$ |
| | 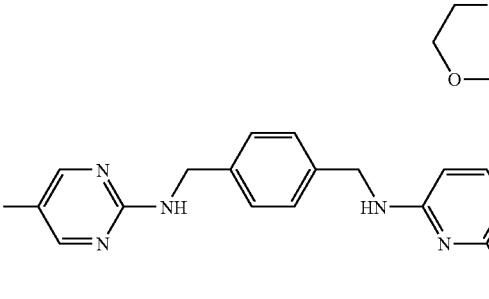 | DMSO-d$_6$: 1H (400 MHz): 8.33 (s, 2H), 8.06 (br m, 1H), 7.89-7.83 (m, 1H), 7.81-7.76 (m, 1H), 7.28-7.19 (m, 4H), 6.26-6.18 (m, 1H), 4.47 (m, 2H), 4.42 (d, J = 6.0 Hz, 2H), 2.37 (s, 3H). | MS (EI+) 357 (M + H)$^+$ |
| | 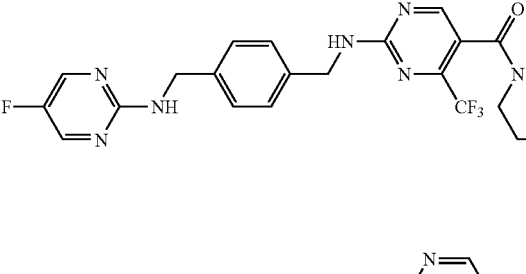 | DMSO-d$_6$: 1H (400 MHz): 8.29 (s, 2H), 8.21 (d, J = 4.6 Hz, 2H), 7.74 (t, J = 6.2 Hz, 1H), 7.63 (t, J = 6.2 Hz, 1H), 7.17 (s, 4H), 6.51 (t, J = 4.6 Hz, 1H), 4.41 (d, J = 6.2 Hz, 2H), 4.38 (d, J = 6.2 Hz, 2H), 3.55 (br m, 2H), 3.23 (br m, 2H), 2.69 (br m, 1H), 2.41 (br m, 4H), 0.96 (d, J = 6.8 Hz, 6H). | MS (EI+) 533 (M + H)$^+$ |
| | 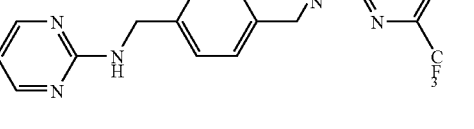 | DMSO-d$_6$: 1H (400 MHz): 8.66 (br m, 1H), 8.48 (s, 1H), 8.33 (s, 2H), 7.79 (t, J = 6.1 Hz, 1H), 7.24 (s, 4H), 4.49 (dd, J = 21.9, 5.4 Hz, 2H), 4.43 (d, J = 6.1 Hz, 2H), 3.66 (br m, 2H), 3.46 (t, J = 5.8 Hz, 2H), 3.42 (br m, 2H), 3.92 (q, J = 6.9 Hz, 2H), 3.24 (br m, 2H), 2.51 (m, 2H), 2.47 (m, 2H), 1.09 (t, J = 6.9 Hz, 3H). | MS (EI+) 563 (M + H)$^+$ |

TABLE 1-continued

CHARACTERIZATION DATA FOR THE PREPARED COMPOUNDS

| Entry | Structure | $^1$HNMR/$^{13}$CNMR | Mass Spectral Data |
|---|---|---|---|
| |  | DMSO-$d_6$: 1H (400 MHz): 8.69 (br m, 1H), 8.58 (d, J = 5.2 Hz, 1H), 8.47 (s, 1H), 8.44 (br m, 1H), 7.25 (s, 4H), 6.97 (d, J = 5.2 Hz, 1H), 4.51 (br m, 2H), 4.47 (br m, 2H), 3.63 (br m, 2H), 3.46 (t, J = 6.0 Hz, 2H), 3.40 (q, J = 7.2 Hz, 2H), 3.23 (br m, 2H), 2.48 (t, J = 6.0 Hz, 2H), 2.40 (br m, 4H), 1.08 (t, J = 7.2 Hz, 3H). | MS (EI+) 613 (M + H)$^+$ |

Stereoisomerism and Polymorphism

Compounds of the present invention having a chiral center may exist in and be isolated in optically active and racemic forms. The present invention encompasses any racemic, optically-active, diastereomeric, polymorphic, or stereoisomeric form, or mixtures thereof, of a compound of the invention, which possess the useful properties described herein.

Examples of methods to obtain optically active materials are known in the art, and include at least the following.

i) physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization—a technique whereby the individual enantiomers are separately crystallized from a solution of the racemate, possible only if the latter is a conglomerate in the solid state; iii) enzymatic resolutions—a technique whereby partial or complete separation of a racemate by virtue of differing rates of reaction for the enantiomers with an enzyme;

iv) enzymatic asymmetric synthesis—a synthetic technique whereby at least one step of the synthesis uses an enzymatic reaction to obtain an enantiomerically pure or enriched synthetic precursor of the desired enantiomer;

v) chemical asymmetric synthesis—a synthetic technique whereby the desired enantiomer is synthesized from an achiral precursor under conditions that produce asymmetry (i.e., chirality) in the product, which may be achieved using chrial catalysts or chiral auxiliaries;

vi) diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors—a synthetic technique whereby the desired enantiomer is obtained from non-chiral starting materials and where the stereochemical integrity is not or is only minimally compromised over the course of the synthesis;

x) chiral liquid chromatography—a technique whereby the enantiomers of a racemate are separated in a liquid mobile phase by virtue of their differing interactions with a stationary phase. The stationary phase can be made of chiral material or the mobile phase can contain an additional chiral material to provoke the differing interactions;

xi) chiral gas chromatography—a technique whereby the racemate is volatilized and enantiomers are separated by virtue of their differing interactions in the gaseous mobile phase with a column containing a fixed non-racemic chiral adsorbent phase;

xi) xii) extraction with chiral solvents—a technique whereby the enantiomers are separated by virtue of preferential dissolution of one enantiomer into a particular chiral solvent;

xii) xiii) transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane which allows only one enantiomer of the racemate to pass through.

Formulations

In cases where compounds are sufficiently basic or acidic to form stable nontoxic acid or base salts, administration of the compounds as salts may be appropriate. The term pharmaceutically acceptable salts or complexes refers to salts or complexes that retain the desired biological activity of the compounds of the present invention and exhibit minimal undesired toxicological effects.

Nonlimiting examples of such salts are (a) acid addition salts formed with inorganic acids such as sulfate, nitrate, bicarbonate, and carbonate salts (for example, hydrochloric acid, hydrobromic acid, sulfuric acid, phosphoric acid, nitric acid, and the like), and salts formed with organic acids including tosylate, methanesulfonate, acetate, citrate, malonate, tartarate, succinate, ascorbate, benzoate, α-ketoglutarate, and α-glycerophosphate salts, such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, lithium and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —NR$^+$A$^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The active compound can also be provided as a prodrug, which is converted into a biologically active form in vivo. A prodrug may be converted into the parent drug by various mechanisms, including enzymatic processes and metabolic hydrolysis. Harper, N.J. (1962) in Jucker, ed. *Progress in Drug Research*, 4:221-294; Morozowich et al. (1977) in E. B. Roche ed. *Design of Biopharmaceutical Properties through Prodrugs and Analogs*, APhA (Acad. Pharm. Sci.); E. B. Roche, ed. (1977) *Bioreversible Carriers in Drug in Drug Design, Theory and Application*, APhA; H. Bundgaard, ed. (1985) *Design of Prodrugs*, Elsevier; Wang et al. (1999) *Curr. Pharm. Design.* 5(4):265-287; Pauletti et al. (1997) *Adv. Drug. Delivery Rev.* 27:235-256; Mizen et al. (1998) *Pharm. Biotech.* 11:345-365; Gaignault et al. (1996) *Pract. Med. Chem.* 671-696; M. Asghamejad (2000) in G. L. Amidon, P. I. Lee and E. M. Topp, Eds., *Transport Proc. Pharm. Sys.*, Marcell Dekker, p. 185-218; Balant et al. (1990) *Eur. J. Drug Metab. Pharmacokinet.*, 15(2): 143-53; Balimane and Sinko (1999) *Adv. Drug Deliv. Rev.*, 39(1-3):183-209; Browne (1997). *Clin. Neuropharm.* 20(1): 1-12; Bundgaard (1979) *Arch. Pharm. Chemi.* 86(1): 1-39; H. Bundgaard, ed. (1985) *Design of Prodrugs*, New York: Elsevier; Fleisher et al. (1996) *Adv. Drug Delivery Rev*, 19(2): 115-130; Fleisher et al. (1985) *Methods Enzymol.* 112: 360-81; Farquhar D, et al. (1983) *J. Pharm. Sci.*, 72(3): 324-325; Han, H. K. et al. (2000) *AAPS Pharm Sci.*, 2(1): E6; Sadzuka Y. (2000) *Curr. Drug Metab.*, 1:31-48; D. M. Lambert (2000) *Eur. J. Pharm. Sci.*, 11 Suppl 2:S1 5-27; Wang, W. et al. (1999) *Curr. Pharm. Des.*, 5(4):265.

The active compound can also be provided as a lipid prodrug. Nonlimiting examples of U.S. patents that disclose suitable lipophilic substituents that can be covalently incorporated into the compound or in lipophilic preparations, include U.S. Pat. Nos. 5,149,794 (Sep. 22, 1992, Yatvin et al.); 5,194,654 (Mar. 16, 1993, Hostetler et al., 5,223,263 (Jun. 29, 1993, Hostetler et al.); 5,256,641 (Oct. 26, 1993, Yatvin et al.); 5,411,947 (May 2, 1995, Hostetler et al.); 5,463,092 (Oct. 31, 1995, Hostetler et al.); 5,543,389 (Aug. 6, 1996, Yatvin et al.); 5,543,390 (Aug. 6, 1996, Yatvin et al.); 5,543,391 (Aug. 6, 1996, Yatvin et al.); and 5,554,728 (Sep. 10, 1996, Basava et al.).

Method of Treatment

The compounds described herein, are particularly useful for the treatment or prevention of a disorder associated with CXCR4 receptor binding or activation. In one embodiment, the compounds described herein, are useful for the treatment or prevention of a proliferative disorder, including cancer metastasis, modulated via CXCR4. In another embodiment, the compounds described herein, are useful for the treatment or prevention of HIV or AIDS in a host.

In one embodiment, a method of preventing metastases of a malignant cell is provided that includes administering a compound of at least one of Formula (I)-(V) to a host. The malignant cell can be a tumor cell. In certain embodiments, the compound can be provided to a host before treatment of a tumor. In a separate embodiment, the compound is provided to a patient that has been treated for cancer to reduce the likelihood of recurrence, or reduce mortality associated with a particular tumor. In another embodiment, the compound is administered to a host at high risk of suffering from a proliferative disease. Such high risk can be based, for example, on family history or on a history of exposure to known or presumed carcinogens.

In one embodiment, a method of treating or preventing HIV infection or reduction of symptoms associated with AIDS is provided including administering a compound of at least one of Formula (I)-(V) to a host. In certain embodiments, the compound can be provided to a host before treatment of infection with another compound. In a separate embodiment, the compound is provided to a patient that has been treated for HIV infection to reduce the likelihood of recurrence, or reduce mortality associated with AIDS related symptoms. In another embodiment, the compound is administered to a host at high risk of suffering from HIV infections.

Host, including humans suffering from, or at risk for, a proliferative disorder can be treated by administering an effective amount of the active compound or a pharmaceutically acceptable prodrug or salt thereof in the presence of a pharmaceutically acceptable carrier or diluent. The administration can be prophylactically for the prevention of a disorder associated with CXCR4 receptor activation, and particularly a proliferative disorder, including cancer metastasis, or a HIV infection or reduction of symptoms associated with AIDS. The active materials can be administered by any appropriate route, for example, orally, parenterally, intravenously, intradermally, subcutaneously, or topically, in liquid or solid form. However, the compounds are particularly suited to oral delivery.

A preferred dose of the compound will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent compound to be delivered. If the salt, ester or prodrug exhibits activity in itself, the effective dosage can be estimated as above using the weight of the salt, ester or prodrug, or by other means known to those skilled in the art.

In a separate embodiment, a method of treating proliferative disorders by administering a compound of Formulas (I)-(V) to a host in need of treatment is provided. In certain embodiments, the proliferative disorder is cancer, and in particular subembodiments, the disorder is a metastatic cancer.

The compounds of the invention can be administered to a host in need thereof to reduce the incidence of metastasis of a proliferative disorder, such as cancer. In particular embodiments, the cancer is breast cancer, brain tumor, pancreatic cancer, ovarian tumor, particularly an ovarian epithelial tumor, prostate cancer, kidney cancer, or non-small cell lung cancer.

In another embodiment, the invention provides a method of reducing neovascularization, particularly VEGF-dependent neocascularization, by contacting a cell with a compound of Formula (I)-(V). The cell can be in a host animal.

In a separate embodiment, a method for treating diseases of vasculature, inflammatory and degenerative diseases is provided including administering a compound of Formula (I)-(V) to a host. In one embodiment, a compound of Formula (I)-(V) is used to stimulate the production and proliferation of stem cells and progenitor cells.

The compounds can prevent or reduce the severity of diseases associated with CXCR4 acitivity, and in particular of proliferative diseases in any host. However, typically the host is a mammal and more typically is a human. In certain subembodiments the host has been diagnosed with a hyperproliferative disorder prior to administration of the compound, however in other embodiments, the host is merely considered at risk of suffering from such a disorder.

In a separate embodiment, a method for the treatment or prevention of HIV infection or reduction of symptoms associated with AIDS by administering a compound of Formulas (I)-(V) to a host in need of treatment is provided. The compounds of the invention can be administered to a host in need thereof to reduce the severity of AIDS related disorders. In one embodiment of the invention, the host is a human.

In another embodiment, the invention provides a method of treating symptoms associated with other infections associated with CXCR4 receptor activation, for example, liver diseases associated with flavivirus or pestivirus infection, and in particular, HCV or HBV, by contacting a cell with a compound of Formula (I)-(V). The cell can be in a host animal, in particular in a human.

The compounds can treat or prevent HIV infection, or reduce the severity of AIDS related symptoms and diseases in any host. However, typically the host is a mammal and more typically is a human. In certain subembodiments the host has been diagnosed with AIDS prior to administration of the compound, however in other embodiments, the host is merely infected with HIV and asymptomatic.

Diseases

The compounds described herein, are particularly useful for the treatment or prevention of a disorder associated with CXCR4 receptor binding or activation, and particularly a proliferative disorder, including cancer metastasis, and HIV viral infections. However, multiple other diseases have been associated with CXCR4 receptor signaling.

Human and simian immunodeficiency viruses (HIV and SIV, respectively) enter cells through a fusion reaction triggered by the viral envelope glycoprotein (Env) and two cellular molecules: CD4 and a chemokine receptor, generally either CCR5 or CXCR5. (Alkhatib G, Combadiere C, Croder C, Feng Y, Kennedy P E, Murphy P M, Berger E A. CC CKR5. a RANTES, MIP-1apha, MIP-1Beta receptor as a fusion cofactor for macrophage-tropic HIV-1. *Science*. 1996; 272: 1955-1988).

In approximately 50% of infected individuals, CXCR4-tropic (X4-tropic) viruses emerge later in HIV infection, and their appearance correlates with a more rapid CD4 decline and a faster progression to AIDS (Connor, et al. (1997) *J Exp. Med.* 185: 621-628). Dual-tropic isolates that are able to use both CCR5 and CXCR4 are also seen and may represent intermediates in the switch from CCR5 to CXCR4 tropism (Doranz, et al. (1996) *Cell*. 85: 1149-1158).

In a separate embodiment, a method for the treatment of, prevention of, or reduced severity of liver disease associated with viral infections including administering at least one compound described herein is provided.

Chronic hepatitis C virus (HCV) and hepatitis B virus (HBC) infection is accompanied by inflammation and fibrosis eventually leading to cirrhosis. A study testing the expression and function of CXCR4 on liver-infiltrating lymphocytes (LIL) revealed an important role for the CXCL12/CXCR4 pathway in recruitment and retention of immune cells in the liver during chronic HCV and HBV infection (Wald, et al. (2004) *European Journal of Immunology*. 34(4): 1164-1174).

High levels of CXCR4 and TGF-β have been detected in liver samples obtained from patients infected with HCV. (Mitra, et al. (1999) *Int. J. Oncol.* 14: 917-925). In vitro, TGF-β has been shown to up-regulate the expression of CXCR4 on naïve T cells and to increase their migration. The CD69/TGF-β/CXCR4 pathway may be involved in the retention of recently activated lymphocytes in the liver (Wald, et al. *European Journal of Immunology*. 2004; 34(4): 1164-1174).

The compounds can be used to treat disorders of abnormal cell proliferation generally, examples of which include, but are not limited to, types of cancers and proliferative disorders listed below. Abnormal cellular proliferation, notably hyperproliferation, can occur as a result of a wide variety of factors, including genetic mutation, infection, exposure to toxins, autoimmune disorders, and benign or malignant tumor induction.

There are a number of skin disorders associated with cellular hyperproliferation. Psoriasis, for example, is a benign disease of human skin generally characterized by plaques covered by thickened scales. The disease is caused by increased proliferation of epidermal cells of unknown cause. In normal skin the time required for a cell to move from the basal layer to the upper granular layer is about five weeks. In psoriasis, this time is only 6 to 9 days, partially due to an increase in the number of proliferating cells and an increase in the proportion of cells which are dividing (G. Grove, Int. J. Dermatol. 18:111, 1979). Chronic eczema is also associated with significant hyperproliferation of the epidermis. Other diseases caused by hyperproliferation of skin cells include atopic dermatitis, lichen planus, warts, pemphigus vulgaris, actinic keratosis, basal cell carcinoma and squamous cell carcinoma.

Other hyperproliferative cell disorders include blood vessel proliferation disorders, fibrotic disorders, autoimmune disorders, graft-versus-host rejection, tumors and cancers.

Blood vessel proliferative disorders include angiogenic and vasculogenic disorders. Proliferation of smooth muscle cells in the course of development of plaques in vascular tissue cause, for example, restenosis, retinopathies and atherosclerosis. The advanced lesions of atherosclerosis result from an excessive inflammatory-proliferative response to an insult to the endothelium and smooth muscle of the artery wall (Ross, R. *Nature,* 1993, 362:801-809). Both cell migration and cell proliferation play a role in the formation of atherosclerotic lesions.

Fibrotic disorders are often due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis.

Mesangial disorders are brought about by abnormal proliferation of mesangial cells. Mesangial hyperproliferative cell disorders include various human renal diseases, such as glomerulonephritis, diabetic nephropathy, malignant nephrosclerosis, thrombotic micro-angiopathy syndromes, transplant rejection, and glomerulopathies.

Another disease with a proliferative component is rheumatoid arthritis. Rheumatoid arthritis is generally considered an autoimmune disease that is thought to be associated with activity of autoreactive T cells (See, e.g., Harris, E. D., Jr. (1990) *The New England Journal of Medicine,* 322:1277-1289), and to be caused by autoantibodies produced against collagen and IgE.

Other disorders that can include an abnormal cellular proliferative component include Behcet's syndrome, acute respiratory distress syndrome (ARDS), ischemic heart disease, post-dialysis syndrome, leukemia, acquired immune deficiency syndrome, vasculitis, lipid histiocytosis, septic shock and inflammation in general.

Examples of proliferative disorders which can be the primary tumor that is treated, or which can be the site from which metastasis is inhibited or reduced, include but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvis, skin, soft tissue, spleen, thorax, and urogenital tract.

Specific types of diseases include Acute Childhood Lymphoblastic Leukemia; Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Disease, Adult Hodgkin's Lymphorria, Adult Lymphocytic Leukemia, Adult Non-Hodgkin's Lymphoma, Adult Primary Liver Cancer, Adult Soft Tissue Sarcoma, AIDS-Related Lymphorria, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphorria, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalanic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma. Endometrial Cancer, Ependymoma, Epithelial Cancer, Esophageal Cancer, Ewing's Sarcoma and Related Tumors, Exocrine Pancreatic Cancer, Extraeranial Germ Cell Tumor, Extragonadal Germ Cell Tumor, Extrahepatie Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Disease, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lympho proliferative Disorders, Macroglobulinemia, Male Breast Cancer, Malignant Mesothelioma, Malignant Thymoma, Medulloblastomia, Melanoma, Mesothelioma, Metastatie Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyrigeal Cancer, Neuroblastoma, Non-Hodgkin's Lymphoma During Pregnancy, Nonmelanoma Skin Cancer, Non-Small Cell Lung Cancer, Occult Primary Metastatic Squamous Neck Cancer, Oropharyngeal Cancer, Osteo/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Purpura, Parathyroid, Cancer, Penile Cancer, Pheochromocytoma, Pituitary Tumor, Plasma Cell Neoplasm/Multiple Myeloma, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethial Cancer, Uterine Cancer, Uterine Sarcoma, Vaginal Cancer, Visual Pathway and Hypothalarruc Glioma, Vulvar Cancer, Waldenstroin's Macroglobulinemia, Wilm's Tumor, and any other hyperproliferative disease located in an organ system listed above.

Hyperplastic disorders include, but are not limited to, angiofollicular mediastinal lymph node hyperplasia, angiolymphoid hyperplasia with eosinophilia, atypical melanocytic hyperplasia, basal cell hyperplasia, benign giant lymph node hyperplasia, cementum hyperplasia, congenital adrenal hyperplasia, congenital sebaceous hyperplasia, cystic hyperplasia, cystic hyperplasia of the breast, denture hyperplasia, ductal hyperplasia, endometrial hyperplasia, fibromuscular hyperplasia, foca epithelial hyperplasia, gingival hyperplasia, inflammatory fibrous hyperplasia, inflammatory papillary hyperplasia, intravascular papillary endothelial hyperplasia, nodular hyperplasia of prostate, nodular regenerative hyperplasia, pseudoepitheliomatous hyperplasia, senile sebaceous hyperplasia, and verrucous hyperplasia; leukemia (including acute leukemia (e.g., acute lymphocytic leukemia, acute myelocytic leukemia (including myeloblastic, promyelocytic, mylomonocytic, monocytic, and erythroleukemia)) and chronic leukemia (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, Sarcomas and, carcinomas such as fibrosarcoma, myxosarcoma, fiposarcoma, chondrosarcoma, osteogenic sarcoma, chordoma, anglosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendrogliomia, menangioma, melanoma, neuroblastoma, and retinoblastoma.

In a separate embodiment, a method for the treatment of, prevention of, or reduced severity of, age-related macular degeneration (ARMD) and other pathogenic states involving macular retinal pigment epithelial (RPE) cells including administering at least one compound described herein is provided.

CXCR4 plays a crucial role in ocular diseases involving the retina such as age-related macular degeneration (ARMD). The retinal pigment epithelium has a major role in the physiological renewal of photoreceptor outer segments in the provision of a transport and storage system for nutrients essential to the photoreceptor layer. The retinal pigment epithelial (RPE) cells predominantly express CXCR4 receptors. (Crane, et al. (2000) *J. Immunol.* 165: 4372-4278). CXCR4 receptor expression on human retinal pigment epithelial cells from the blood-retina barrier leads to chemokine secretion and migration in response to stromal cell-derived factor 1a. *J. Immunol.* 200; 165: 4372-4278). The level of CXCR4 mRNA expression increases upon stimulation with IL-1β or TNFα (Dwinell, et al. (1999) *Gastroenterology*. 117: 359-367). RPE cells also migrated in response to SDF-1α indicating that SDF-1α/CXCR4 interactions may modulate the affects of chronic inflammation and subretinal neovascularization at the RPE site of the blood-retina barrier. (Crane I J, Wallace C A, McKillop-Smith S, Forrester J V. CXCR4 receptor expression on human retinal pigment epithelial cells from the blood-retina barrier leads to chemokine secretion and migration in response to stromal cell-derived factor 1a. *J. Immunol.* 200; 165: 4372-4278).

Age-related macular degeneration is characterized by both primary and secondary damage of macular RPE cells. Early stages of ARMD are characterized by macular drusen, and irregular proliferation and atrophy of the RPE. The late stages of ARMD present with geographic RPE atrophy, RPE detachment and rupture, choroidal neovascularaization and fibrovascular disciform scarring. Common first symptoms include metamorphopisia and/or general central vision loss resulting in reading disability and difficulties in detecting faces. Late stages of ARMD cause central scomota, which is extremely disabling if occurrence is bilateral (Bressler and Bressler (1995) *Ophthalmology*. 1995; 102: 1206-1211).

In a separate embodiment, a method for the treatment of, prevention of, or reduced severity of inflammatory disease states, neovascularization, and wound healing including administering at least one compound described herein is provided.

Vascular endothelial cells express a multitude of chemokine receptors, with CXCR4 being particularly prominent (Gupta, et al. (1998) *J Biol Chem.* 273: 4282; Volin, et al. (1998) *Biochem Biophys Res Commnun.* 242: 46).

A RT-PCR based strategy which utilized CXCR4 specific primers demonstrated that mRNA for the chemokine receptor CXCR4 is expressed not only in primary cultures and transformed type II alveolar epithelial cells (pneumocytes) but also in a number of epithelial cell lines derived from various other tissues. (Murdoch, et al. (1998) *Immunology*. 98(1): 36-41). Unlike with endothelial cells, CXCR4 is the only chemokine receptor expressed on epithelial cells. The receptor may have a functional role in epithelial pathology. Whether CXCR4 participates in inflammatory responses remains unclear. CXCR4 expressed on the epithelium may facilitate the recruitment of phagocytic cells to sites of inflammation by direct effects on epithelial cells. CXCR4 may also have other functional roles within the immune response or participate in wound healing or neovascularization. CXCR4 may also be involved in the pathophysiology of several acute or chronic inflammatory disease states associated with the epithelium. (Murdoch, et al. (1999) *Immunology*. 98(1): 36-41).

Certain inflammatory chemokines can be induced during an immune response to promote cells of the immune system to a site of infection. Inflammatory chemokines function mainly as chemoattractants for leukocytes, recruiting monocytes, neutrophils and other effector cells from the blood to sites of infection or tissue damage. Certain inflammatory chemokines activate cells to initiate an immune response or promote wound healing. Responses to chemokines include increasing or decreasing expression of membrane proteins, proliferation, and secretion of effector molecules.

In a particular embodiment, the compounds of the invention can be administered to a host at risk of, or suffering from, an inflammatory condition. In one embodiment, the compounds are administered for the treatment or prophylaxis of an inflammatory disorder. In certain embodiments, the inflammatory disorder or condition is mediated by chemokines Generally, inflammatory disorders include, but are not limited to, respiratory disorders (including asthma, COPD, chronic bronchitis and cystic fibrosis); cardiovascular related disorders (including atherosclerosis, post-angioplasty, restenosis, coronary artery diseases and angina); inflammatory diseases of the joints (including rheumatoid and osteoarthritis); skin disorders (including dermatitis, eczematous dermatitis and psoriasis); post transplantation late and chronic solid organ rejection; multiple sclerosis; autoimmune conditions (including systemic lupus erythematosus, dermatomyositis, polymyositis, Sjogren's syndrome, polymyalgia rheumatica, temporal arteritis, Behcet's disease, Guillain Barré, Wegener's granulomatosus, polyarteritis nodosa); inflammatory neuropathies (including inflammatory polyneuropathies); vasculitis (including Churg-Strauss syndrome, Takayasu's arteritis); inflammatory disorders of adipose tissue; and proliferative disorders (including Kaposi's sarcoma and other proliferative disorders of smooth muscle cells).

In one embodiment, compounds, compositions and methods of treatment of respiratory disorders comprising administering a compound are provided wherein the compound is as described herein. Respiratory disorders that may be prevented or treated include a disease or disorder of the respiratory system that can affect any part of the respiratory tract. Respiratory disorders include, but are not limited to, a cold virus, bronchitis, pneumonia, tuberculosis, irritation of the lung tissue, hay fever and other respiratory allergies, asthma, bronchitis, simple and mucopurulent chronic bronchitis, unspecified chronic bronchitis (including chronic bronchitis NOS, chronic tracheitis and chronic tracheobronchitis), emphysema, other chronic obstructive pulmonary disease, asthma, status asthmaticus and bronchiectasis. Other respiratory disorders include allergic and non-allergic rhinitis as well as non-malignant proliferative and/or inflammatory disease of the airway passages and lungs. Non-malignant proliferative and/or inflammatory diseases of the airway passages or lungs means one or more of (1) alveolitis, such as extrinsic allergic alveolitis, and drug toxicity such as caused by, e.g. cytotoxic and/or alkylating agents; (2) vasculitis such as Wegener's granulomatosis, allergic granulomatosis, pulmonary hemangiomatosis and idiopathic pulmonary fibrosis, chronic eosinophilic pneumonia, eosinophilic granuloma and sarcoidoses.

In one embodiment, the compounds of the invention are administered to a patient suffering from a cardiovascular disorder related to inflammation. Cardiovascular inflammatory disorders include atherosclerosis, post-angioplasty, restenosis, coronary artery diseases, angina, and other cardiovascular diseases.

In certain embodiments the disorder is a non-cardiovascular inflammatory disorder such as rheumatoid and osteoarthritis, dermatitis, psoriasis, cystic fibrosis, post transplantation late and chronic solid organ rejection, eczematous dermatitis, Kaposi's sarcoma, or multiple sclerosis. In yet another embodiment, the compounds disclosed herein can be selected to treat anti-inflammatory conditions that are mediated by mononuclear leucocytes.

In addition, the invention is directed to methods of treating animal subjects, in particular, veterinary and human subjects, to enhance or elevate the number of progenitor cells and/or stem cells. The progenitor and/or stem cells may be harvested and used in cell transplantation. In one embodiment, bone marrow progenitor and/or stem cells are mobilized for myocardial repair. Further, the invention is directed to methods of treating animal subjects, in particular, veterinary and human patients, who are defective in white blood cell (WBQ 8 count, or who would benefit from elevation of WBC levels using the compounds disclosed herein. Moreover, the invention is directed to methods of effecting regeneration of cardiac tissue in a subject in need of such regeneration using the disclosed compounds.

The compounds of the invention may be used for the treatment of diseases that are associated with immunosuppression such as individuals undergoing chemotherapy, radiation therapy, enhanced wound healing and burn treatment, therapy for autoinimune disease or other drug therapy (e.g., corticosteroid therapy) or combination of conventional drugs used in the treatment of autoinimune diseases and graft/transplantation rejection, which causes immunosuppression; immunosuppression due to congenital deficiency in receptor function or other causes; and infectious diseases, such as parasitic diseases, including but not limited to helminth infections, such as nematodes (round invention thus targets a broad spectrum of conditions for which elevation of progenitor cells and/or stem cells in a subject would be beneficial or, where harvesting of progenitor cells and/or stem cell for subsequent stem cell transplantation would be beneficial. In addition, the method of the invention targets a broad spectrum of conditions characterized by a deficiency in white blood cell count, or which would benefit from elevation of said WBC count.

The term "progenitor cells" refers to cells that, in response to certain stimuli, can form differentiated hematopoietic or myeloid cells. The presence of progenitor cells can be assessed by the ability of the cells in a sample to form colony-forming units of various types, including, for example, CFU-GM (colony-forming units, granulocytemacrophage); CFU-GEMM (colony-forming units, multipotential); BFU-E (burst-forming units, erythroid); HPP-CFC (high proliferative potential colony-forming cells); or other types of differentiated colonies which can be obtained in culture using known protocols. "Stem" cells are less differentiated forms of progenitor cells. Typically, such cells are often positive for CD34. Some stem cells do not contain this marker, however. In general, CD34+ cells are present only in low levels in the blood, but are present in large numbers in bone marrow.

The compounds of the invention may be administered as sole active ingredients, as mixtures of various compounds of Formula (I)-(V), and/or in admixture with additional active ingredients that are therapeutically or nutritionally useful, such as antibiotics, vitamins, herbal extracts, anti-inflammatories, glucose, antipyretics, analgesics, granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, thrombopoictin, growth related oncogene or chemotherapy and the like. In addition, the compounds of the invention may be administered in admixture with additional active ingredients that are therapeutically or nutritionally useful, such as antibiotics, vitamins, herbal extracts, anti-inflammatories, glucose, antipyretics, analgesics, and the like.

The binding of SDF-1 to CXCR4 has also been implicated in the pathogenesis of atherosclerosis (Abi-Younes et al. Circ. Res. 86, 131-138 (2000)), renal allograft rejection (Eitner et al. Transplantation 66, 1551-1557 (1998)), asthma and allergic airway inflammation (Yssel et al. Clinical and Experimental AllerD; 28, 104-109 (1998); *J* 1777771unol. 164, 59355943 (2000); Gonzalo et al. J linmunol. 165, 499-508 (2000)), Alzheimer's disease (Xia et al. J. Neurovirologv 5, 32-41 (1999)) and Arthritis (Nanlci et al. J. Immunol. 164, 5010-5014 (2000)).

Pharmaceutical Compositions

In one embodiment, pharmaceutical compositions including at least one compound of Formulas (I)-(V) are provided. In certain embodiments, at least a second active compound is included in the composition. In certain embodiments, at least a second active compound is administered in combination or alternation with the first compound. In one embodiment, the second active compound can be a chemotherapeutic, particularly an agent active against a primary tumor. In another embodiment, the second active compound can be an antiviral, particularly an agent active against a HIV and in a particular embodiment, active against HIV-1.

A host, including a human, suffering from, or at risk for, a disorder mediated by CXCR4 receptors can be treated by administering an effective amount of a pharmaceutical composition of the active compound. Specifically, a host, including a human, suffering from, or at risk of contracting, HIV or a proliferative or inflammatory disorder can be treated by administering an effective amount of a pharmaceutical composition of the active compound.

The compound is conveniently administered in unit any suitable dosage form, including but not limited to one containing 7 to 3000 mg, preferably 70 to 1400 mg of active ingredient per unit dosage form. A oral dosage of 50-1000 mg is usually convenient. Ideally the active ingredient should be administered to achieve peak plasma concentrations of the active compound of from about 1 uM to 100 mM or from 0.2 to 700 uM, or about 1.0 to 10 uM.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or antiviral compounds, or with additional chemotherapeutic agents. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation. If administered intravenously, preferred carriers are physiological saline or phosphate buffered saline (PBS).

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

Combination and Alternation Therapy

In one embodiment, the compounds described herein are administered in combination or alternation with another active compound.

In one embodiment, the active compound is a compound that is used as a chemotherapeutic. The compound provided in combination or alternation can, for example, be selected from the following list:

| | | | |
|---|---|---|---|
| 13-cis-Retinoic Acid | 2-Amino-6-Mercaptopurine | 2-CdA | 2-Chlorodeoxyadenosine |
| 5-fluorouracil | 5-FU | 6 - TG | 6 - Thioguanine |
| 6-Mercaptopurine | 6-MP | Accutane | Actinomycin-D |
| Adriamycin | Adrucil | Agrylin | Ala-Cort |
| Aldesleukin | Alemtuzumab | Alitretinoin | Alkaban-AQ |
| Alkeran | All-transretinoic acid | Alpha interferon | Altretamine |
| Amethopterin | Amifostine | Aminoglutethimide | Anagrelide |
| Anandron | Anastrozole | Arabinosylcytosine | Ara-C |
| Aranesp | Aredia | Arimidex | Aromasin |
| Arsenic trioxide | Asparaginase | ATRA | Avastin |
| BCG | BCNU | Bevacizumab | Bexarotene |
| Bicalutamide | BiCNU | Blenoxane | Bleomycin |
| Bortezomib | Busulfan | Busulfex | C225 |
| Calcium Leucovorin | Campath | Camptosar | Camptothecin-11 |
| Capecitabine | Carac | Carboplatin | Carmustine |
| Carmustine wafer | Casodex | CCNU | CDDP |

-continued

| | | | |
|---|---|---|---|
| CeeNU | Cerubidine | cetuximab | Chlorambucil |
| Cisplatin | Citrovorum Factor | Cladribine | Cortisone |
| Cosmegen | CPT-11 | Cyclophosphamide | Cytadren |
| Cytarabine | Cytarabine liposomal | Cytosar-U | Cytoxan |
| Dacarbazine | Dactinomycin | Darbepoetin alfa | Daunomycin |
| Daunorubicin | Daunorubicin hydrochloride | Daunorubicin liposomal | DaunoXome |
| Decadron | Delta-Cortef | Deltasone | Denileukin diftitox |
| DepoCyt | Dexamethasone | Dexamethasone acetate | dexamethasone sodium phosphate |
| Dexasone | Dexrazoxane | DHAD | DIC |
| Diodex | Docetaxel | Doxil | Doxorubicin |
| Doxorubicin liposomal | Droxia | DTIC | DTIC-Dome |
| Duralone | Efudex | Eligard | Ellence |
| Eloxatin | Elspar | Emcyt | Epirubicin |
| Epoetin alfa | Erbitux | Erwinia L-asparaginase | Estramustine |
| Ethyol | Etopophos | Etoposide | Etoposide phosphate |
| Eulexin | Evista | Exemestane | Fareston |
| Faslodex | Femara | Filgrastim | Floxuridine |
| Fludara | Fludarabine | Fluoroplex | Fluorouracil |
| Fluorouracil (cream) | Fluoxymesterone | Flutamide | Folinic Acid |
| FUDR | Fulvestrant | G-CSF | Gefitinib |
| Gemcitabine | Gemtuzumab ozogamicin | Gemzar | Gleevec |
| Gliadel wafer | Glivec | GM-CSF | Goserelin |
| granulocyte colony stimulating factor | Granulocyte macrophage colony stimulating factor | Halotestin | Herceptin |
| Hexadrol | Hexalen | Hexamethylmelamine | HMM |
| Hycamtin | Hydrea | Hydrocort Acetate | Hydrocortisone |
| Hydrocortisone sodium phosphate | Hydrocortisone sodium succinate | Hydrocortone phosphate | Hydroxyurea |
| Ibritumomab | Ibritumomab Tiuxetan | Idamycin | Idarubicin |
| Ifex | IFN-alpha | Ifosfamide | IL-2 |
| IL-11 | Imatinib mesylate | Imidazole Carboxamide | Interferon alfa |
| Interferon Alfa-2b (PEG conjugate) | Interleukin - 2 | Interleukin-11 | Intron A (interferon alfa-2b) |
| Iressa | Irinotecan | Isotretinoin | Kidrolase |
| Lanacort | L-asparaginase | LCR | Letrozole |
| Leucovorin | Leukeran | Leukine | Leuprolide |
| Leurocristine | Leustatin | Liposomal Ara-C | Liquid Pred |
| Lomustine | L-PAM | L-Sarcolysin | Lupron |
| Lupron Depot | Matulane | Maxidex | Mechlorethamine |
| Mechlorethamine Hydrochlorine | Medralone | Medrol | Megace |
| Megestrol | Megestrol Acetate | Melphalan | Mercaptopurine |
| Mesna | Mesnex | Methotrexate | Methotrexate Sodium |
| Methylprednisolone | Meticorten | Mitomycin | Mitomycin-C |
| Mitoxantrone | M-Prednisol | MTC | MTX |
| Mustargen | Mustine | Mutamycin | Myleran |
| Mylocel | Mylotarg | | Navelbine |
| Neosar | Neulasta | Neumega | Neupogen |
| Nilandron | | | |
| Nilutamide | Nitrogen Mustard | Novaldex | Novantrone |
| Octreotide | Octreotide acetate | Oncospar | Oncovin |
| Ontak | Onxal | Oprevelkin | Orapred |
| Orasone | Oxaliplatin | Paclitaxel | Pamidronate |
| Panretin | Paraplatin | Pediapred | PEG Interferon |
| Pegaspargase | Pegfilgrastim | PEG-INTRON | PEG-L-asparaginase |
| Phenylalanine Mustard | Platinol | Platinol-AQ | Prednisolone |
| Prednisone | Prelone | Procarbazine | PROCRIT |
| Proleukin | Prolifeprospan 20 with Carmustine implant | Purinethol | Raloxifene |
| Rheumatrex | Rituxan | Rituximab | Roveron-A (interferon α-2a) |
| Rubex | Rubidomycin hydrochloride | Sandostatin | Sandostatin LAR |
| Sargramostim | Solu-Cortef | Solu-Medrol | STI-571 |
| Streptozocin | Tamoxifen | Targretin | Taxol |
| Taxotere | Temodar | Temozolomide | Teniposide |
| TESPA | Thalidomide | Thalomid | TheraCys |
| Thioguanine | Thioguanine Tabloid | Thiophosphoamide | Thioplex |

| | | | |
|---|---|---|---|
| Thiotepa | TICE | Toposar | Topotecan |
| Toremifene | Trastuzumab | Tretinoin | Trexall |
| Trisenox | TSPA | VCR | Velban |
| Velcade | VePesid | Vesanoid | Viadur |
| Vinblastine | Vinblastine Sulfate | Vincasar Pfs | Vincristine |
| Vinorelbine | Vinorelbine tartrate | VLB | VM-26 |
| VP-16 | Vumon | Xeloda | Zanosar |
| Zevalin | Zinecard | Zoladex | Zoledronic acid |
| Zometa | | | |

In one embodiment, the compounds of the invention are administered in combination with another active agent. The compounds can also be administered concurrently with the other active agent. In this case, the compounds can be administered in the same formulation or in a separate formulation. There is no requirement that the compounds be administered in the same manner. For example, the second active agent can be administered via intravenous injection while the compounds of the invention may be administered orally. In another embodiment, the compounds of the invention are administered in alternation with at least one other active compound. In a separate embodiment, the compounds of the invention are administered during treatment with a chemotherapeutic, such as, for example, an agent listed above, and administration of the compounds of the invention is continued after cessation of administration of the other active compound. The compound may be administered for at least a month, at least two months, at least four, six, seven, eight, nine, ten, eleven, twelve months or more to reduce incidence of metastasis.

The compounds of the invention can be administered prior to or after cessation of administration of another active compound. In certain cases, the compounds may be administered before beginning a course of treatment for primary tumors, for example. In a separate embodiment, the compounds can be administered after a course of chemotherapy to reduce recurrence of metastatic tumors.

In another embodiment, the second active compound is a compound that is used as an anti-HIV agent, including but not limited to a nucleoside or nonnucleoside reverse transcriptase inhibitor, a protease inhibitor, a fusion inhibitor, cytokine and interferon. The compound provided in combination or alternation can, as a nonlimiting example, be selected from the following lists:

| Brand Name | Generic Name |
|---|---|
| Agenerase | amprenavir |
| Combivir | lamivudine and zidovudine |
| Crixivan | indinavir, IDV, MK-639 |
| Emtriva | FTC, emtricitabine |
| Epivir | lamivudine, 3TC |
| Epzicom | abacavir/lamivudine |
| Fortovase | saquinavir |
| Fuzeon | enfuvirtide, T-20 |
| Hivid | zalcitabine, ddC, dideoxycytidine |
| Invirase | saquinavir mesylate, SQV |
| Kaletra | lopinavir and ritonavir |
| Lexiva | Fosamprenavir Calcium |
| Norvir | ritonavir, ABT-538 |
| Rescriptor | delavirdine, DLV |
| Retrovir | zidovudine, AZT, azidothymidine, ZDV |
| Reyataz | atazanavir sulfate |
| Sustiva | efavirenz |
| Trizivir | abacavir, zidovudine, and lamivudine |
| Truvada | tenofovir disoproxil/emtricitabine |
| Videx EC | enteric coated didanosine |
| Videx | didanosine, ddI, dideoxyinosine |
| Viracept | nelfinavir mesylate, NFV |
| Viramune | nevirapine, BI-RG-587 |
| Viread | tenofovir disoproxil fumarate |
| Zerit | stavudine, d4T |
| Ziagen | abacavir |

Further active agents include: GW5634 (GSK), (+)Calanolide A (Sarawak Med.), Capravirine (Agouron), MW-150 (Medivir/Chiron), TMC125 (Tibotec), RO033-4649 (Roche), TMC114 (Tibotec), Tipranavir (B-I), GW640385 (GSK/Vertex), Elvucitabine (Achillion Ph.), Alovudine (FLT) (B-I), MIV-210 (GSK/Medivir), Racivir (Pharmasset), SPD754 (Shire Pharm.), Reverset (Incyte Corp.), FP21399 (Fuji Pharm.), AMD070 (AnorMed), GW873140 (GSK), BMS-488043 (BMS), Schering C/D (417690), PRO 542 (Progenics Pharm), TAK-220 (Takeda), TNX-355 (Tanox), UK-427,857 (Pfizer).

Further active agents include: Attachment and Fusion Inhibitors (i.e. AMD070, BMS-488043, FP21399, GW873140, PRO 542, Schering C, SCH 417690, TAK-220, TNX-355 and UK-427,857); Integrase Inhibitors; Maturation Inhibitors (i.e. PA457); Zinc Finger Inhibitors (i.e. azodicarbonamide (ADA)); Antisense Drugs (i.e. HGTV43 by Enzo Therapeutics, GEM92 by Hybridon); Immune Stimulators (i.e. Ampligen by Hemispherx Biopharma, IL-2 (Proleukin) by Chiron Corporation, Bay 50-4798 by Bayer Corporation, Multikine by Cel-Sci Corporation, IR103 combo); Vaccine-Like Treatment (i.e. HRG214 by Virionyx, DermaVir, VIR201 (Phase I/IIa)).

In one embodiment, the compounds of the invention are administered in combination with another active agent. The compounds can also be administered concurrently with the other active agent. In this case, the compounds can be administered in the same formulation or in a separate formulation. There is no requirement that the compounds be administered in the same manner. For example, the second active agent can be administered via intravenous injection while the compounds of the invention may be administered orally. In another embodiment, the compounds of the invention are administered in alternation with at least one other active compound. In a separate embodiment, the compounds of the invention are administered during treatment with an active agent, such as, for example, an agent listed above, and administration of the compounds of the invention is continued after cessation of administration of the other active compound.

The compounds of the invention can be administered prior to or after cessation of administration of another active compound. In certain cases, the compounds may be administered before beginning a course of treatment for viral infection or for secondary disease associated with HIV infections, for example. In a separate embodiment, the compounds can be administered after a course of treatment to reduce recurrence of viral infections.

Process for Identification of CXCR4 Antagonists

In a separate embodiment, a process for screening potential drug candidates is provided. The process includes providing a labeled peptide-based CXCR4 antagonist that has a detectable signal when bound to a CXCR4 receptor; contacting a CXCR4 receptor with at least one test molecule at a known concentration to form a test sample; contacting the test sample with the peptide-based antagonist; separately, contacting the peptide-based antagonist to a sample not including any test molecule to form a control sample; and comparing the signal from the test sample to the signal from the control sample. In a specific sub-embodiment, the peptide-based antagonist is derived from TN14003 (described in PCT Publication No. WO 04/087068 to Emory University). In a further subembodiment, the antagonist is labeled with a biotin molecule and the signal is elicited when the biotin-labeled antagonist is contacted with a streptavadin-conjugated signal molecule.

The signal elicited by binding of the CXCR4 antagonist and the receptor can be a fluorescent signal. In one embodiment, the signal is elicited when a second, accessory molecule is added, such as, for example, a fluorescent molecule bound to a molecule that binds the labeled antagonist molecule. In one embodiment, the antagonist molecule is labeled with biotin, and the accessory molecule is a fluorescently labeled streptavadin molecule.

The peptide-based antagonist is typically a molecule with high affinity for the receptor. In one embodiment, the molecule is derived from the "T140" peptide antagonists. In a specific embodiment, the antagonist is TN14003 (described in PCT Publication No. WO 04/087068 to Emory University). The receptor is typically expressed in a cell line. The process can be performed as a dose-response curve. In this embodiment, the test compound is incubated with the receptor at varying concentrations and the signal elicited after binding of the labeled antagonist is measured and compared to control, as well as to each other.

EXAMPLES

Example 1

Peptide-Based CXCR4 Antagonist, TN14003, is a Novel-Imaging Probe Specific for CXCR4

Initially, experiments were performed to verify that TN14003 binds to the predicted SDF-1 binding sites on the CXCR4 receptor. In these studies, MDA-MB-231 cells were incubated in the absence (FIG. 1A, B) or presence (FIG. 1A, C) of 400 ng/ml of SDF-1α for 10 min, and then fixed in ice-cold acetone. Immunofluorescence of the biotin-labeled TN14003 was negative in both membrane and cytosol in the cells pretreated with SDF-1α for 10 min (FIG. 1A, C).

The utility of the biotinylated TN14003 as a probe of CXCR4 was explored coupled with immunofluorescence staining of cultured breast cancer cells and paraffin-embedded tissues from breast cancer patients. MDA-MB-231 had high levels of mRNA and protein for CXCR4 as shown by Northern blots and Western blots relative to MDA-MB-435 (FIG. 1B). When the biotinylated TN14003 was used to stain the two cell types, the high CXCR4-expressing MDA-MD-231 cells were brightly stained (FIG. 1C left), whereas the low CXCR4-expressing MDA-MB-435 was less (FIG. 1C right) consistent with the low surface CXCR4 expression in these cells.

Immunofluorescence staining with the biotinylated TN14003 on cancer patients' paraffin-embedded tissue sections demonstrated that TN14003 could be used to detect CXCR4 receptors on tumor cells from the archived paraffin-embedded tissue sections (FIG. 1D). A total of 41 patient tissues provided by Avon Tissue Bank for Translational Genomics Research at Grady Memorial Hospital in Atlanta, Ga., were stained and 0 out of 4 normal breast tissues, 9 out of 12 Ductal Carcinoma in situ (DCIS), and 23 out of 25 node-positive cases were positive for CXCR4. Many samples carrying the diagnoses of DCIS already acquired CXCR4 overexpression (FIG. 1D).

Example 2

TN14003 is a More Potent Inhibitor of CXCR4-Associated Signaling than AMD3100

Figure 2:
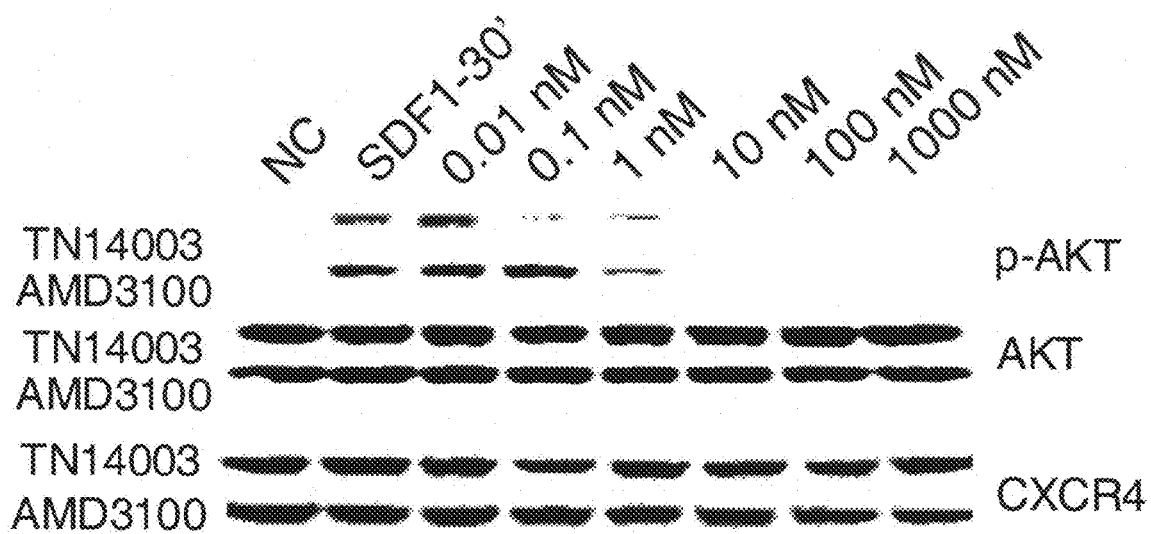
FIG. 2 is an image of a western blot showing phosphorylation of Akt. Incubating MDA-MB-231 cells with 100 ng/ml of SDF-1 for 30 min stimulated phosphorylation of Akt. This activation was blocked with TN14003 or AMD3100 in a dose-dependent manner.

CXCR4/SDF-1 interaction activates PI3K/Akt and Ras/Raf/MEK/Erk pathways in a $G\alpha_i$ protein (PTX-sensitive)-dependent manner. Experiments were conducted to determine the effect of blocking CXCR4/SDF-1 interaction by either TN14003 or AMD3100 at different concentrations (0, 0.01, 0.1, 1, 10, 100, 1000 nM) on phosphorylations of Akt and Erk1/2 signaling. Incubating cells with 100 ng/ml of SDF-1 for 30 minutes activated Akt. Akt activation was blocked by either sub-nano molar concentration of TN14003 or a few nano molar AMD3100 (FIG. 2). Erk1/2 phsophorylation was attenuated in the presence of sub-nano molar concentration of TN14003 or 100 nM AMD3100 (data not shown). However, the increase in Erk1/2 phosphorylation by SDF-1 was not significant as the increase in Akt phosphorylation. The results demonstrate that TN14003 is more potent than AMD3100 in inhibiting CXCR4-mediated signaling. Treating cells with SDF-1, TN14003, or AMD3100 did not affect CXCR4 protein levels.

Example 3

Knock Down of CXCR4 by siRNA Blocks Metastasis in the Lung

RNA interference technology, silencing targeted genes in mammalian cells, has become a powerful tool for studying gene function. Two different siRNA duplexes of CXCR4 (Genbank Accession no. NM_003467), siRNA1 (sense, 5'-UAAAAUCUUCCUGCCCACCdTdT-3') (SEQ. ID No. 1) and siRNA2 (sense, 5'-GGAAGCUGUUG-GCUGAAAAdTdT-3') (SEQ. ID No. 2) were designed and purchased from Dharmacon (Lafayette, Colo.). The non-specific control siRNA duplexes were purchased from Dharmacon with the same GC content as CXCR4 siRNAs (42%, D001206-10).

Figure 3:
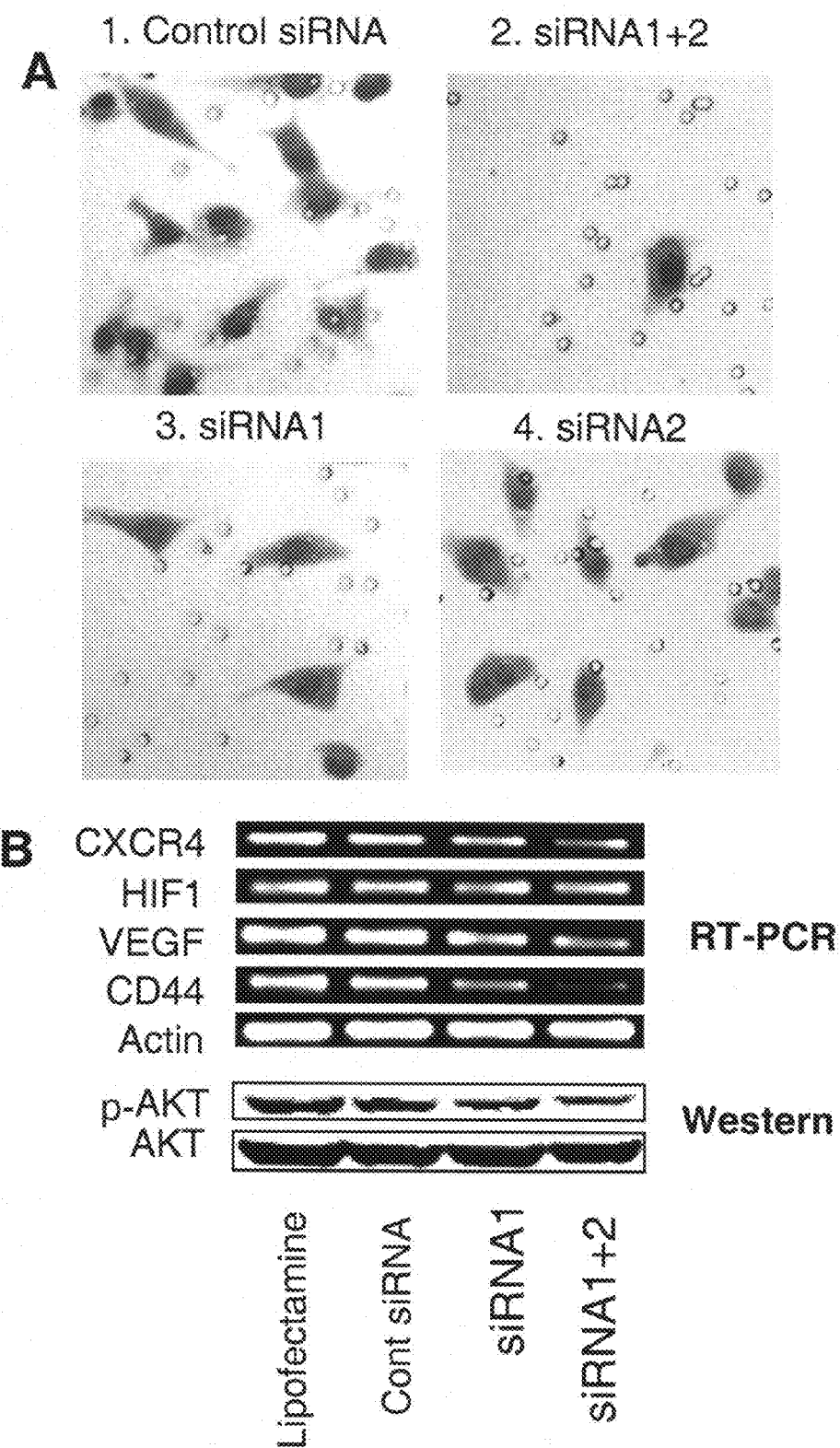
FIG. 3 shows images of stained cells and blots showing invasion of MDA-MB-231 cells transfected with CXCR4 siRNAs. A: H&E staining of invasion of MDA-MB-231 cells transfected with control siRNA, siRNA1 alone, or siRNA2 alone in matrigel invation assay. The invasiveness of MDA-MB-231 cells transfected with siRNA1+2, siRNA1 and siRNA2 relative to the control are 16% (P<0.0003), 39% (P<0.0014) and 51% (P<0.0026) respectively. B: VEGF, HIF-1 and CD44 mRNA levels. Actin was used as a loading control.

Lowering CXCR4 mRNA levels by siRNAs inhibited CXCR4/SDF-1-mediated invasion as measured by a matrigel invasion assay. The CXCR4 ligand, SDF-1 (400 ng/ml) was added to the lower chamber to attract CXCR4-positive breast cancer cells to migrate through the matrigel. The invasion of MDA-MB-231 cells transfected with siRNA1 decreased to 39±4% of the control cells, 51±8% with siRNA2, and only 16±6% with both siRNA1+2 (FIG. 3A). FIG. 3B shows that lowering CXCR4 influenced the mRNA levels of VEGF and CD44 without affecting mRNA levels of HIF-1α.

To determine whether lowering CXCR4 levels in MDA-MB-231 cells blocks lung metastasis in the experimental animal model, MDA-MB-231 cells were transfected with various combination of CXCR4 siRNAs and injected into the female SCID mice through the tail vein twice weekly intravenously by themselves (without liposome) following the injection of tumor cells (Groups 2-4). Forty-five days after the tumor cell injection, all animals in the control group (Group 1) developed lung metastases. In contrast, only one animal in Group 2 developed metastases and these were barely visible. A representative picture of lungs in FIG. 4A demonstrated grossly cystic lung micro-metastasis in the control group. On the other hand, three representative pictures of lungs from three treated groups showed significantly fewer visible lung metastases, most notably in Groups 2 and 3. The H&E staining of the lung tissues from Group 2 showed the morphology of normal lung, while that from the control group showed invading tumor cells (FIG. 4A).

Figure 4:
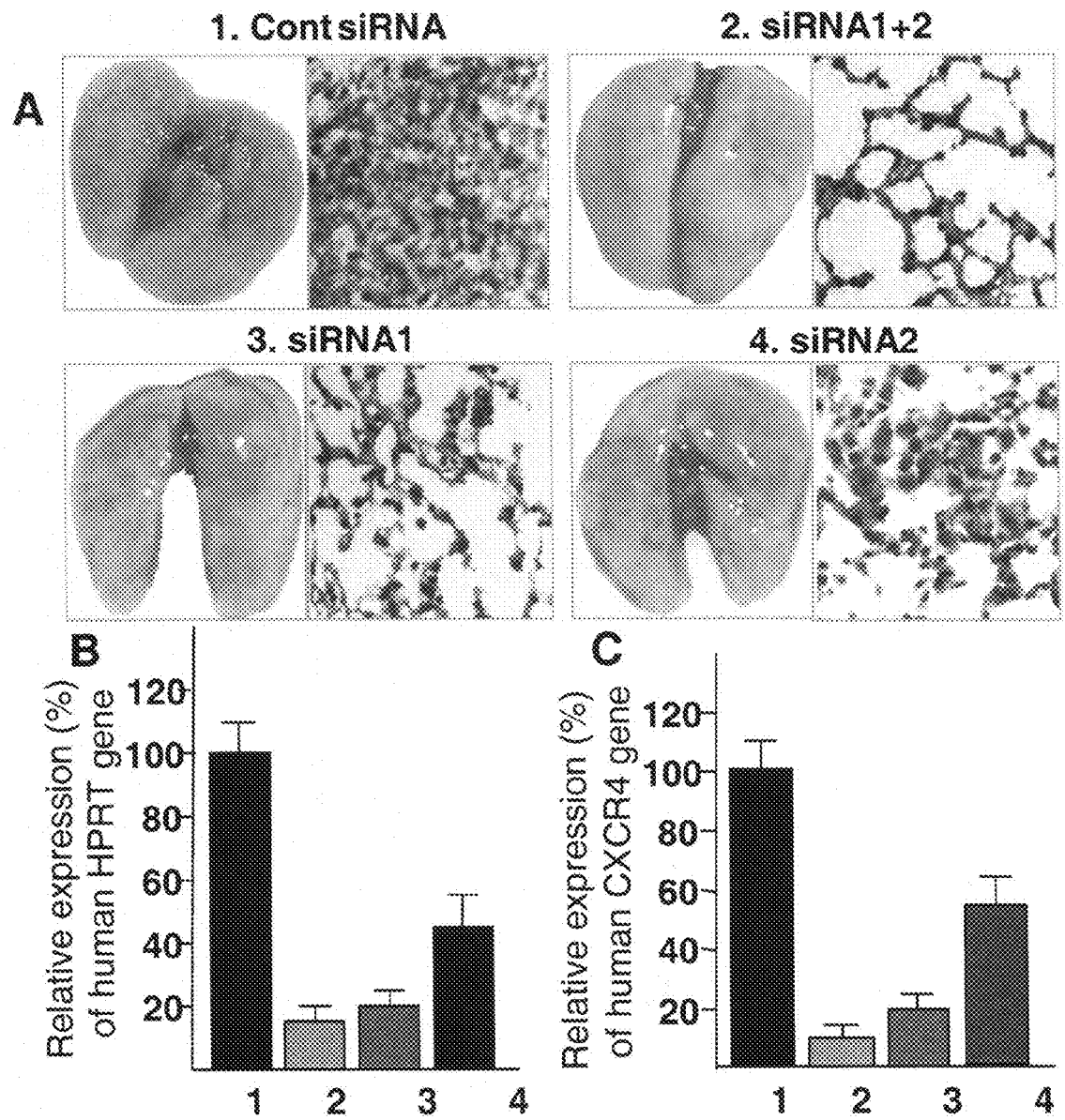
FIG. 4 shows images of cells and lungs, as well as graphs of the effect of CXCR4 siRNAs on inhibition of breast cancer metastasis in vivo. A: The photographs of lungs and their H&E stainings of one representative from each group. B: The average real-time PCR (RT-PCR) of hHPRT using primers that only recognize human cells from siRNA-treated groups relative to that of control group. 1: Group 2; 2: Group 2; 3: Group 3; 4: Group 4. C: The percentage of human CXCR4 average expression level of each treated group is relative to that of control group.
Figure 5:
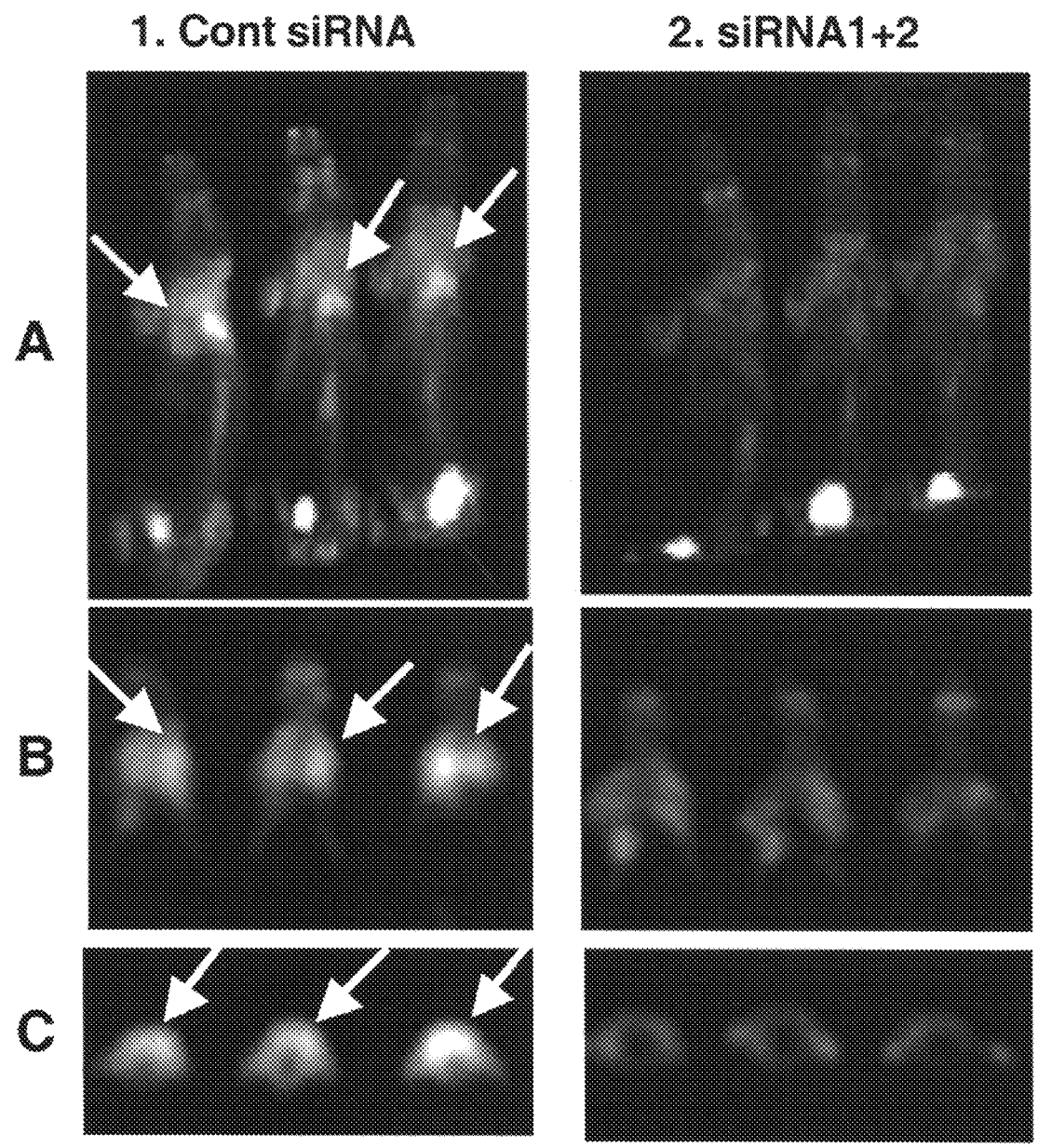
FIG. 5 shows representative images of FDG-PET of animals in Group 1 (control siRNA) and Group 2 (siRNA1+2) indicating the effect of CXCR4 siRNAs on inhibition of breast cancer metastasis in vivo. A: The maximum intensity projection of 6 representative mice from Group 1 (left 3 mice) and Group 2 (right 3 mice). B: Coronal sectional images from the lung area from the same animals in A. C: The transaxial sectional images from the lung area from the same animals in A.

These results were further confirmed by semi-quantitative real-time RT-PCR using primers for the human housekeeping gene hHPRT that do not cross-react with its mouse counterpart (FIG. 4B). Real-time RT-PCR analyses showed high expression of hHPRT mRNA in metastasis-infiltrated lungs of the SCID mice in the control group. The expression levels of human HRPT in the lungs of mice in Groups 2 and 3 were significantly lower than that of control group (FIG. 4B). There was high CXCR4 expression in the control group mouse lungs and much lower CXCR4 expression in the lungs of the treated group mice (FIG. 4C). MicroPET imaging with FDG was utilized to detect lung metastases in mice in Groups 1 and 2. FIG. 5 shows representative FDG-PET images confirming lung metastasis in the control group and significantly fewer lung metastases in Group 2. FIG. 5A is a maximum intensity projection (three-dimensional) generated from three representative mice in Group 1 (control). The chest area is significantly brighter in each mouse of the control group (left) than any of the mice in the siRNA1+2 treated group (right). The high FDG-uptake can also be seen in the bladder due to the secretion of FDG. FIGS. 5B and 5C are selected coronal and transaxial section images, respectively. The maximum standardized uptake values ($SUV_{max}$) of the lung area in FIG. 5 were 8.6, 7.1, 9.3, 2.2, 2.5, and 2.1. Collectively, these images show that FDG uptake is much higher in lungs from the control group (left) than siRNA1+2 treated group (right), which correlates with increased lung metastases in the control group than the siRNA1+2 treated group.

Example 4

VEGF Promotor Regulation by CXCR4 and HIF-1α

Figure 6:
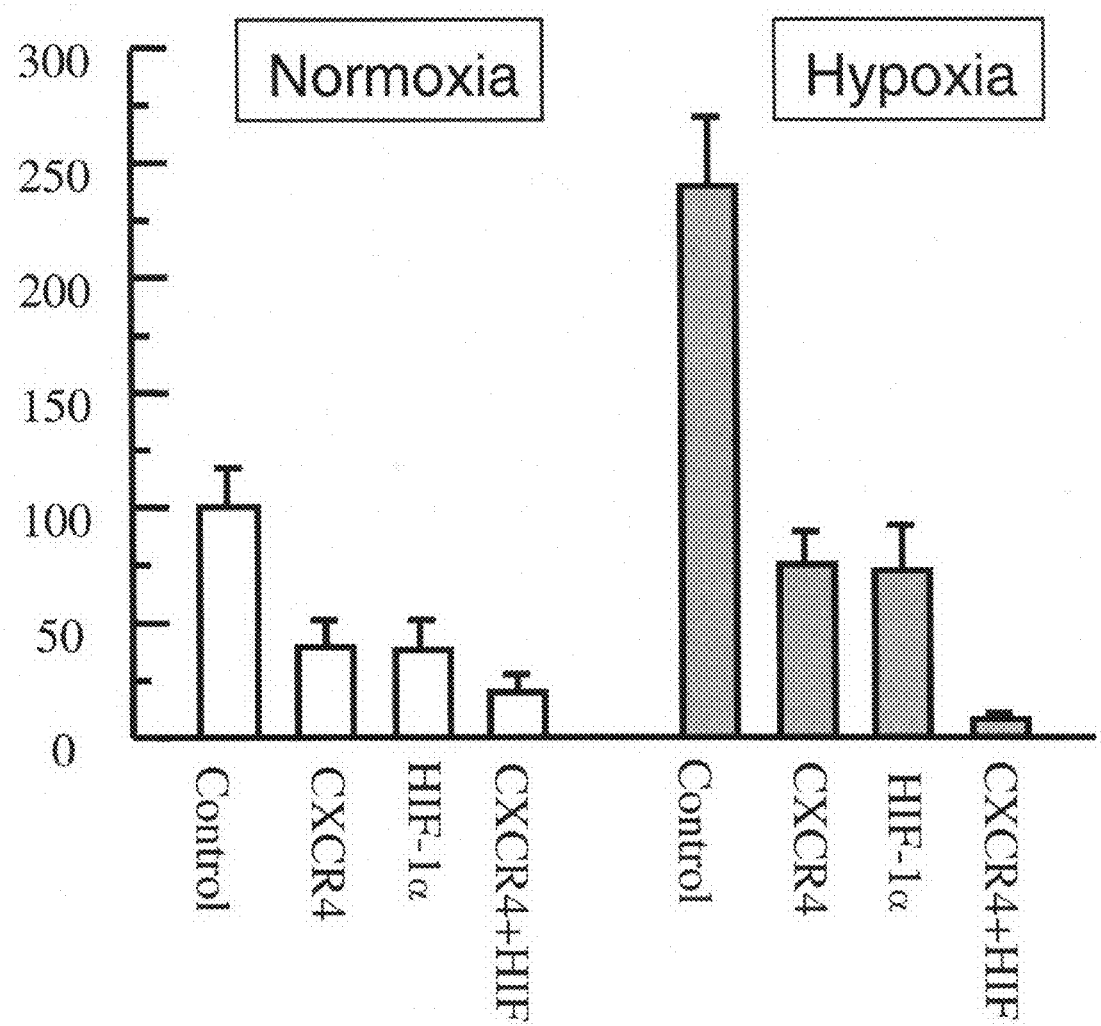
FIG. 6 is a graph of HRE activity. The graph shows that HRE-Luc MB-231 cells have moderately high HRE activity in normoxia that can be suppressed by either CXCR4 siRNA or HIF-1 siRNA. HRE acitivity increase 2.5 fold in hypoxia that can also be suppressed by either CXCR4 siRNA or HIF-1 siRNA.

To determine whether lowering CXCR4 levels might affect VEGF transcription compared to HIF-1α the hypoxia-reporting luciferase/LacZ plasmid from Dr. Van Meir's laboratory was used as a reporter system to detect hypoxia-responsive element (HRE) of VEGF promoter activity (Post, D. E. and Van Meir, E. G. (2001) *Gene Ther* 8: 1801-1807). The sequence of HIF-1α siRNA was 5'-UUCAAGUUGGAA-UUGGUAGdTdT-3' (SEQ. ID No. 3). Pooled cell clones were created with MDA-MB-231 cells stably transfected with this plasmid (called HRE-Luc MB-231). Unexpectedly, HRE activity in normoxia was moderately high in MDA-MB-231 cells that have high CXCR4 levels in normoxia (FIG. 6, left), which was not observed in other cell lines with low CXCR4 and HIF-1 levels (LN229, U87, 9L, and MDA-MB-435). This moderately high HRE activity in MDA-MB-231 cells was suppressed by CXCR4 siRNA or HIF-1α siRNA. The HRE activity significantly decreased with the combination treatment of CXCR4 siRNA and HIF-1α siRNA for 48 hours. As expected, the HRE activity increased 2.5-fold by hypoxia treatment (1% oxygen and 5% $CO_2$ in nitrogen). This elevated HRE activity was again suppressed by siRNA for CXCR4 or HIF-1α (FIG. 6, right).

Example 5

Screening of Novel Anti-CXCR4 Small Molecule by Competition Assay Using Biotin-Labeled TN14003 (Peptide-Based)

The molecular dynamic simulations of the rhodopsin-based homology model of CXCR4 shows that AMD3100 is a weak partial agonist because it interacts with CXCR4/SDF-1 binding by two aspartic acids while the peptide-based CXCR4 antagonist, T140 (similar to TN14003) strongly binds the SDF-1 binding site of CXCR4 in extracellular domains and regions of the hydrophobic core proximal to the cell surface (Trent, et al. (2003) *J Biol Chem* 278: 47136-47144). This structural information was used to create a library of compounds with multiple nitrogens throughout the molecular framework, but structurally different from AMD3100.

Figure 7:
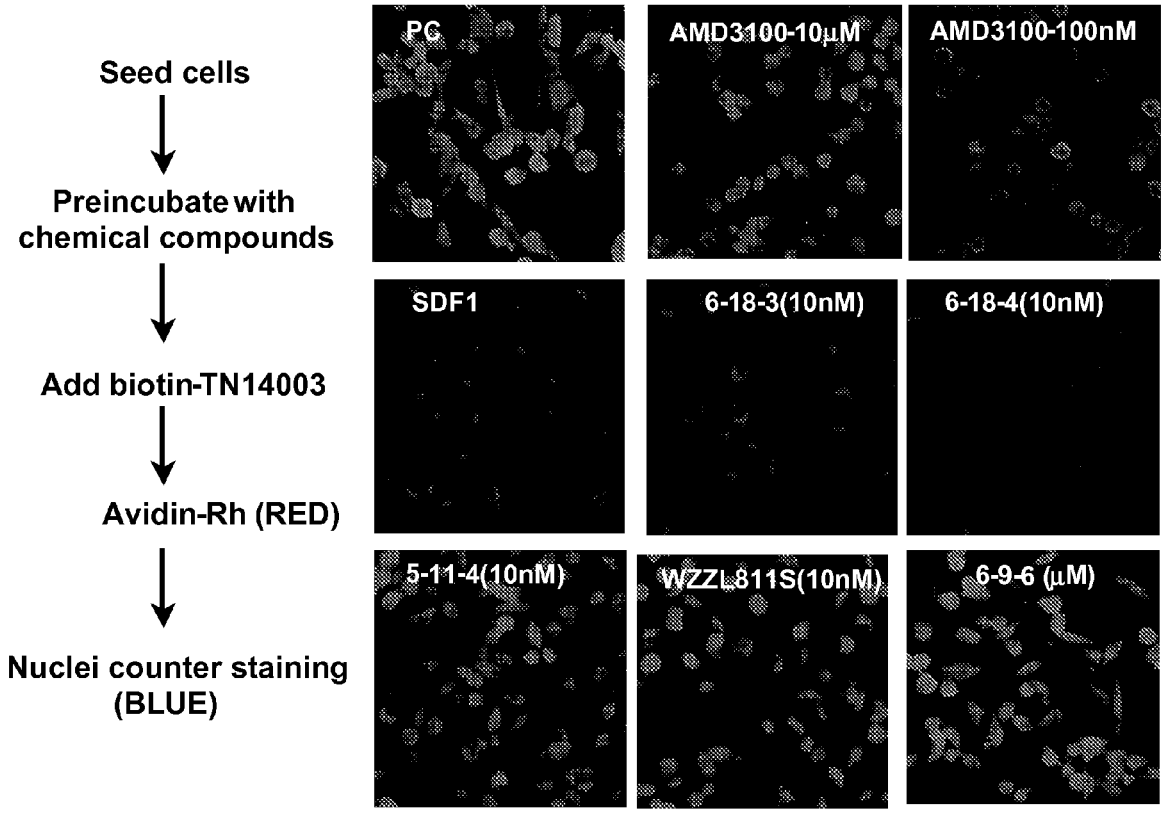
FIG. 7 shows images of cells showing a drug screen methodology utilizing biotin-labeled TN14003 as a reporter.
Figure 8:
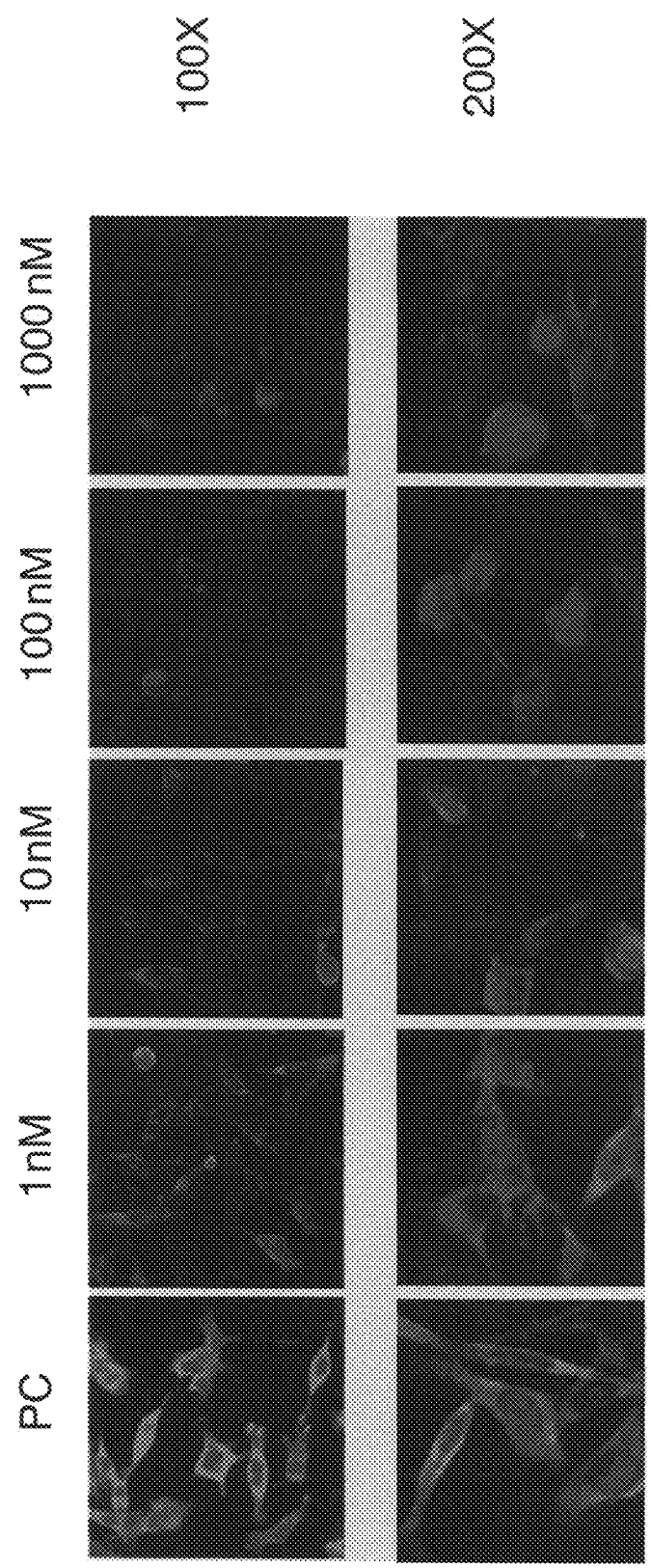
FIG. 8 shows images of stained cells. Biotin-labeled TN14003 was used to detect CXCR4 protein from the cells pre-incubated with various concentrations of WZZL811S. Results indicate that IC50 of WZZL811S is less than 1 nM.
Figure 9:
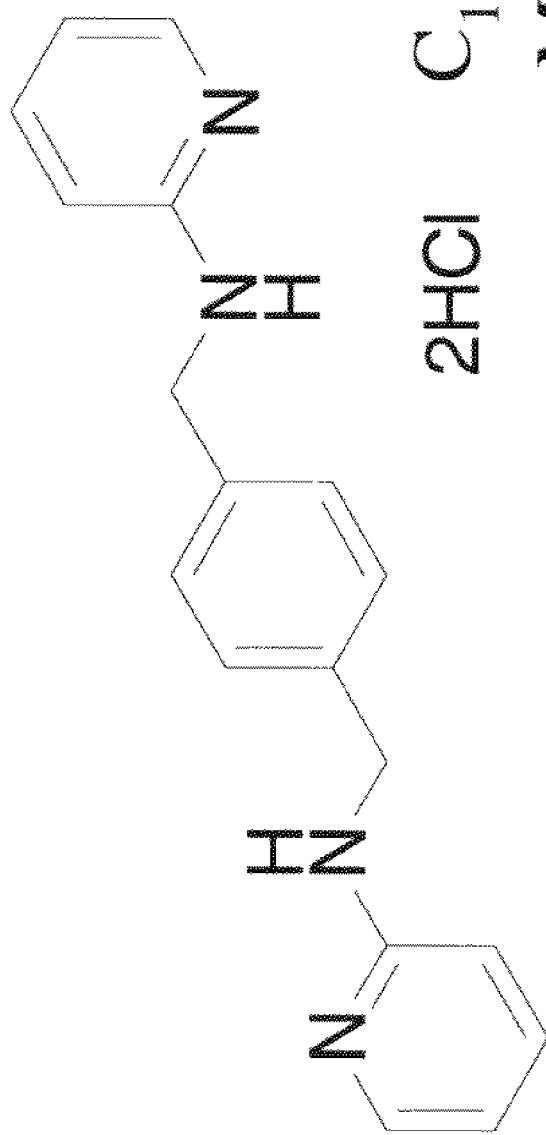
FIG. 9 shows the chemical structure of WZZL811S.

Using biotin-labeled TN14003 along with streptavidin-conjugated rhodamine allowed a determination of the binding efficiency of these chemicals to the SDF-1 binding site of CXCR4 on tumor cells and compared it to AMD3100-SDF-1 interactions (FIG. 7). The cells incubated with compounds with high affinities for the ligand-binding site showed only blue nuclei staining, whereas compounds with low affinity resulted in both CXCR4 in red (rhodamine) and blue nuclei staining Cells were pre-incubated with different concentrations of AMD3100. The results indicated that 10 μM concentration was needed for AMD3100 to compete against biotin-labeled TN14003. On the other hand, some candidate compounds were as potent as TN14003 at very low concentrations. Therefore, one of these compounds, WZZL811S, was selected to study its therapeutic potential based on potency and low toxicity to cells (FIG. 9). FIG. 8 shows the binding affinity of WZZL811S to the ligand-binding site (approximately the same as TN14003 binding site) of CXCR4 on tumor cells at nano-molar concentration. WZZL811S did not decrease cell viability of MDA-MB-231 cells even at 100 μM (the highest concentration tested).

Example 6

Figure 10:
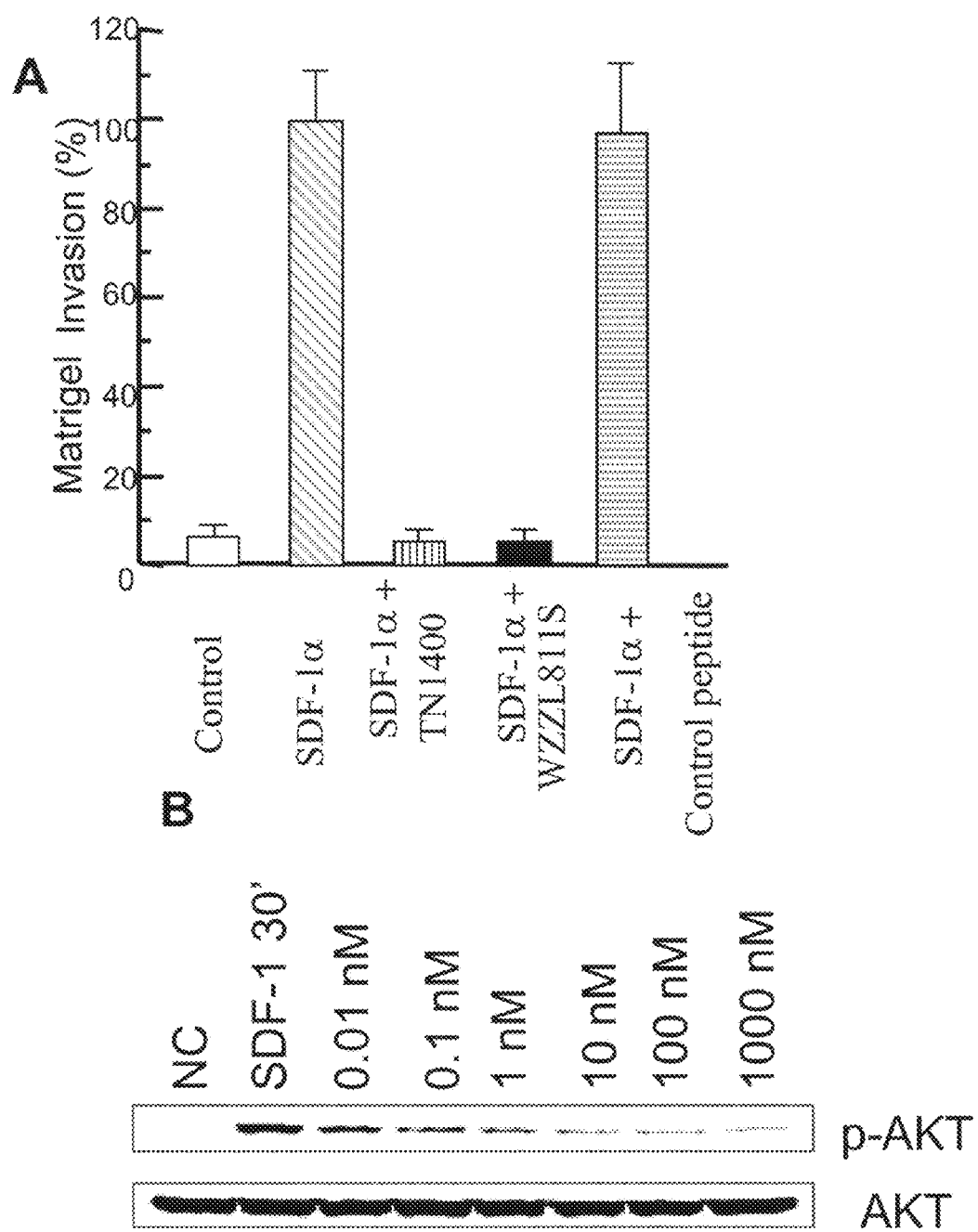
FIG. 10 is a graph and representative blot of matrigel invasion and Akt phosphorylation in cells. A: Inhibition of CXCR4/SDF-1 mediated invasion of MDA-MB-231 in vitro by WZZL811S. CXCR4/SDF-1 mediated invasion of MDA-MB-231 was blocked by 2 nM of either TN14003 or WZZL811S. B: Incubating MDA-MB-231 cells with 100 ng/ml of SDF-1 for 30 min stimulated phosphorylation of Akt that was blocked by WZZL811S in a dose-dependent manner.

WZZL811S Inhibits CXCR4/SDF-1-Mediated Matrigel Invasion and CXCR4/SDF-1-Mediated Akt Activation WZZL811S was tested in a matrigel invasion assay to determine whether it can inhibit CXCR4/SDF-1-mediated invasion. As shown in FIG. 10A, WZZL811S was as potent as TN14003 in blocking SDF-1-induced invasion at the same concentration (2 nM). FIG. 10B shows that WZZL811S blocked SDF-1/CXCR4-induced Akt phosphorylation in a dose-dependent manner.

Example 7

Animal Models

An experimental animal model was developed for metastasis by injecting MDA-MB-231 cells through the tail vein.

Figure 11:
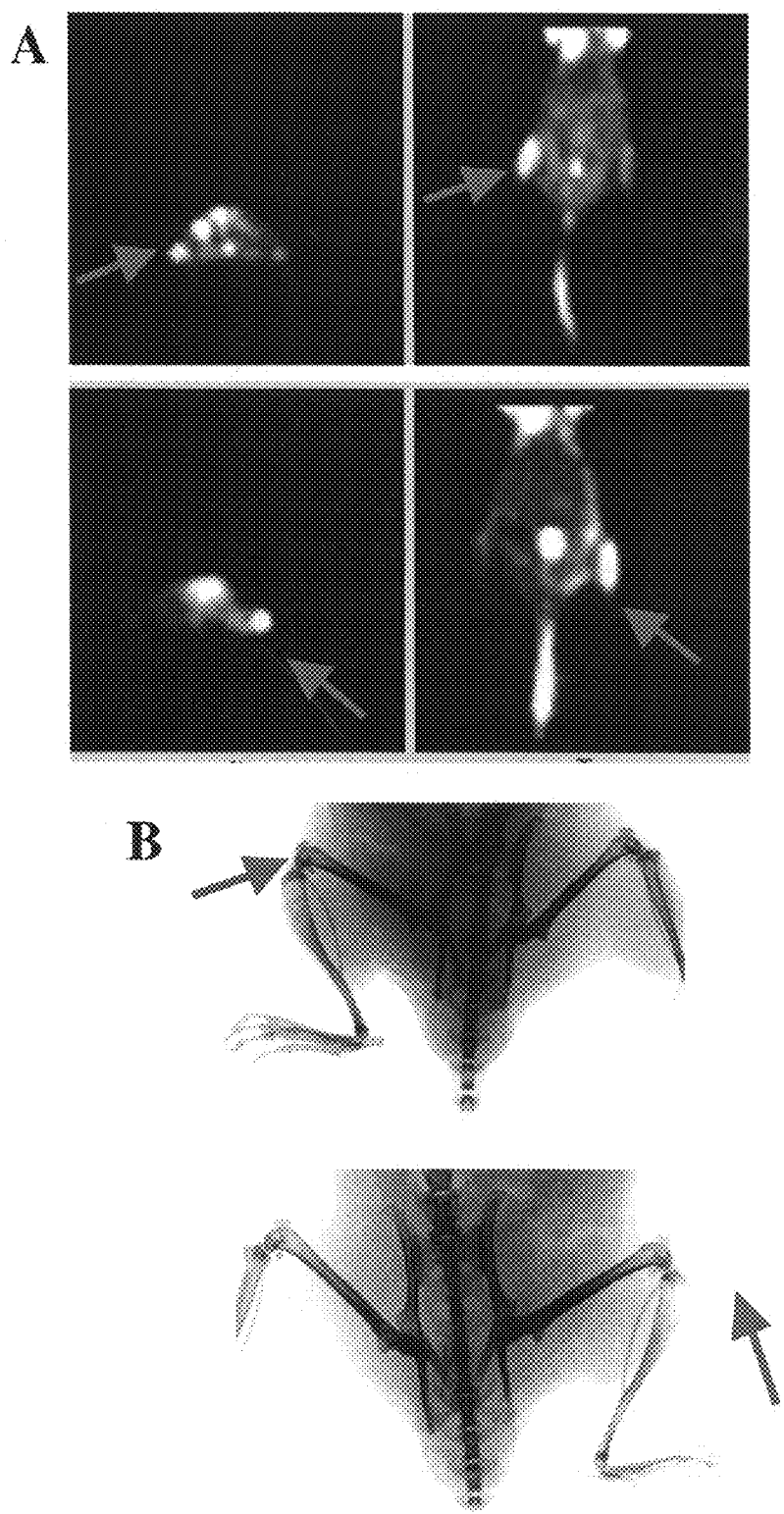
FIG. 11 shows X-ray images of mice showing bone metastasis of MDA-MB-231 cells. A: FDG-PET (left, transacial; right coronal). B: X-ray mammography. The animal xenograft was generated by injecting tumor cells intra-tibia.

Over 90% of the animals developed lung metastasis in 45 days. Another experimental animal model for metastasis was generated by injecting tumor cells intra-tibia. About 50% of animals developed bone metastasis in 45 days. FDG-PET clearly shows the lung metastasis (FIG. 5) and the bone metastasis (FIG. 11) developed from our MDA-MB-231 cells.

Figure 12:
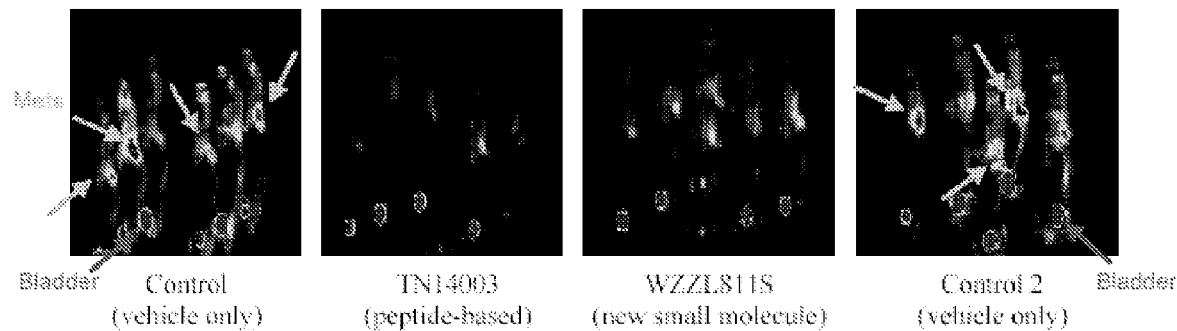
FIG. 12 shows FDG-PET images of mice animals described in Example 7.

The metastatic 686LN cells were injected intravenously through the tail vein to generate experimental animal models for Head & Neck cancer metastasis, modulated via CXCR4. Thirty days later, these metastatic cells metastasized to lungs, liver, and bone marrow in control group (vehicle treated) while they failed to metastasize to any organs in peptide-based CXCR4 antagonist, TN14003 (20 mg/mouse/twice weekly), treated group determined by non-invasidve [$^{18}$F]-fluorodeoxyglucose Positron Emission Tomography (FDG-PET) (FIG. 12). Each panel shows FDG-PET image of 6 mive and large lung metastases are indicated by green arrows (bladder shows high FDG-uptake due to excretion, not tumor related). These 3-D projection images show lung metastases well (bone mets and liver mets were apparent in axial section images of mice in control groups, data not shown). The small molecular anti-CXCR4 compound WZZL811S (20 mg/mouse/twice weekly) showed 80% efficacy of TN14003, potentially due to shorter half-life of the compound.

Example 8

Pharmacokinetics of a Novel Anti-Hif1α Compound

Figure 13:
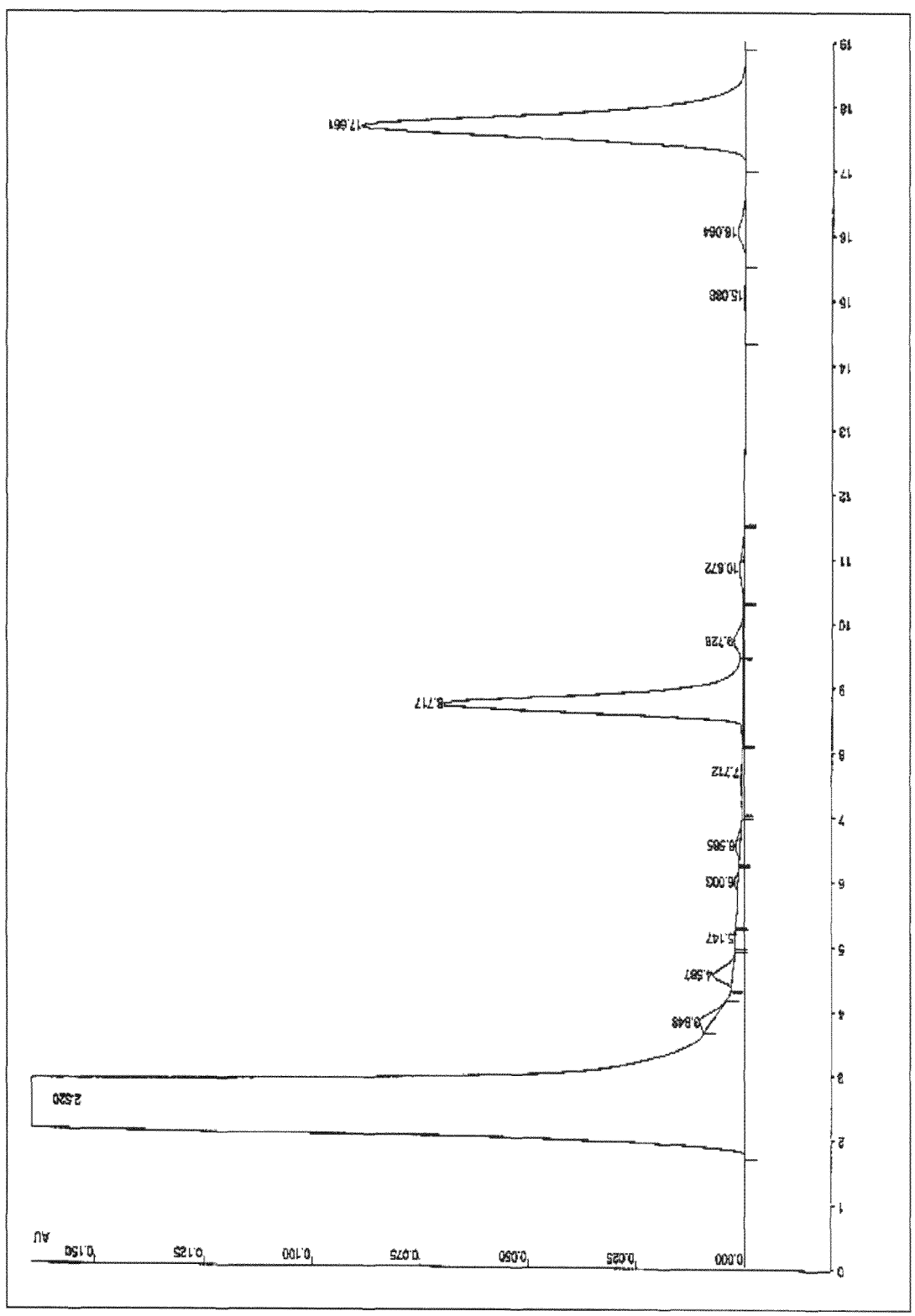
FIG. 13 is a graph of the HPLC analysis performed as described in Example 8.
Figure 17:
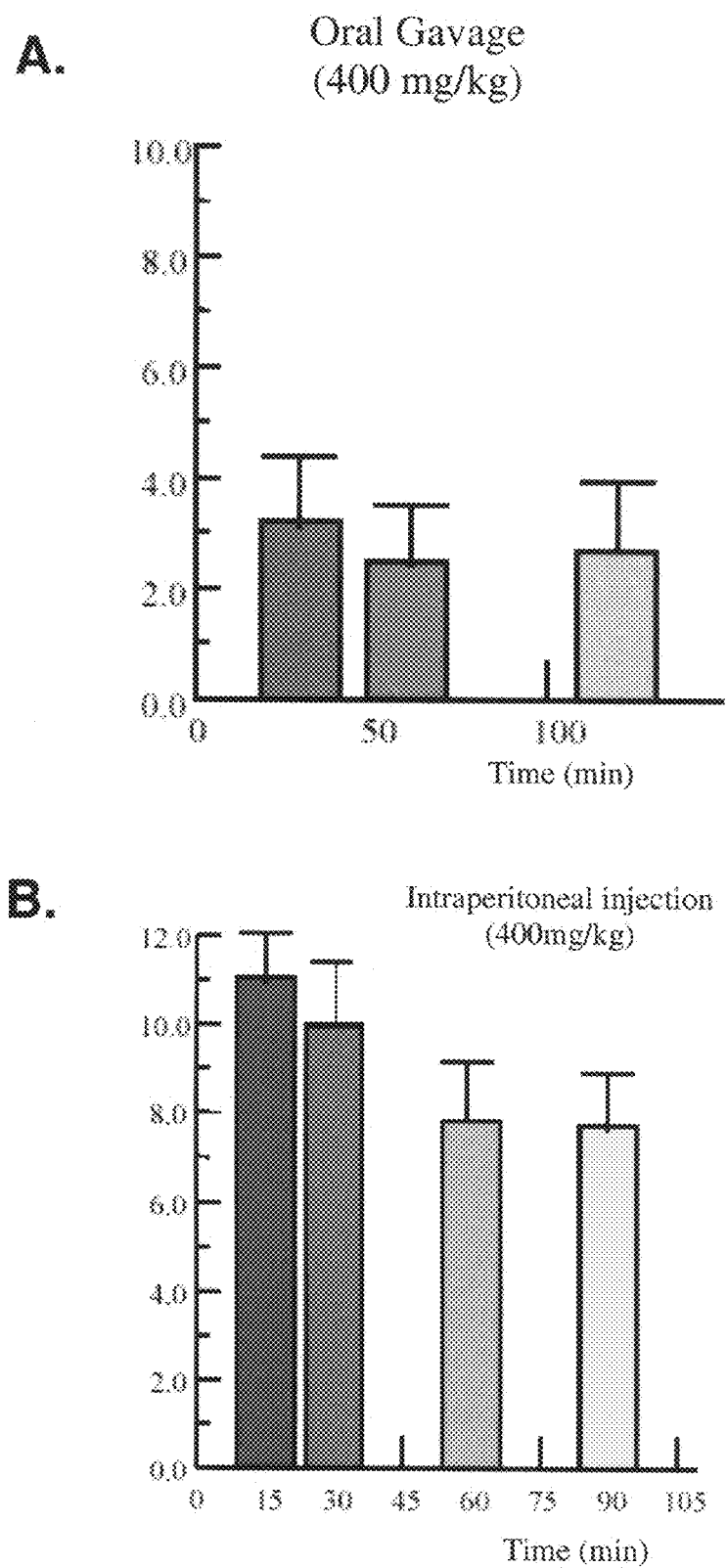
FIG. 17 is graphs of the amount of WZZL811S measured at indicted times after systemic administration, indicating the in vivo stability of WZZL811S and WZ40. A) is a graph of the levels of WZZL811S at indicated times after administration of 400 mg/kg compound by oral gavage. B) is a graph of the levels of WZ40 at 15, 30, 60 and 90 minutes after intraperitoneal injection of 400 mg/kg.

A pharmacokinetic study of a novel anti-HIF-1α small molecule was performed. A stably integrated hypoxia-reporter system of glioma cells transfected with the hypoxia-reporting plasmid (described above) was utilized. A natural product-like small molecule library of 10,000 compounds was screened and the "best hit" was identified. HPLC methodology was developed for quantitatively detecting KCN-1 in plasma and other biological samples. For the pharmacokinetic study, KCN-1 (100 mg/kg) was dissolved in DMSO and administered intravenously to mice. Plasma samples were collected at given time points (0.25, 0.5, 1, 2, 4 and 8 h) and KCN-1 levels were quantified by HPLC. The HPLC system consisted of a Varian Prostar gradient pump, a Prostar autosampler and a Prostar photo diode array detector. The column was a Luna 5μ C18 column (4.6 mm×250 mm, Phenomenex). The retention time of KCN1 and the internal standard were 8.7 and 17.7 min, respectively (FIG. 13). The in vivo stability of WZZL811S and WZ40 were measured after systemic administration of compounds over two hours (FIG. 17).

Example 9

Endothelial Capillary Tube Formation Assay

Figure 14:
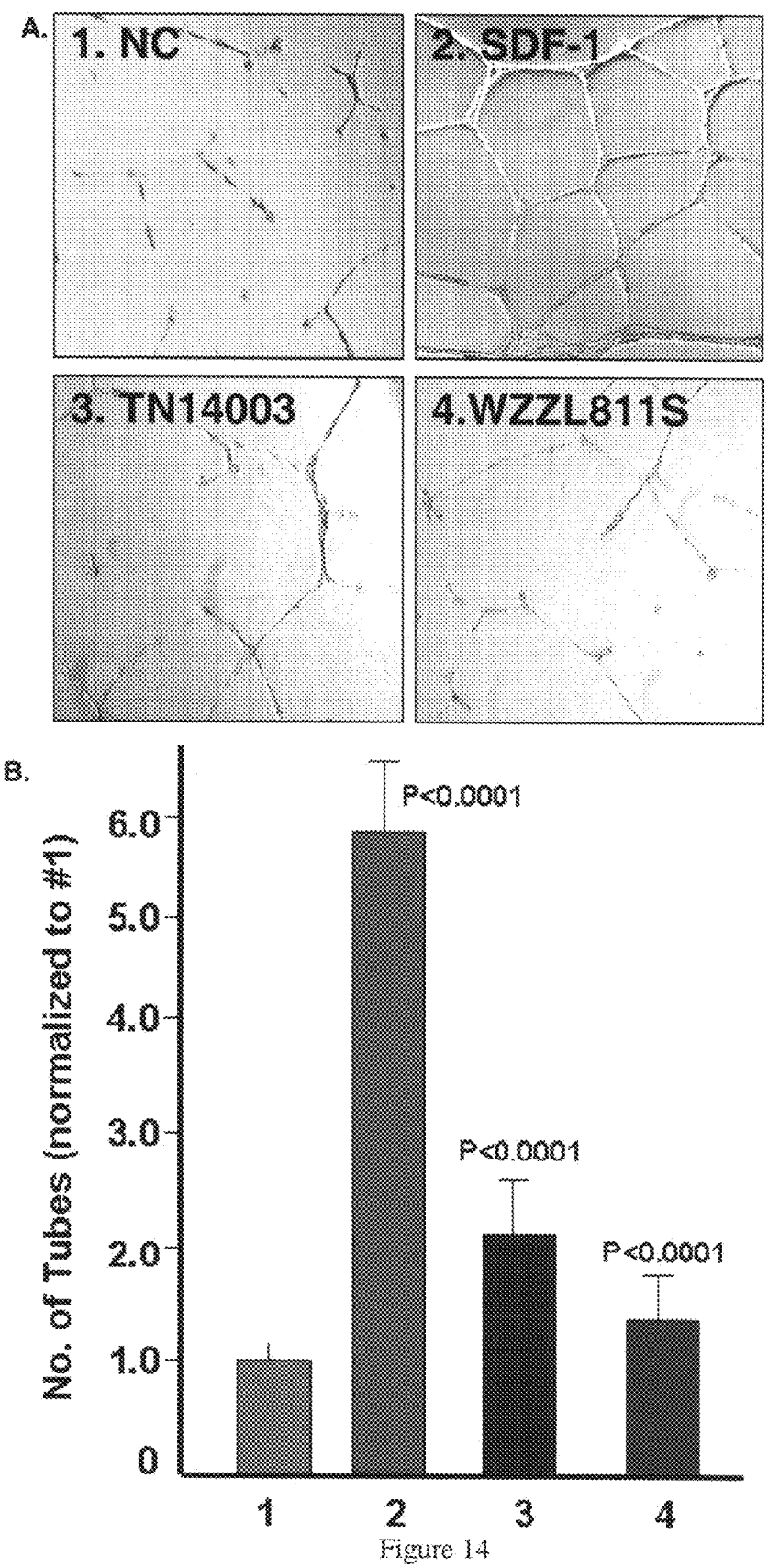
FIG. 14 shows images and a graph of endothelial capillary tube formation assay. A) is micrographs of endothelial cell tube formation. B) is a graph of the number of tubes in each treatment group.

The anti-angiogenic effect of test compounds was measured by analyzing endothelial cell growth and tube formation. The angiogenic effect of SDF-1 (100 ng/ml) on capillary formation by human umbilical vein endothelial cells (HUVECs) was examined in vitro using Matrigel-coated 24-well plates precoated with Matrigel and incubated for 18 hours. The angiogenic effect of SDF-1 was inhibited by either 100 nM TN14003 (peptide-based CXCR4 antagonist) or WZZL811S treatment (FIG. 14a, graph FIG. 14b). FIG. 14B shows a graphical analysis of the number of endothelial cell tubes normalized to control (NC).

Example 10

Efficacy in a Model of HIV

Figure 15:
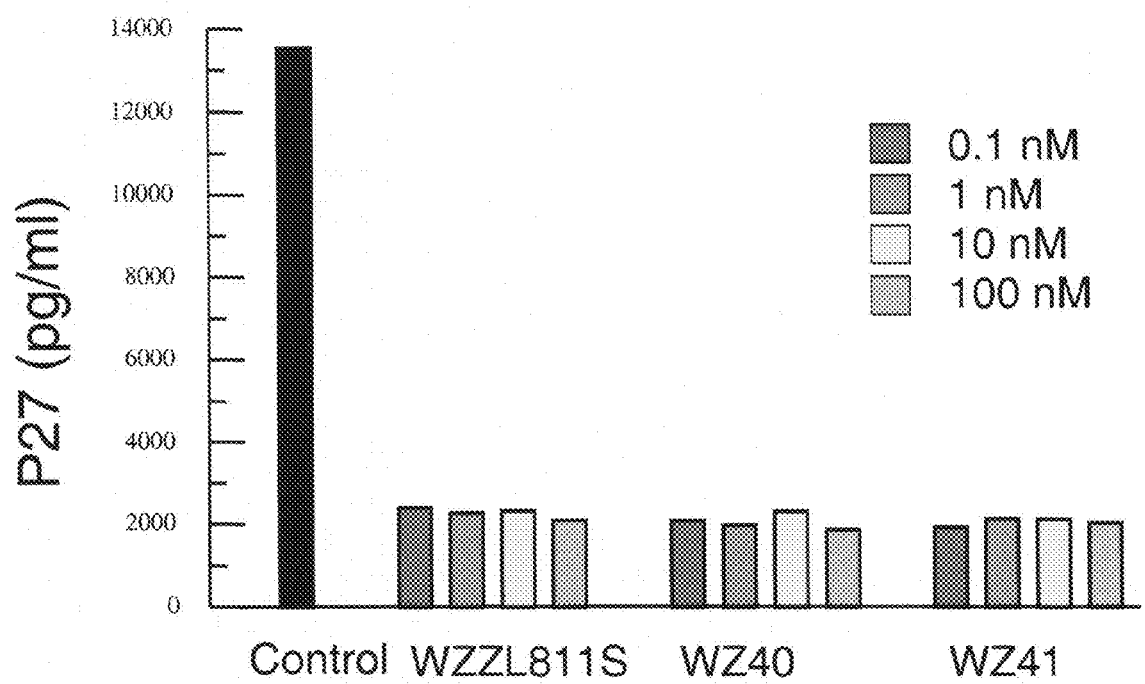
FIG. 15 is a graph of p27 levels measured after incubation with indicated amounts of WZZL811S, WZ40 or WZ41S.
Figure 16:
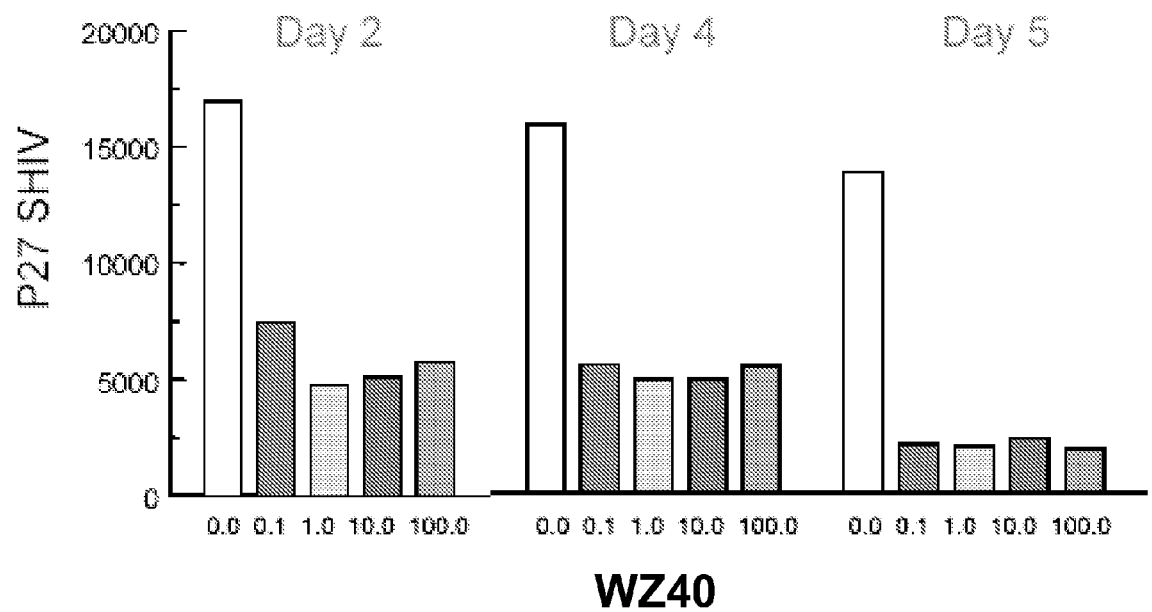
FIG. 16 is a graph of p27 levels measured after incubation with indicated amounts of WZ40 and infection with SHIV for 2, 4 or 5 days.

The effect of the test compounds on HIV infection in model cells was analyzed by p27 antigen capture using SHIV infected cells. Cells were incubated with 0, 0.1, 1, 10 or 100 nM drug prior to infection with SHIV. Viral titer was measured after infection by analyzing levels of p27 antigen. Results for incubation with WZ40, WZZL811S and WZ41 are provided in FIGS. 15 and 16. Test compounds inhibited SHIV infection at all concentrations tested. The inhibition was measurable at 2 days, and continued to 5 day incubations.

Example 10

Test Compound Activity Against HIV Strains

A selected set of compounds are tested for their ability to inhibit the cellular entry of T-tropic HIV. The assay for this inhibition is carried out on a contractural basis at Monogram Biosciences, Inc. using their well established Phenoscreen™ assay. Briefly, HIV strains of interest are tagged with a luciferase indicator gene to create an appropriate test vector. The test vector is amplified through transfection and the resulting virus is incubated in the presence of target host cells where intracellular florescence activity then becomes a measure of infection. Amplified virus is exposed to target host cells in the presence of a range of test drug concentrations to determine $IC_{50}$ measurements of entry inhibition. A modification of this test is further reapplied as a novel drug assay used in partnership with a number of pharmaceutical companies to test the effectiveness of novel entry inhibitors that target specific chemokines. It can used to detect activity against T-tropic, M-tropic, and dual-tropic viruses and Monogram Biosciences has a large bank of over 10,000 different virus strains to ultimately asses the range of applicability of our CXCR4 antagonists. Certain compounds are tested to establish efficacy in a number of viral strains.

We claim:

1. A compound selected from the group consisting of:

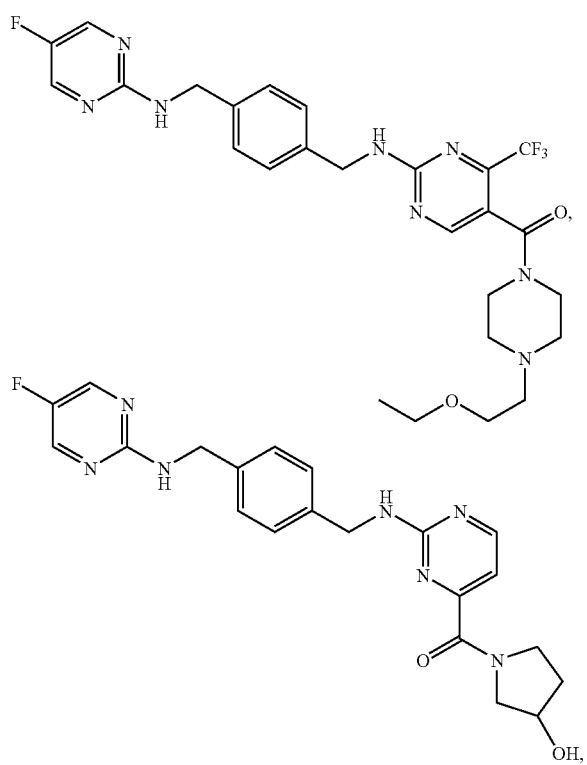

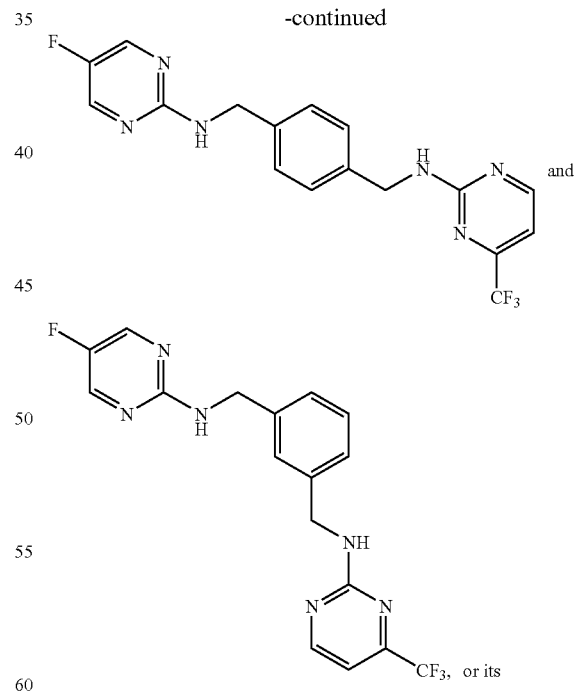

pharmaceutically acceptable salt or ester.

2. A method of treating metastatic cancer comprising administering an effective amount of a compound of claim 1 to a host in need thereof wherein the metastatic cancer is lung cancer, glioma, glioblastoma, pancreatic cancer, colorectal cancer, leukemia, oral cancer, gastric cancer, breast cancer, brain cancer, or ovarian cancer.

3. A method of treating an HIV infection, or of reducing symptoms associated with AIDS comprising administering an effective amount of a compound of claim 1 to a host in need thereof.

4. A compound of formula V:

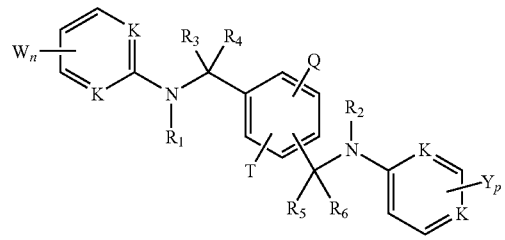

(III)

or its pharmaceutically acceptable salt, wherein:
each K is N;
Y is R or CONRR';
W is halogen;
Each Q and T are each independently H, R, acyl, F, Cl, Br, I, OH, OR, $NH_2$, NHR, $NR_2$, SR, $S_2R$, S—NHR, $S_2$—NHR, S—NRR', $S_2$—NRR', NHacyl, N(acyl)$_2$, $CO_2H$, $CO_2R$, CONRR', or CN, where R and R' are independently selected from straight chain, branched or cyclic alkyl, alkenyl, alkynyl, heteroalkyl, haloalkyl or aralkyl, aryl and heteroaryl;
n is 0 or 1;
p is 1 or 2;
$R^1$ and $R^2$ are hydrogen;
$R^3$, $R^4$, $R^5$ and $R^6$ are independently selected from H, straight chain, branched or cyclic alkyl, aralkyl, aryl, heteroaryl, acyl and imidolyl groups.

5. The compound of claim 4, wherein Y is haloalkyl.

6. A method of treating metastatic cancer comprising administering an effective amount of a compound of claim 4 to a host in need thereof wherein the metastatic cancer is lung cancer, glioma, glioblastoma, pancreatic cancer, colorectal cancer, leukemia, oral cancer, gastric cancer, breast cancer, brain cancer, or ovarian cancer.

7. A method of treating an HIV infection, or of reducing symptoms associated with AIDS comprising administering an effective amount of a compound of claim 4 to a host in need thereof.

* * * * *

SEQUENCE LISTING

```
<160> NUMBER OF SEQ ID NOS: 3

<210> SEQ ID NO 1
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
```

```
<223> OTHER INFORMATION: n = deoxythymidine

<400> SEQUENCE: 1
uaaaaucuuc cugcccaccn n                                    21

<210> SEQ ID NO 2
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n = deoxythymidine

<400> SEQUENCE: 2
ggaagcuguu ggcugaaaan n                                    21

<210> SEQ ID NO 3
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(21)
<223> OTHER INFORMATION: n = deoxythymidine

<400> SEQUENCE: 3
uucaaguugg aauugguagn n                                    21
```